US008821897B2

(12) United States Patent
Johnston et al.

(10) Patent No.: US 8,821,897 B2
(45) Date of Patent: Sep. 2, 2014

(54) VIRAL ADJUVANTS

(75) Inventors: Robert E. Johnston, Chapel Hill, NC (US); Joseph M. Thompson, Raleigh, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 952 days.

(21) Appl. No.: 12/954,021

(22) Filed: Nov. 24, 2010

(65) Prior Publication Data
US 2011/0064772 A1 Mar. 17, 2011

Related U.S. Application Data

(62) Division of application No. 11/628,512, filed as application No. PCT/US2005/024424 on Jul. 8, 2005, now Pat. No. 7,862,829.

(60) Provisional application No. 60/586,881, filed on Jul. 9, 2004.

(51) Int. Cl.
A61K 39/39 (2006.01)
A61K 39/193 (2006.01)
A61K 39/12 (2006.01)
C07K 14/005 (2006.01)
A61K 39/145 (2006.01)
A61K 39/00 (2006.01)

(52) U.S. Cl.
CPC ....... *A61K 39/39* (2013.01); *C12N 2760/16134* (2013.01); *A61K 2039/55555* (2013.01); *C12N 2770/36132* (2013.01); *C12N 2770/36143* (2013.01); *A61K 2039/541* (2013.01); *A61K 2039/5258* (2013.01); *C07K 14/005* (2013.01); *A61K 2039/55511* (2013.01); *A61K 39/12* (2013.01); *A61K 2039/55561* (2013.01); *A61K 39/145* (2013.01)
USPC .................. 424/281.1; 424/205.1; 424/218.1; 424/184.1

(58) Field of Classification Search
CPC .................... A61K 39/39; C12N 2770/16134; C12N 2770/36132
See application file for complete search history.

(56) References Cited

U.S. PATENT DOCUMENTS

| | | | |
|---|---|---|---|
| 4,650,764 A | 3/1987 | Temin et al. | |
| 5,091,309 A | 2/1992 | Schlesinger et al. | |
| 5,185,440 A | 2/1993 | Davis et al. | |
| 5,217,879 A | 6/1993 | Huang et al. | |
| 5,505,947 A | 4/1996 | Johnston et al. | |
| 5,639,650 A | 6/1997 | Johnston et al. | |
| 5,643,576 A * | 7/1997 | Johnston et al. ........... 424/199.1 | |
| 5,739,026 A | 4/1998 | Garoff et al. | |
| 5,766,602 A | 6/1998 | Xiong et al. | |
| 5,789,245 A | 8/1998 | Dubensky, Jr. et al. | |
| 5,792,462 A * | 8/1998 | Johnston et al. ........... 424/199.1 | |
| 5,811,407 A | 9/1998 | Johnston et al. | |
| 5,814,482 A | 9/1998 | Dubensky, Jr. et al. | |
| 5,843,723 A | 12/1998 | Dubensky, Jr. et al. | |
| 5,951,975 A | 9/1999 | Falo, Jr. et al. | |
| 5,994,126 A | 11/1999 | Steinman et al. | |
| 6,004,807 A | 12/1999 | Banchereau et al. | |
| 6,008,035 A | 12/1999 | Johnston et al. | |
| 6,013,516 A | 1/2000 | Verma et al. | |
| 6,015,694 A | 1/2000 | Dubensky et al. | |
| 6,156,304 A | 12/2000 | Glorioso et al. | |
| 6,156,558 A | 12/2000 | Johnston et al. | |
| 6,190,666 B1 | 2/2001 | Garoff et al. | |
| 6,224,879 B1 | 5/2001 | Sjoberg et al. | |
| 6,242,259 B1 | 6/2001 | Polo et al. | |
| 6,277,633 B1 | 8/2001 | Olsen | |
| 6,376,236 B1 | 4/2002 | Dubensky, Jr. et al. | |
| 6,468,982 B1 | 10/2002 | Weiner et al. | |
| 6,521,235 B2 | 2/2003 | Johnston et al. | |
| 6,521,457 B2 | 2/2003 | Olsen | |
| 6,531,135 B1 | 3/2003 | Johnston et al. | |
| 6,541,010 B1 | 4/2003 | Johnston et al. | |
| 6,583,121 B1 | 6/2003 | Johnston et al. | |
| 6,783,939 B2 | 8/2004 | Olmsted et al. | |
| 6,844,188 B1 | 1/2005 | MacDonald et al. | |
| 7,045,335 B2 | 5/2006 | Smith et al. | |
| 2001/0016199 A1 | 8/2001 | Johnston et al. | |
| 2003/0091591 A1 | 5/2003 | Xiong et al. | |
| 2003/0232035 A1 | 12/2003 | Dubensky, Jr. et al. | |
| 2003/0232036 A1 | 12/2003 | Johnston et al. | |
| 2004/0030117 A1 | 2/2004 | Johnston et al. | |

(Continued)

FOREIGN PATENT DOCUMENTS

EP 0 659 885 A1 12/1994
WO WO 92/10578 6/1992

(Continued)

OTHER PUBLICATIONS

Ying et al (Nature Medicine 5(7):823-827, 1999).*

(Continued)

*Primary Examiner* — Mary E Mosher
(74) *Attorney, Agent, or Firm* — Myers Bigel Sibley & Sajovec, P.A.

(57) ABSTRACT

The present invention provides viral adjuvants for enhancing an immune response to an immunogen. In particular embodiments, the viral adjuvant is an alphavirus adjuvant or a Venezuelan Equine Encephalitis viral adjuvant. Also provided are compositions comprising the viral adjuvant and an immunogen, and pharmaceutical formulations comprising the viral adjuvant or compositions of the invention in a pharmaceutically acceptable carrier. Further provided are methods of producing an immune response against an immunogen in a subject comprising administering the immunogen and a viral adjuvant of the invention to the subject.

21 Claims, 20 Drawing Sheets

(56) References Cited

U.S. PATENT DOCUMENTS

| | | |
|---|---|---|
| 2004/0121466 A1 | 6/2004 | Johnston et al. |
| 2004/0166573 A1 | 8/2004 | Smith et al. |
| 2004/0208848 A1 | 10/2004 | Smith et al. |
| 2005/0054107 A1 | 3/2005 | Chulay et al. |
| 2005/0123555 A1 | 6/2005 | Olmsted et al. |
| 2006/0099587 A1 | 5/2006 | Johnston et al. |
| 2006/0177819 A1 | 8/2006 | Smith et al. |
| 2007/0166820 A1 | 7/2007 | Smith et al. |

FOREIGN PATENT DOCUMENTS

| | | |
|---|---|---|
| WO | WO 95/07994 | 3/1995 |
| WO | WO 95/27044 | 10/1995 |
| WO | WO 95/31565 | 11/1995 |
| WO | WO 95/32733 | 12/1995 |
| WO | WO 96/17072 | 6/1996 |
| WO | WO 96/21416 | 7/1996 |
| WO | WO 96/37220 | 11/1996 |
| WO | WO 96/37616 | 11/1996 |
| WO | WO 97/24447 | 7/1997 |
| WO | WO 97/38087 | 10/1997 |
| WO | WO 98/00163 | 1/1998 |
| WO | WO 98/36779 | 8/1998 |
| WO | WO 98/50071 | 11/1998 |
| WO | WO 99/30734 | 6/1999 |
| WO | WO 99/51263 | 10/1999 |
| WO | WO 00/32227 | 6/2000 |
| WO | WO 00/39318 | 7/2000 |
| WO | WO 01/16343 | 3/2001 |
| WO | WO 01/47456 | 7/2001 |
| WO | WO 02/20721 | 3/2002 |
| WO | WO 02/099035 A2 | 12/2002 |
| WO | WO 03/083065 | 10/2003 |
| WO | WO 2004/044157 A2 | 5/2004 |
| WO | WO 2007/046869 A2 | 4/2007 |

OTHER PUBLICATIONS

Cheng et al (Human Gene Therapy 13:553-568, 2002).*
Caley et al (Vaccine 17:3124-3135, 1999).*
Kast (Cancer Immunol. Immunother. 52(Suppl1): S30 and S17, 2003).*
Velders et al (Cancer Research 61:7861-7867, 2001).*
Craig et al. (Journal of Immunology 102:1220-1227, 1969).
Howard et al. (Journal of Immunology 103:699-707, 1969).
Hruskova et al. (Acta Virologica 16:155-124, 1972) (Hruskova A).
Hruskova et al. (Acta Virologica 16:125-132, 1972) (Hruskova B).
Jochim et al. (Journal of the American Veterinary Medical Association 165(7): 621-625, 1974, abstract only cited).
Dorange F. et al., "Vesicular stomatitis virus glycoprotein: a transducing coat for SFV-based RNA vectors", The Journal of Gene Medicine, 2004, vol. 6, pp. 1014-1022.
Gardner C. et al., "Eastern and Venezuelan Equine Encephalitis Viruses Differ in Their Ability to Infect Dendritic Cells and Macrophages: Impact of Altered Cell Tropism on Pathogenesis", Journal of Virology, Nov. 2008, vol. 82, No. 21, pp. 10634-10646.
International Search Report and the Written Opinion of the International Searching Authority for PCT Application No. PCT/US05/24424, mailed Aug. 14, 2007.
Berglund et al.; "Immunization with recombinant Semliki Forest virus induces protection against influenza challenge in mice," Vaccine 17 (1999) p. 497-507.
Pushko et al.; "Replicon-Helper Systems from Attenuated Venezuelan Equine Encephalitis Virus: Expression of Heterologous Genes in Vitro and Immunization Against Heterologous Pathogens in Vivo," Virology 239, (1997) p. 389-401.
Tsiang et al.; "Effects of 5'-Terminal Modifications on the Biological Activity of Defective Interfering RNAs of Sindbis Virus," Journal of Virology 62(1), 1988, p. 47-53.
Balasuriya et al. "Alphavirus Replicon Particles Expressing the Two Major Envelope Proteins of Equine Arteritis Virus Induce High Level Protection Against Challenge with Virulent Virus in Vaccinated Horses" *Vaccine* 20:1609-1617 (2002).

Balasuriya et al. "Expression of the Two Major Envelope Proteins of Equine Arteritis Virus as a Heterodimer is Necessary for Induction of Neutralizing Antibodies in Mice Immunized with Recombinant Venezuelan Equine Encephalitis Virus Replicon Particles" *Journal of Virology* 74(22):10623-10630 (2000).

Barclay et al. "Encapsidation Studies of Poliovirus Subgenomic Replicons" *Journal of General Virology* 279:1725-1734 (1998).

Barrett et al. "Antibody-mediated Early Death in vivo after Infection with Yellow Fever Virus" *Journal of General Virology* 67:2530-2542 (1986).

Berge et al. "Studies on the Virus of Venezuelan Equine Encephalomyelitis," *Journal of Immunology* 87:509-517 (1961).

Berglund et al. "Immunization with recombinant Semliki Forest virus induces protection against influenza challenge in mice," *Vaccine* 17:497-507 (1999).

Berglund et al. "Outcome of Immunization of Cynomolgus Monkeys with Recombinant Semliki Forest Virus Encoding Human Immunodeficiency Virus Type 1 Envelope Protein and Challenge with a High Dose of SHIV-4 Virus" *Aids Research and Human Retroviruses* 13(17):1487-95 (1997).

Bernard et al. "Mutations in the E2 Glycoprotein of Venezuelan Equine Encephalitis Virus Confer Heparan Sulfate Interaction, Low Morbidity, and Rapid Clearance from Blood of Mice" *Virology* 276:93-103 (2000).

Boisgerault et al. "Cross-Priming of T Cell Responses by Synthetic Microspheres Carrying a $CD84^+$ T Cell Epitope Requires an Adjuvant Signal" *The Journal of Immunology* 3432-3439 (2005).

Bouvet et al. "Stimulation of local antibody production: parenteral or mucosal vaccination?" *Trends in Immunology* 23(4):209-213 (Apr. 2002).

Bowers et al. "Dendritic Cell Ontogeny," 28th Forum in Immunology, Medical Research Institute, The Mary Imogene Bassett Hospital, Cooperstown, NY.

Bredenbeek et al. "Sindbis Virus Expression Vectors: Packaging of RNA Replicons by Using Defective Helper RNAs" *Journal of Virology* 67(11):6439-6446 (1993).

Brimnes et al. "Influenza Virus-Induced Dendritic Cell Maturation Is Associated with the Induction of Strong T Cell Immunity to a Coadministered, Normally Nonimmunogenic Protein" *The Journal of Experimental Medicine* 198(1):133-144 (Jul. 7, 2003).

Bukreyev et al. "A Single Intranasal Inoculation with a Paramyxovirus-Vectored Vaccine Protects Guinea Pigs Against a Lethal-Dose Ebola Virus Challenge" *Journal of Virology* 80(5):2267-2279 (2006).

Bukreyev et al. "Recombinant Newcastle Disease Virus Expressing a Foreign Viral Antigen is Attenuated and Highly Immunogenic in Primates" *Journal of Virology* 79(21):13275-13284 (2005).

Bulychyov et al. "Disease Course in Guinea Pigs After Aerogenous Infection with Venezuelan Equine Encaphalomyelitis Virus" ISSN 0507-4088 (1995) (Whole article, only abstract translated).

Caley et al. "Humoral, Mucosal, and Cellular Immunity in Response to a Human Immunodeficiency ViruS Type 1 Immunogen Expressed by a Venezuelan Equine Encephalitis Virus Vaccine Vector" *Journal of Virology* 71(4):3031-3038 (1997).

Carl et al. "Effect of the Attenuating Deletion and of Sequence Alterations Evolving In Vivo on Simian Immunodeficiency Virus C8-Nef Function" *Journal of Virology* 73(4):2790-2797 (1999).

Chanas et al. "Monoclonal Antibodies to Sindbis Virus Glycoprotein E1 can Neutralize, Enhance Infectivity, and Independently Inhibit Haemagglutination or Haemolysis" *Journal of General Virology* 58:37-46 (1982).

Chang et al. "Retroviral Vectors for Gene Therapy of AIDS and Cancer" *Current Opinion in Molecular Therapeutics* 3(5):468-475 (2001).

Charles et al. "Mucosal Immunity Induced by Parenteral Immunization with a Live Attentuated Venezuelan Equine Encephalitis Virus Vaccine Candidate" *Virology* 228:153-160 (1997).

Coffin et al. "Induction of Virus-Specific Antibody Production by Lamina Propria Lymphocytes Following Intramuscular Inoculation with Rotavirus" *The Journal of Infectious Diseases* 172: 874-878 (1995).

(56) References Cited

OTHER PUBLICATIONS

Corsini et al. "Efficiency of Transduction by Recombinant Sindbis Replicon Virus Varies Among Cell Lines, Including Mosquito Cells and Rat Sensory Neurons" *BioTechniques* 21(3):492-497 (Sep. 1996).

Curtis et al. "Heterologous Gene Expression from Transmissible Gastroenteritis Virus Replicon Particles" *Journal of Virology* 76(3):1422-1434 (2002).

Davis et al, "A Genetically Engineered Live Virus Vaccine for Venezuelan Equine Encephalitis" *J. Cell Biochemistry* Supplement O No. 17 Part D, issued 1993, Abstract N404.

Davis et al. "A molecular genetic approach to the study of Venezuelan equine encephalitis virus pathogenesis" *Archives of Virology* 9:99-109 (1994).

Davis et al. "An Attenuated VEE Virus Vaccine Vector: Expression of HIV-1 and Influenza Genes in Cell Culture and Protection Against Influenza Challenge in Mice Immunized with a Vector Expressing HA" *Vaccines* 387-391 (1995).
Davis et al. "Attenuated Mutants of Venezuelan Equine Encephalitis Virus Containing Lethal Mutations in the PE2 Cleavage Signal Combined with a Second-Site Suppressor Mutation in E1" *Virology* 212:102-110 (1995).
Davis et al. "Attenuating Mutations in the E2 Glycoprotein Gene of Venezuelan Equine Encephalitis Virus: Construction of Single and Multiple Mutants in a Full-Length cDNA Clone" *Virology* 183:20-31 (1991).
Davis et al. "A Viral Vaccine Vector that Expresses Foreign Genes in Lymph Nodes and Protects Against Mucosal Challenge" *Journal of Virology* 70(6):3781-3787 (1996).
Davis et al. "In Vitro Synthesis of Infectious Venezuelan Equine Encephalitis Virus RNA from a cDNA Clone: Analysis of a Viable Deletion Mutant," *Virology* 171:189-204 (1989).
Davis et al. "In Vitro Synthesis of Infectious Venezuelan Equine Encephalitis Virus RNA from a cDNA Clone: Analysis of a Viable Deletion Mutant and Mutations Affecting Virulence" *Vaccines* 90:109-113 (1990).
Davis et al, "Vaccination of Macaques Against Pathogenic Simian Immunodeficiency Virus with Venezuelan Equine Encephalitis Virus Replicon Particles" *Journal of Virology* 74(1):371-378 (2000).
Decroix et al. "Mucosal Immunity Induced by Intramuscular Administration of Free Peptides In-Line with PADRE: IgA Antibodies to the ELDKWA Epitope of HIV gp41" *Scand. J. Immunol.* 56:59-65 (2002).
De Veerman et al. "Retrovirally Transduced Bone Marrow-Derived Dendritic Cells Require $CD4^+$ T Cell Help to Elicit Protective and Therapeutic Antitumor Immunity" *The Journal of Immunology* 162:144-151 (1999).
Dietz et al. "High Efficiency Adenovirus-Mediated Gene Transfer to Human Dendritic Cells" *Blood* 91(2):392-398 (1998).
Disis et al. "Peptide-Based, but Not Whole Protein, Vaccines Elicit Immunity to HER-2/neu, an Oncogenic Self-Protein" *Journal of Immunology* 156:3151-3158 (1996).
Dubensky, Jr. et al. "Sindbis Virus DNA-Based Expression Vectors: Utility for in Vitro and in Vivo Gene Transfer," *Journal of Virology* 70(1):508-519 (Jan. 1996).
Egan et al. "A comparative evaluation of nasal and parenteral vaccine adjuvants to elicit systemic and mucosal HIV-1 peptide-specific humoral immune responses in cynomolgus macques" *Vaccine* 22:3744-3788 (2004).
Engler et al. "Venezuelan Equine Encephalitis-Specific Immunoglobulin Responses: Live Attenuated TC-83 Versus Inactivated C-84 Vaccine" *Journal of Medical Virology* 38:305-310 (1992).
Enioutina et al. "The induction of systemic and mucosal immune responses following the subcutaneous immunization of mature adult mice: characterization of the antibodies in mucosal secretions of animals immunized with antigen formulations containing a vitamin D3 adjuvant" *Vaccine* 17:3050-3064 (1999).
Evans et al. "A Novel Approach for Producing Lentiviruses That are Limited to a Single Cycle of Infection" *Journal of Virology* 78(21): 11715-11725 (2004).
Flynn et al. "Antibody-Mediated Activation of Sindbis Virus" *Virology* 166:82-90 (1988).
Foley et al. "Rhabdovirus-Based Vectors with Human Immunodeficiency Virus Type 1 (HIV-1) Envelopes Display HIV-1-Like Tropism and Target Human Dendritic Cells" *Journal of Virology* 76(1):19-31 (2002).
Fosmire et al. "Identification and Characterization of a Coronavirus Packaging Signal" *Journal of Virology* 66(6):3522-3530 (1992).
Frolov et al. "Alphavirus-based expression vectors: Stategies and applications" *Proc. Natl. Acad. Sci. USA* 93:11371-11377 (1996).
Frolov et al. "Comparison of the Amino Acid Sequences of Structural Proteins of Attenuated and Pathogenic Strains of Venezuelan Equine Encephalomyelitis Virus" *Doklady Biochemistry* 318:144-146 (1991).
Frolov et al. "Influence of Mutations in Genes of the Structural Proteins of Venezuelan Equine Encephalomyelitis on its Attenuation" *Doklady Biological Sciences* 326:466-469 (1992).
Frolov et al. "Recombinant VEE Virus Expresses HBsAg" *Proceedings, IXth International Congress of Virology* p. 67 (Aug. 8-13, 1993).
Frolov et al. "Recombinant Venezuelan Equine Encephalomyelitis Viruses Expressing HBsAg" *Papers of the Academy of Science* 332(6):789-791 (1993).
Frolov et al. "Translation of Sindbis Virus mRNA: Analysis of Sequences Downstream of the Initiating AUG Codon That Enhance Translation" *Journal of Virology* 70(2):1182-1190 (1996).
Frolov et al. "Translation of Sindbis Virus mRNA: Effects of Sequences Downstream of the Initiating Codon," *Journal of Virology* 68(12):8111-8117 (1994).
Frolova et al. "Packaging Signals in Alphaviruses," *Journal of Virology* 71(1):248-258 (Jan. 1997).
Fust, G. "Enhancing antibodies in HIV infection" *Parasitology* Supplemental 115:127-140 (1997).
Galili et al. "Natural Anti-Gal Antibody as a Universal Augmenter of Autologous Tumor Vaccine Immunogenicity" *Viewpoint Immunology Today* 18(6):281-285 (1997).
Gardner et al. "Infection of Human Dendritic Cells by a Sindbis Virus Replicon Vector is Determined by a Single Amino Acid Substitution in the E2 Glycoprotein" *Journal of Virology* 74(24):11849-11857 (2000).
Geigenmuller-Gnirke et al. "Complementation Between Sindbis Viral RNAs Produces Infectious Particles with a Bipartite Genome" *Proceedings of the National Academy of Sciences of the United States of America* 88(8):3253-3257 (Apr. 15, 1991).
Glasgow et al. "A single amino acid change in the E2 spike protein of a virulent strain of Semliki Forest virus attenuates pathogenicity" *Journal of General Virology* 75:663-668 (1994).
Glasgow et al. "Two Mutations in the Envelope Glycoprotein E2 of Semliki Forest Virus Affecting the Maturation and Entry Patterns of the Virus Alter Pathogenicity for Mice" *Virology* 185:741-748 (1991).
Glenn et al. "Transcutaneous immunization: A human vaccine delivery strategy using a patch" *Nature Medicine* 6(12):1403-1406 (2000).
Grieder et al. "Specific Restrictions in the Progression of Venezuelan Equine Encephalitis Virus-Induced Disease Resulting from Single Amino Acid Changes in the Glycoproteins" *Virology* 206:994-1006 (1995).
Gupta et al. "Characterization of Human Immunodeficiency Virus Gag-Specific Gamma Interferon-Expressing Cells Following Protective Mucosal Immunization with Alphavirus Replicon Particles" *Journal of Virology* 79(11):7135-7145.
Guyre et al. "Increased potency of Fc-receptor-targeted antigens" *Cancer Immunology, Immunotherapy* 45:146-148 (1997).
Hahn et al. "Infectious Sindbis Virus Transient Expression Vectors for Studying Antigen Processing and Presentation" *Proc. Natl. Acad. Sci. USA* 89:2679-2683 (1992).
Hahn et al. "Site-Directed Mutagenesis of the Proposed Catalytic Amino Acids of the Sindbis Virus Capsid Protein Autoprotease" *Journal of Virology* 64(6):3069-3073 (Jun. 1990).
Harrington et al. "Systemic, Mucosal, and Heterotypic Immune Induction in Mice Inoculated with Venezuelan Equine Encephalitis Replicons Expressing Norwalk Virus-Like Particles" *Journal of Virology* 76(2):730-742 (2002).

(56) References Cited

OTHER PUBLICATIONS

Hawkes et al. "The Enhancement of Virus Infectivity by Antibody" *Virology* 33:250-261 (1967).

Heidner et al. "Lethality of PE2 Incorporation into Sindbis Virus Can Be Suppressed by Second-Site.Mutations in E3 and E2" *Journal of Virology* 68(4):2683-2692 (1994).

Heise et al. "Adult Mouse Neurovirulence Determinants Within the Nonstructural Genes of the Sindbis-Group Alphavirus S.A.AR86" *American Society of Virology Meeting*, Colorado, Oral Presentation (Jul. 11, 2000).

Heise et al. "A Single Amino Acid Change in nsP1 Attenuates Neuroviolence of the Sindbis-Group Alphavirus S.A.AR86" *Journal of Virology* 74:9 (May 2000).

Heise et al. "Sindbis-Group Alphavirus Replication in Periosteum and Endosteum of Long Bones in Adult Mice" *Journal of Virology* 74(19):9294-9299 (Oct. 2000).

Heise et al. "The Role of Viral Nonstructural Genes in Neuroviruience of the Sindbis-Group Virus, S.A.AR86," *Keystone Symposia*, Taos, New Mexico, p. 306 (Feb. 2000).

Heufler et al. "Granulocyte/Macrophage Colony-Stimulating Factor and Interleukin 1 Mediate the Maturation of Murine Epidermal Langerhans Cells into Potent Immunostimulatory Dendritic Cells" *Journal of Experimental Medicine* 167:700-705 (1988).

Hodgson et al. "Expression of Venezuelan Equine Encephalitis Virus Proteins by Recombinant Baculoviruses" Program and Abstracts of the Joint Annual Meeting of the American Society of Tropical Medicine and Hygiene and the American Society of Parasitologists, Supplement to the American Journal of Tropical Medicine and Hygiene 49(3): 195-196 (Abstract # 183)(1993).

Hutchings et al. "Novel Protein and Poxvirus-Based Vaccine Combinations for Simultaneous Induction of Humoral and Cell-Mediated Immunity" *The Journal of Immunology* 599-606 (2005).

Ikonomidis et al. "Influenza-Specific Immunity Induced by Recombinant *Listeria monocytogenes* Vaccines" *Vaccines* 15(4):433-440 (1997).

Inada et al. "Association of Virulence of Murine Cytomegalovirus with Macrophage Susceptibility and with Virion-bound Non-neutralizing Antibody" *Journal of General Virology* 66:879-882 (1985).

Inada et al, "Enhancing Antibodies, Macrophages and Virulence in Mouse Cytomegalovirus Infection" *Journal of General Virology* 66:871-878 (1985).

Jochim et al. "Immune Response of Horses After Simultaneous or Sequential Vaccination Against Eastern, Western, and Venezuelan Equine Encephalomyelitis" *J.A.V.M.A* 165(7):621-625 (1974).

Johnson et al. "Specific Targeting to CD4+ Cells of Recombinant Vesicular Stomatitis Viruses Encoding Human Immunodeficiency Virus Envelope Proteins" *Journal of Virology* 71(7):5060-5068 (1997).

Johnston et al. "Alphavirus Vaccine Systems for Emerging Infections" Symposium on "Challenges for Vaccine Development for Emerging Infections in the 21$^{st}$ Century" Duke University, Durham, NC, Nov. 12, 2004, Oral Presentation, 70 pages.

Johnston et al. "Alphavirus Vectors: Biology and Vaccine Potential" Abstract ECEAR Meeting Edinburgh, Scotland (Jun. 23-26, 2001).

Johnston et al. "Vaccination of macaques with SIV immunogens delivered by Venezuelan equine encephalitis virus replicon particle vectors followed by a mucosal challenge with SIVsmE660" *Vaccine* 23:4969-4979 (2005).

Jones et al. "Construction and Applications of Yellow Fever Virus Replicons" *Virology* 331:247-259 (2005).

Kawabata et al. "Induction of Th2 Cytokine Expression for p27-Specific IgA B Cell Responses After Targeted Lymph Node Immunization with Simian Immunodeficiency Virus Antigens in Rhesus Macaques" *The Journal of Infectious Diseases* 177:26-33 (1998).

Kawakami et al. "Section 3.1 Genes coding for Tumor Antigens Recognized by T Lymphocytes" *Biological Therapy of Cancer* 2nd Edition:53-63 J.B. Lippincott Company (1995).

Kinney et al. "Attenuation of Venezuelan Equine Encephalitis Virus Strain TC-83 Is Encoded by the 5'-Noncoding Region and the E2 Envelope Glycoprotein" *Journal of Virology* 67(3):1269-1277 (Mar. 1993).

Kinney et al. "The Full-Length Nucleotide Sequence of the Virulent Trinidad Donkey Strain of Venezuelan Equine Encephalitis Virus and Its Attenuated Vaccine Derivative, Strain TC-83" *Virology* 170:19-30 (1989).

Kotsopoulou et al. "A Rev-Independent Human Immunodeficiency Virus Type 1 (HIV-1)-Based Vector that Exploits a Codon-Optimized HIV-1 gag-pol Gene" *Journal of Virology* 74(10):4839-4852 (2000).

Leitner et al. "Alphavirus-based DNA Vaccine Breaks Immunological Tolerance by Activating Innate Antiviral Pathways" *Nature Medicine* 9(1):33-39 (2003).

Lemm et al. "Polypeptide requirements for assembly of functional Sindbis virus replication complexes: a model for the temporal regulation of minus- and plus-strand RNA synthesis" *The EmBO Journal* 13(12):2925-2934 (1994).

Liljestrom. "Alphavirus expression systems" *Current Opinion in Biotechnology*, 5(5):495-500 (Oct. 1994).

Liljestrom. "Alphavirus Vectors for Gene Delivery" OECD Documents, Gene Delivery Systems, 109-118 (1996).

Liljestrom et al. "A New Generation of Animal Cell Expression Vectors Based on the Semliki Forest Virus Replicon" *Bio/Technology* 9:1356-1361 (1991).

Linn et al. "Antibody-dependent enhancement and persistence in macrophages of an arbovirus associated with arthritis," *Journal of General Virology* 77:407-411 (1996).

London et al. "Infectious Enveloped RNA Virus Antigenic Chimeras," *Proc. Natl. Acad. Sci. USA* 89:207-211 (1992).

Lvov et al. "Karshi Virus, a New Flavivirus (Togaviridae) Isolated from *Ornithodoros papillipes* (Birula, 1895) Ticks in Uzbek S.S.R." *Archives of Virology* 50:29-36 (1976).

MacDonald et al. "Role of Dendritic Cell Targeting in Venezuelan Equine Encephalitis Virus Pathogenesis" *Journal of Virology* 74(2):914-922 (2000).

Mady et al. "Neuraminidase augments Fcγ receptor II-mediated antibody-dependent enhancement of dengue virus infection" *Journal of General Virology* 74:839-844 (1993).

McKenna et al. "Covalently Linked Human Immunodeficiency Virus Type 1 gp120/gp41 Is Stably Anchored in Rhabdovirus Particles and Exposes Critical Neutralizing Epitopes" *Journal of Virology* 77(23):12782-12794 (2003).

McKenzie et al. "Biological advances and clinical application of Fc receptors for IgG" *Current Opinion in Hematology* 1:45-52 (1994).

McKenzie et al. "Bypassing luminal barriers, delivery to a gut addressin by parenteral targeting elicits local IgA responses" *International Immunology* 16(11):1613-1622.

McKnight. "The Human Rhinovirus Internal cis-acting Replication Element (cre) Exhibits Disparate Properties Among Serotypes" *Arch Virol* 148:2397-2418 (2003).

McKnight et al. "Deduced Consensus Sequence of Sindbis Virus Strain AR339: Mutations Contained in Laboratory Strains which Affect Cell Culture and in Vivo Phenotypes," *Journal of Virology*, 70(3) 1981-1989 (1996).

Moran et al. "A Novel Viral System for Generating Antigen-Specific T Cells" *The Journal of Immunology* 3431-3438 (2005).

Morens. "Antibody-Dependent Enhancement of Infection and the Pathogenesis of Viral Disease" *Clinical Infectious Diseases* 19:500-512 (1994).

Morens et al. "Measurement of antibody-dependent infection enhancement of four dengue virus serotypes by monoclonal and polyclonal antibodies" *Journal of General Virology* 71:2909-2914 (1990).

Morgenstern et al. "Advanced mammalian gene transfer: high titre retroviral vectors with multiple drug selection markers and a complementary helper-free packaging cell line" *Nucleic Acids Research* 18(12):3587-3596 (1990).

Musey et al. "HIV-1 Vaccination Administered Intramuscularly Can Induce Both Systemic and Mucosal T Cell Immunity in HIV-1-Uninfected Individuals" *The Journal of Immunology* 1094-1101 (2003).

(56) References Cited

OTHER PUBLICATIONS

Notification of Transmittal of the International Search Report and the Written Opinion of the International Searching Authority, or the Declaration, PCT/US05/24424 mailed Aug. 14, 2007.
Ochiai et al. "Infection Enhancement of Influenza A NWS Virus in Primary Murine Macrophages by Anti-Hemagglutinin Monoclonal Antibody" *Journal of Medical Virology* 36:217-221 (1992).
Ogra et al. "Antibody Response in Serum and Nasopharynx After Naturally Acquired and Vaccine-Induced Infection with Rubella Virus" *The New England Journal of Medicine* 285(24):1333-1339.
Olsen. "A review of feline infectious peritonitis virus: molecular biology, immunopathogenesis, clinical aspects, and vaccination," *Veterinary Microbiology* 36:1-37 (1993).
Orkin et al. "Report and Recommendations of the Panel to Assess the NIH Investment in Research on Gene Therapy," *Current Science* 71(9):658-659 (1996).
O'Rourke et al. "Analysis of Gene Transfer and Expression in Skeletal Muscle Using Enhanced EIAV Lentivirus Vectors" *Molecular Therapy* 7(5):632-639 (2003).
Pan et al. "A Recombinant *Listeria monocytogenes* Vaccine Expressing a Model Tumour Antigen Protects Mice Against Lethal Tumour Cell Challenge and Causes Regression of Established Tumors" *Nature Medicine* 1(5):471-477 (1995).
Pan et al. "Regression of Established Tumors in Mice Mediated by the Oral Administration of a Recombinant *Listeria monocytogenes* Vaccine" *Cancer Research* 55:4776-4779 (1995).
Pastrana et al. "NHPV16 VLP Vaccine Induces Human Antibodies that Neutralize Divergent Variants of HPV16" *Virology* 279:361-369 (2001).
Peiris et al. "Antibody-dependent Enhancement of Plaque Formation on Cell Lines of Macrophage Origin—A Sensitive Assay for Antiviral Antibody" *Journal of General Virology* 57:119-125 (1981).
Peiris et al. "Monoclonal anti-FC receptor IgG blocks antibody enhancement of viral replication in macrophages." Nature 289(Jan. 15):189-191 (1981).
Perri et al. "An Alphavirus Replicon Particle Chimera Derived from Venezuelan Equine Encephalitis and Sindbis Viruses Is a Potent Gene-Based Vaccine Delivery Vector" *Journal of Virology* 77(19):10394-10403 (2003).
Phumiamorn et al. "Induction of Humoral and Cell-Mediated Immunity to Hepatitis B Surface Antigen by a Novel Adjuvant Activity of Oka Varicella Vaccine" *Journal of General Virology* 84:287-291 (2003).
Polo et al. "Attenuating Mutations in Glycoproteins E1 and E2 of Sindbis Virus Produce a Highly Attenuated Strain When Combined in Vitro" *Journal of Virology* 64(9):4438-4444 (1990).
Polo et al. "Molecular Analysis of Sindbis Virus Pathogenesis in Neonatal Mice by Using Virus Recombinants Constructed In Vitro" *Journal of Virology* 62:2124-2133 (1988).
Porterfield. "Antibody-dependent Enhancement of Viral Infectivity," *Advances in Virus Research* 31:335-354 (1986).
Publicover et al. "Characterization of Nonpathogenic, Live, Viral Vaccine Vectors Inducing Potent Cellular Immune Responses" *Journal of Virology* 78(17):9317-9324 (2004).
Pushko et al. "Recombinant RNA Replicons Derived from Attenuated Venezuelan Equine Encephalitis Virus Protect Guinea Pigs and Mice from Ebola Hemorrhagic Fever Virus" *Vaccine* 19:142-153 (2001).
Pushko et al, "Replicon-Helper Systems from Attenuated Venezuelan Equine Encephalitis Virus: Expression of Heterologous Genes in Vitro and Immunization Against Heterologous Pathogens in Vivo" *Virology* 239:389-401 (1997).
Raabe et al. "In Vitro Antibody-Dependent Enhancement Assays are Insensitive Indicators of in Vivo Vaccine Enhancement of Equine Infectious Anemia Virus," *Virology* 259:416-427 (1999).
Reddy et al. "Optimization of bovine coronavirus hemagglutininestrase glycoprotein expression in E3 deleted bovine adenovirus-3" *Virus Research* 70:65-73 (2000).
Restifo. "The new vaccines: building viruses that elicit antitumor immunity" *Current Opinion in Immunology* 9:658-663 (1997).
Restifo et al. "Transfectant Influenza A Viruses Are Effective Recombinant Immunogens in the Treatment of Experimental Cancer" *Virology* 249:89-97 (1998).
Rose et al. "Defining the Level of Human Immunodeficiency Virus Type 1 (HIV-1) Protease Activity Required for HIV-1 Particle Maturation and Infectivity" *Journal of Virology* 69(5):2751-2758 (1995).
Rosenberg. "A New Era for Cancer Immunotherapy Based on the Genes that Encode Cancer Antigens" *Immunity* 10:281-287 (1999).
Russell et al. "Sindbis Virus Mutations Which Coordinately Affect Glycoprotein Processing, Penetration, and Virulence in Mice" *Journal of Virology* 63(4):1619-1629 (1989).
Schlesinger. "Alphaviruses—vectors for the expression of heterologous genes" *TIBTECH* 11:18-22 (1993).
Schlesinger et al. "17D Yellow Fever Virus Infection of P388D$_1$ Cells Mediated by Monoclonal Antibodies: Properties of the Macrophage Fc Receptor" *Journal of General Virology* 64:1255-1262 (1983).
Schlesinger et al. "Recombination between Sindbis virus RNAs" *Archives of Virology* Suppl. 9:213-220 (1994).
Schnell et al. "Recombinant Rabies Virus as Potential Live-Viral Vaccines for HIV-1" *PNAS* 97(7):3544-3549.
Schoepp et al., "Directed Mutagenesis of a Sindbis Virus Pathogenesis Site" *Virology* 193: 149-159 (1993).
Schuler et al. "Dendritic Cells as Adjuvants for Immune-mediated Resistance to Tumors" *J. Exp. Med.* 186(8):1183-1187 (1997).
Schultz-Cherry et al. "Influenza Virus (A/HK/156/97) Hemagglutinin Expressed by an Alphavirus Replicon System Protects Chickens Against Lethal Infection with Hong Kong-Origin H5N1 Viruses" *Virology* 278:55-59 (2000).
Simpson et al., Complete Nucleotide Sequence and Full-Length cDNA Clone of S.A.AR86, a South African Alphavirus Related to Sindbis, *Virology* 222:464-469, Article No. 0445 (1996).
"Sindbis-Like Virus Isolate Girdwood S.A., Complete Genome," EMBL Database, Accession No. U38304, (Jan. 3, 1996).
"Sindbis Virus (HRSP and Wild-Type Strains), Complete Genome," EMBL Database, Accession Nos. J02363, 02364, J02366, J02367, and V00073, (Jul. 3, 1991).
Sjoberg et al. "A Significantly Improved Semliki Forest Virus Expression System Based on Translation Enhancer Segments from the Viral Capsid Gene" *Bio/Technology* 12:1127-1131 (1994).
Soneoka et al. "A Transient Three-Plasmid Expression System for the Production of High Titer Retroviral Vectors" *Nucleic Acids Research* 23(4):628-633 (1995).
Song et al. "Antigen presentation in retroviral vector-mediated gene transfer in vivo" *Proc. Natl. Acad. Sci. USA* 94:1943-1948 (1997).
Song et al. "Dendritic Cells Genetically Modified with an Adenovirus Vector Encoding the cDNA for a Model Antigen Induce Protective and Therapeutic Antitumor Immunity" *J. Exp. Med.* 186(8):1247-1256 (1997).
Specht et al. "Dendritic Cells Retrovirally Transduced with a Model Antigen Gene Are Therapeutically Effective against Established Pulmonary Metastases" *J. Exp. Med.* 186(8):1213-1221 (1997).
Steinman. "The Dendritic Cell System and its Role in Immunogenicity" *Annual Review of Immunology* 9:271-296 (1991).
Storkus et al. "Section 3.2 Tumor Antigens Recognized by Immune Cells" *Biologic Therapy of Cancer* Second Edition, J.B. Lippincott Company, 1995 pp. 64-77.
Strauss et al. "The Alphaviruses: Gene Expression, Replication, and Evolution" *Microbiological Reviews* 58(3):491-562 (1994).
Suomalainen et al. "Spike Protein-Nucleocapsid Interactions Drive the Budding of Alphaviruses" *Journal of Virology* 66(8):4737-4747 (1992).
Thompson et al. "From the Foot to the Nose: VEE Replicon Particle Mucosal Immune Induction" Department of Microbiology and Immunology, University of North Carolina at Chapel Hill Student Seminar, Dec. 16, 2003, Chapel Hill, NC, Oral Presentation, 20 pages.
Thompson et al. "From the Foot to the Nose: VEE Replicon Particle Mucosal Immune Induction" University of North Carolina at Chapel Hill, Virology in Progress Series, Mar. 5, 2004, Chapel Hill, NC, Oral Presentation, 17 pages.
Thompson et al. "Investigation of Venezuelan Equine Encephalitis Virus Replicon Particle Mucosal Immune Induction" 2004 American

(56) References Cited

OTHER PUBLICATIONS

Society for Virology Meeting, Jul. 10, 2004, Montreal, Canada, Oral Presentation, Available on-line Apr. 2004, 7 pages.
Thompson et al. "Mucosal Adjuvant Activity of Venezuelan Equine Encephalitis Virus Replicon Particle Vaccine Vectors Following Parenteral Delivery in Mice" 2005 Society for Mucosal Immunology/International Congress of Mucosal Immunology Meeting Jun. 25-30, 2005, Boston MA, Poster Presentation, 2 pages.
Thompson et al. "Mucosal Immune Induction Following Peripheral Delivery of Venezuelan Equine Encephalitis Virus Replicon Particles" 2004 Southeastern Regional Virology Meeting, Mar. 27, 2004, Atlanta, GA, Oral Presentation, 7 pages.
Thompson et al. "Systemic and Mucosal Adjuvant Activity of Venezuelan Equine Encephalitis Virus Replicon Particles" 2005 American Society for Virology Meeting, Penn State, PA, Jun. 14-18, 2005, Oral Presentation, 19 pages.
Thompson et al. "VEE Replicon Particle (VRP) Mucosal Immune Induction in the Draining Lymph Node" ASM North Carolina Branch Fall 2003 Meeting Abstract, Oct. 10, 2003, Raleigh, NC, Oral Presentation, 8 pages.
Thompson et al. "VEE VRP Mucosal Immunity: Protection from Mucosal Challenge and Putative Inductive Mechanisms" Department of Microbiology and Immunology, University of North Carolina at Chapel Hill Student Seminar, Apr. 29, 2003, Chapel Hill, NC, Oral Presentation, 22 pages.
Thompson et al. "VEE VRP Mucosal Immunity: Protection from Mucosal Challenge and Putative Inductive Mechanisms" University of North Carolina at Chapel Hill, Virology in Progress Series, Mar. 21, 2003, Chapel Hill, NC, Oral Presentation, 18 pages.
Tsiang et al. "Effects of 5'-Terminal Modifications on the Biological Activity of Defective Interfering RNAs of Sindbis Virus" *Journal of Virology* 62(1):47-53 (Jan. 1988).
Vajdy et al. "Human Immunodeficiency Virus Type 1 Gag-Specific Vaginal Immunity and Protection After Local Immunizations with Sindbis Virus-Based Replicon Particles" *The Journal of Infectious Diseases* 184:1613-1616 (2001).
Vennema et al. "Early Death after Feline Infectious Peritonitis Virus Challenge due to Recombinant Vaccinia Virus Immunization" *Journal of Virology* 64(3):1407-1409 (1990).
Vrati et al. "Ross River Virus Mutant with a Deletion in the E2 Gene: Properties of the Virion, Virus-Specific Macromolecule Synthesis, and Attenuation of Virulence for Mice" *Virology* 151:222-232 (1986).
Walton et al. "Cross-Protective immunity between equine encephalomyelitis viruses in equids" *Am J Vet Res* 50(9):1442-1446 (1989).
Wang et al. "Active Immunotherapy of Cancer with a Nonreplicating Recombinant Fowlpox Virus Encoding a Model Tumor Associated Antigen" *The Journal of Immunology* 154:4685-4692 (1995).
Weiss et al. "Recombination Between Sindbis Virus RNAs" *Journal of Virology* 65(8):4017-4025 (1991).
West et al. "Genetic Analysis of Cell Targeting and Immunogenicity of VEE Vectors" (Abstract) AIDS Vaccine 2001 Meeting Philadelphia, PA (Sep. 2001).
Wu et al. "Tolerance to a Dominant T Cell Epitope in the Acetylcholine Receptor Molecule Induces Epitope Spread and Suppresses Murine Myasthenia Gravis" *The Journal of Immunology* 159(6):3016-3023 (1997).
Xiong et al. "Sindbis Virus: An Efficient, Broad Host Range Vector for Gene Expression in Animal Cells" *Science* 243(4895):1188-1191 (1989).
Yao et al. "Antibody-dependent enhancement of hantavirus infection in macrophage cell lines," *Archives of Virology* 122:107-118 (1992).
Extended European Search Report for EP Application No. 05857516. 8, mailed Dec. 17, 2009.
Burkhard et al., "Evaluation of FIV protein-expressing VEE replicon vaccine vectors in cats" *Vaccine* 21:258-268 (2002).
Davis et al., "Alphavirus Replicon Particles as Candidate HIV Vaccines" IUBMB *Life* 53:209-211 (2002).
Rayner et al., "Alphavirus vectors and vaccination" *Rev. Med. Virol.* 12:279-296 (2002).
Thompson et al., "Mucosal and systemic adjuvant activity of alphavirus replicon particles" *PNAS* 103(10):3722-3727 (2006).
Thompson et al., "Alphavirus replicon particles acting as adjuvants promote $CD8^+$ T cell responses to co-delivered antigen" *Vaccine* 26:4267-4275 (2008).
Williamson et al., "Characterization and Selection of HIV-1 Subtype C Isolates for Use in Vaccine Development" *AIDS Research and Human Retroviruses* 19(2): 133-144 (2003).

\* cited by examiner

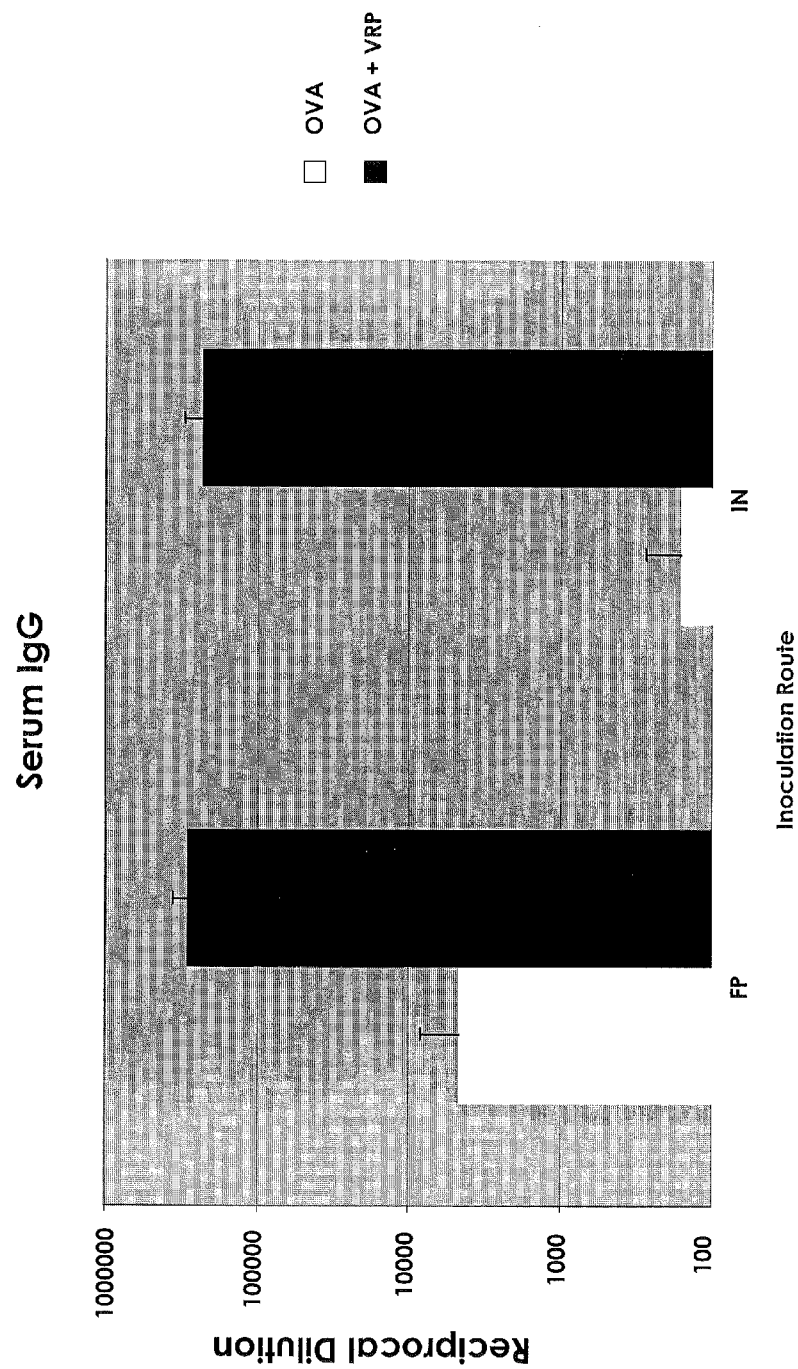
Figure 14A. Systemic Adjuvant Activity of VRP

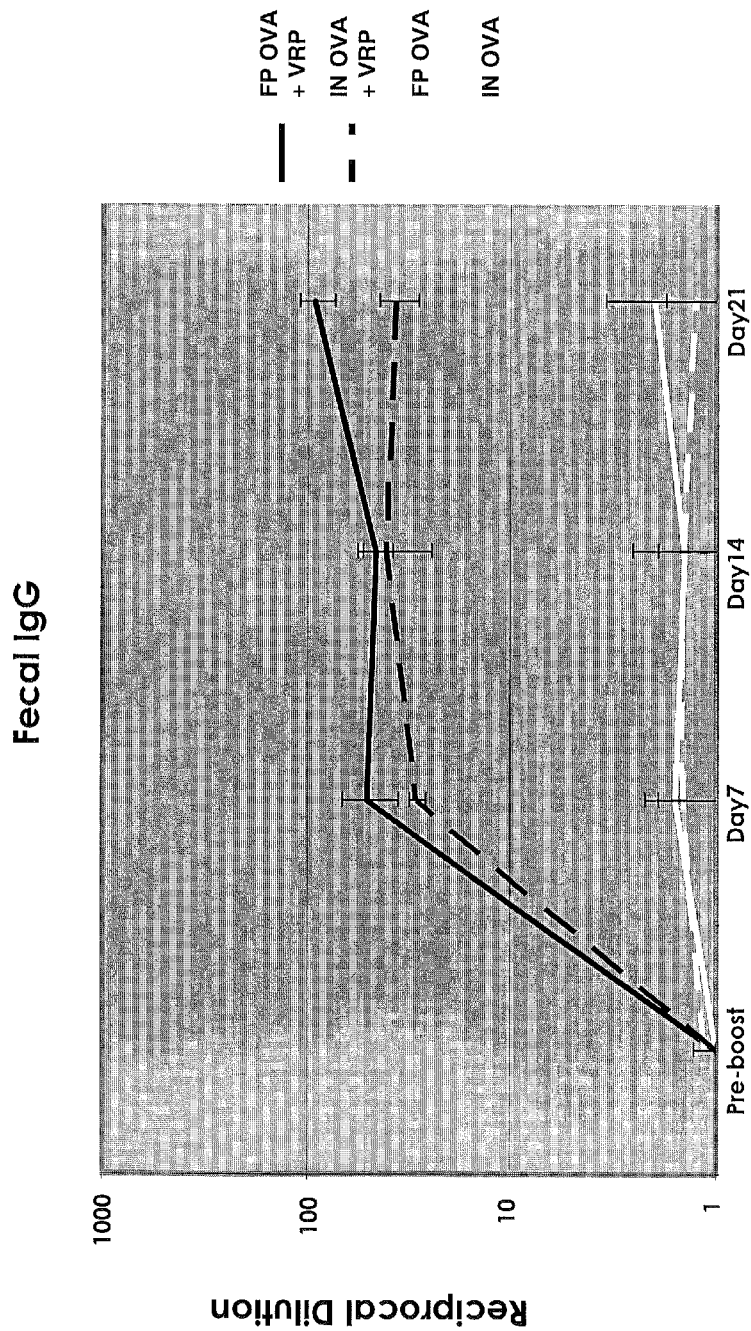
Figure 14B. Mucosal Adjuvant Activity of VRP

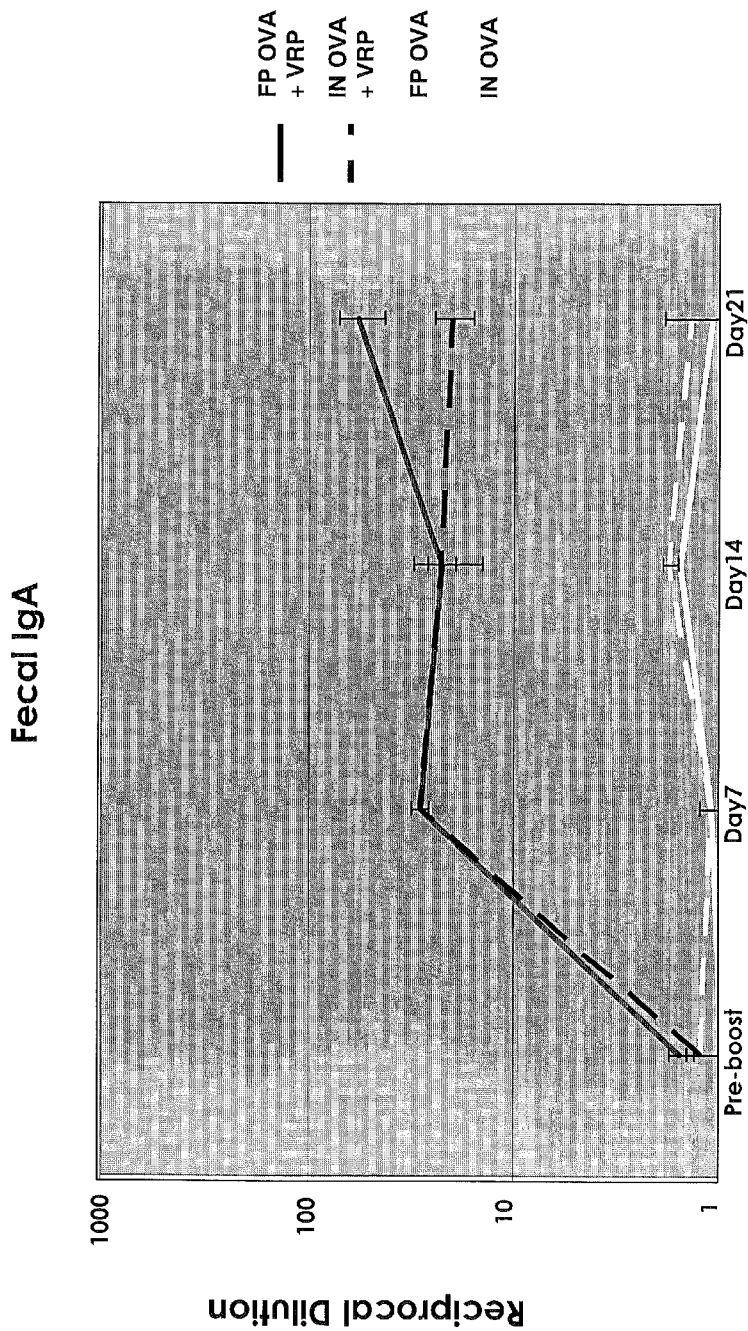
Figure 14C. Mucosal Adjuvant Activity of VRP

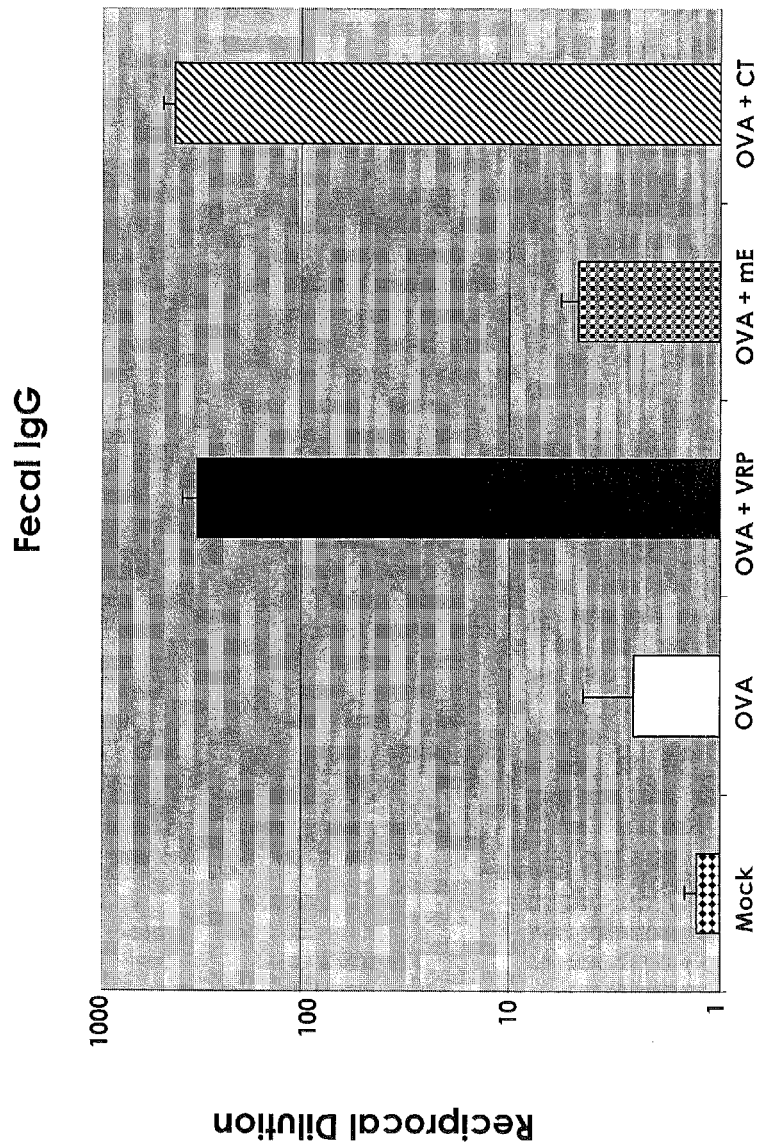

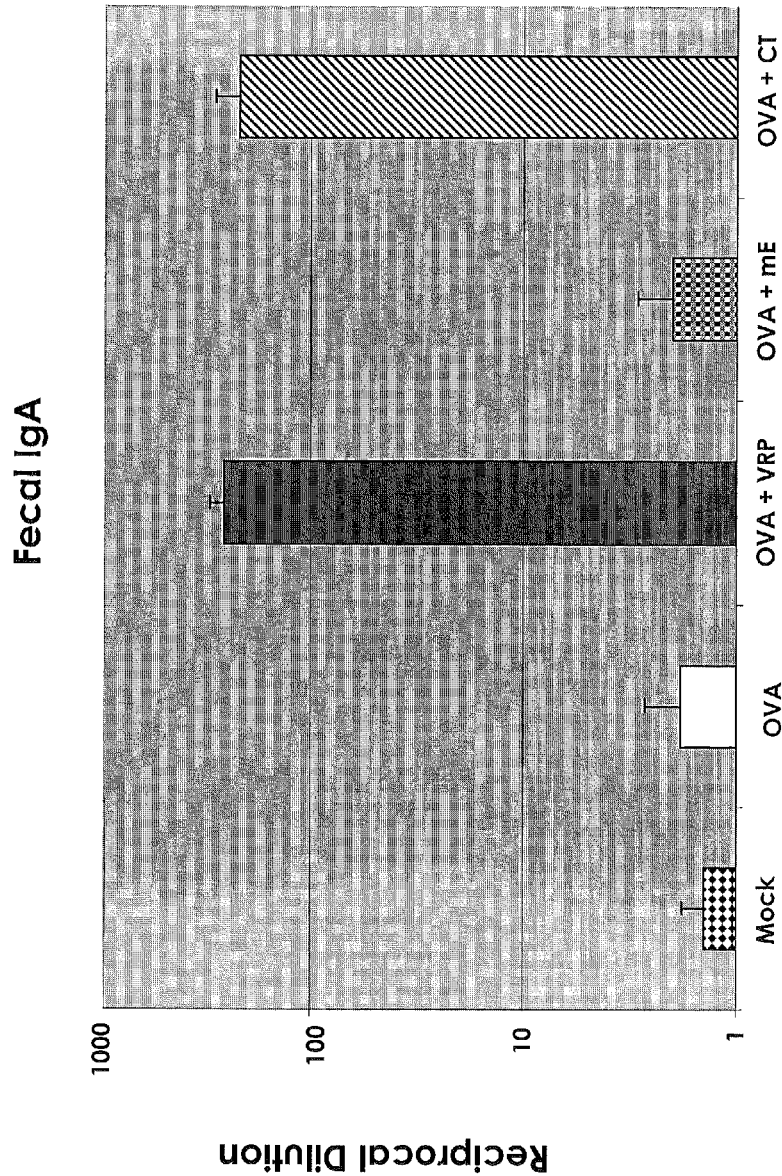

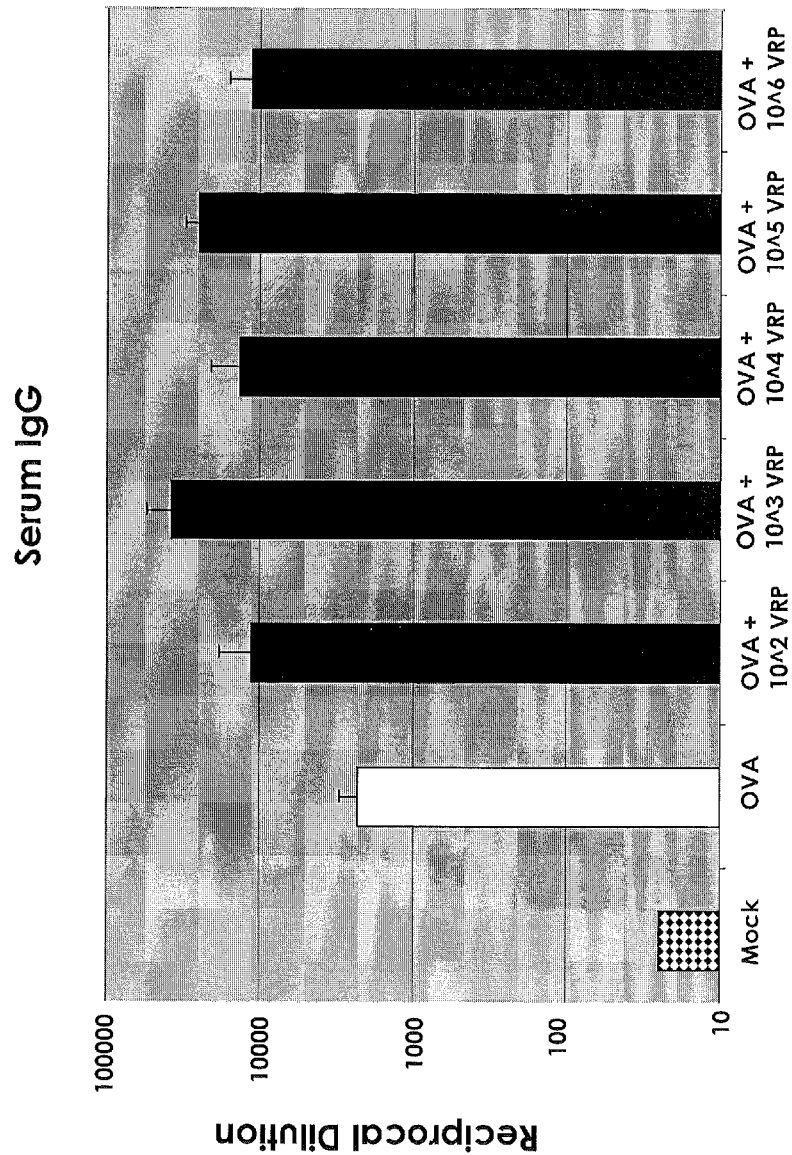
Figure 16. VRP Possess Adjuvant Activity at Low Doses

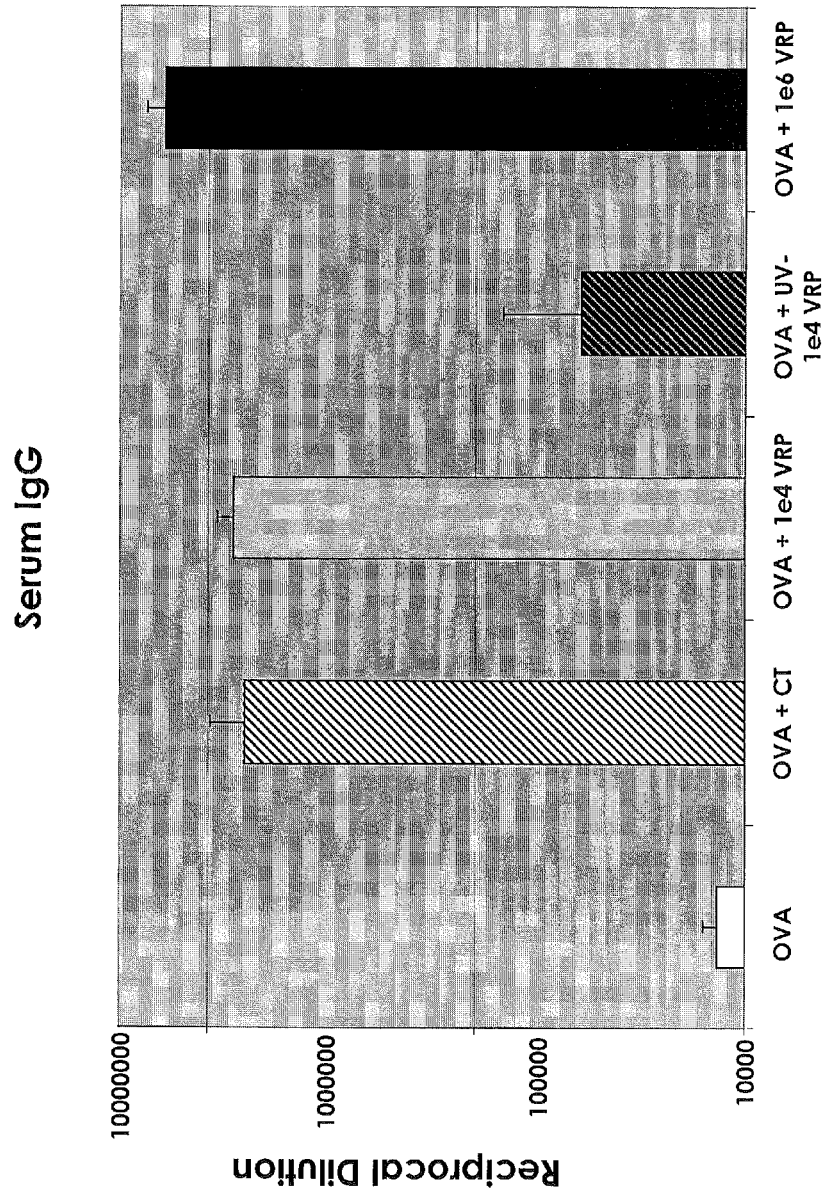

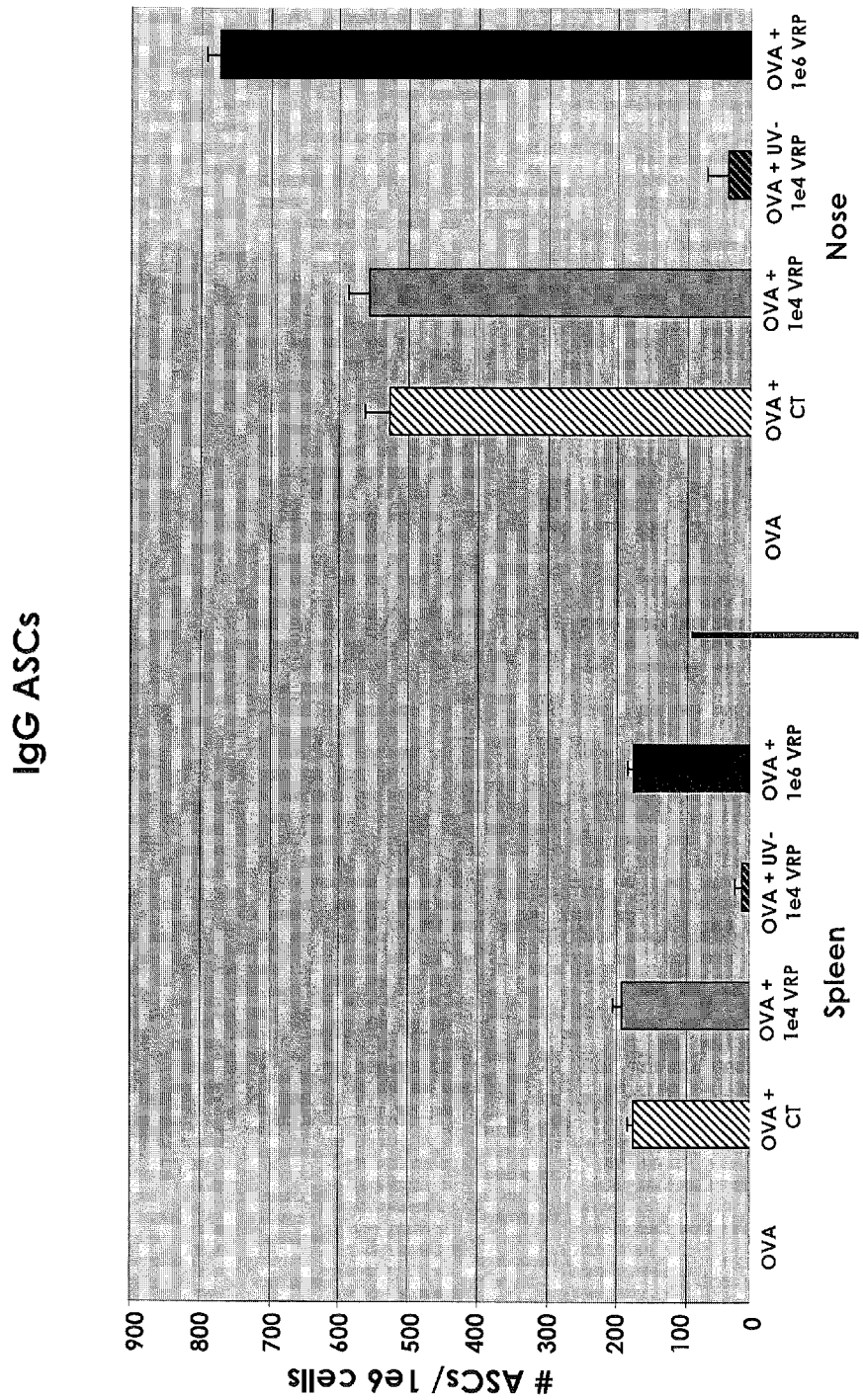

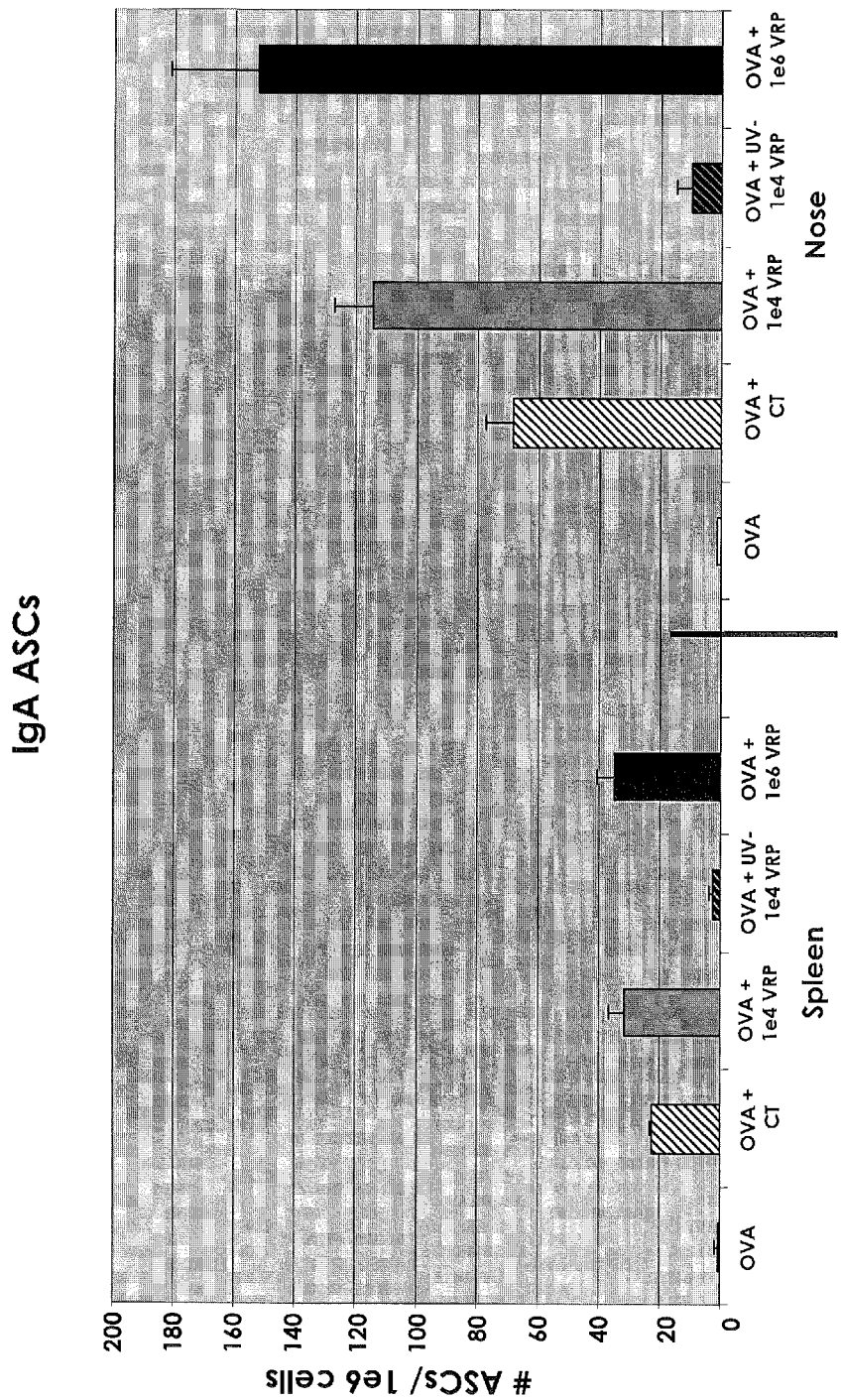

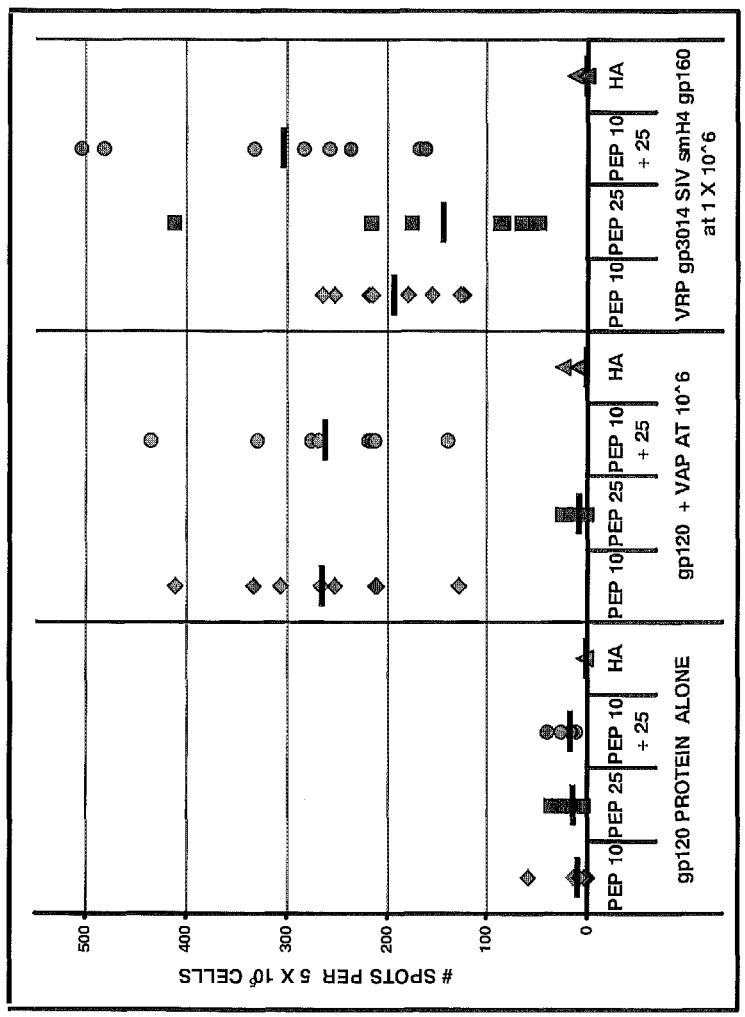
Figure 18. VRP Induction of gp120-specific IFN-g-secreting Cells

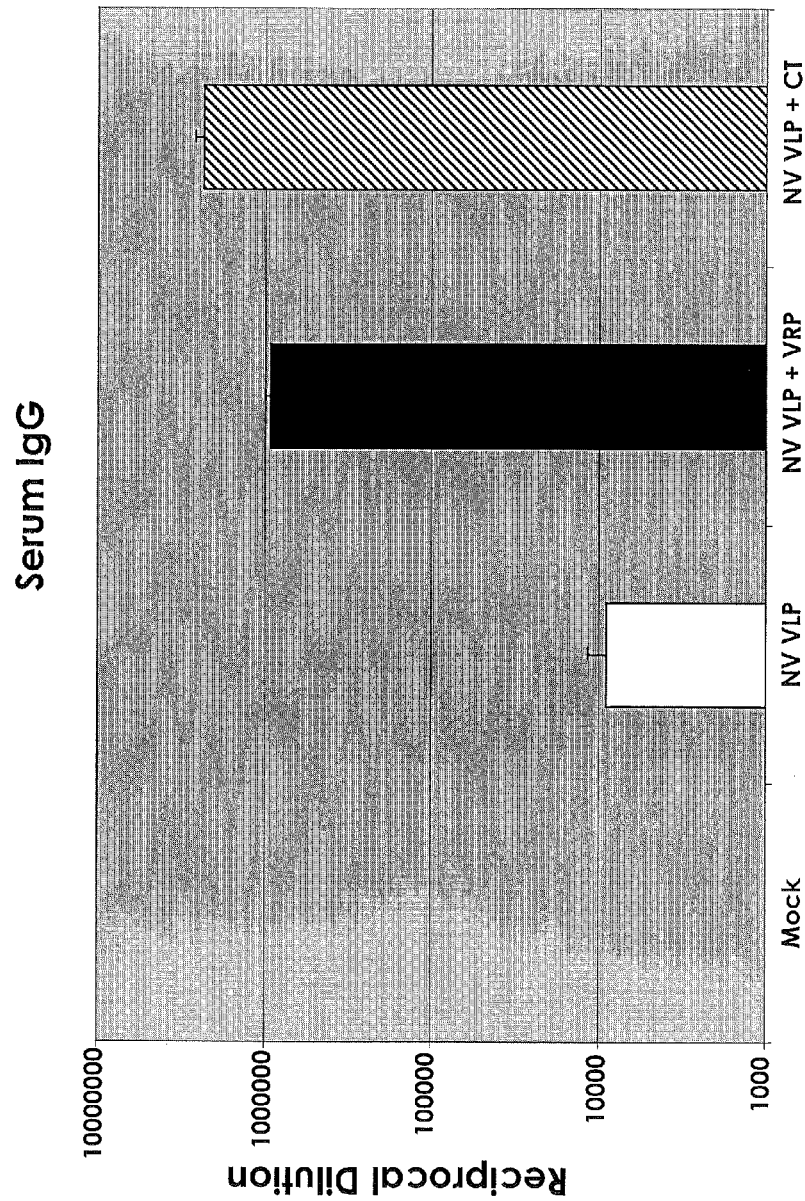

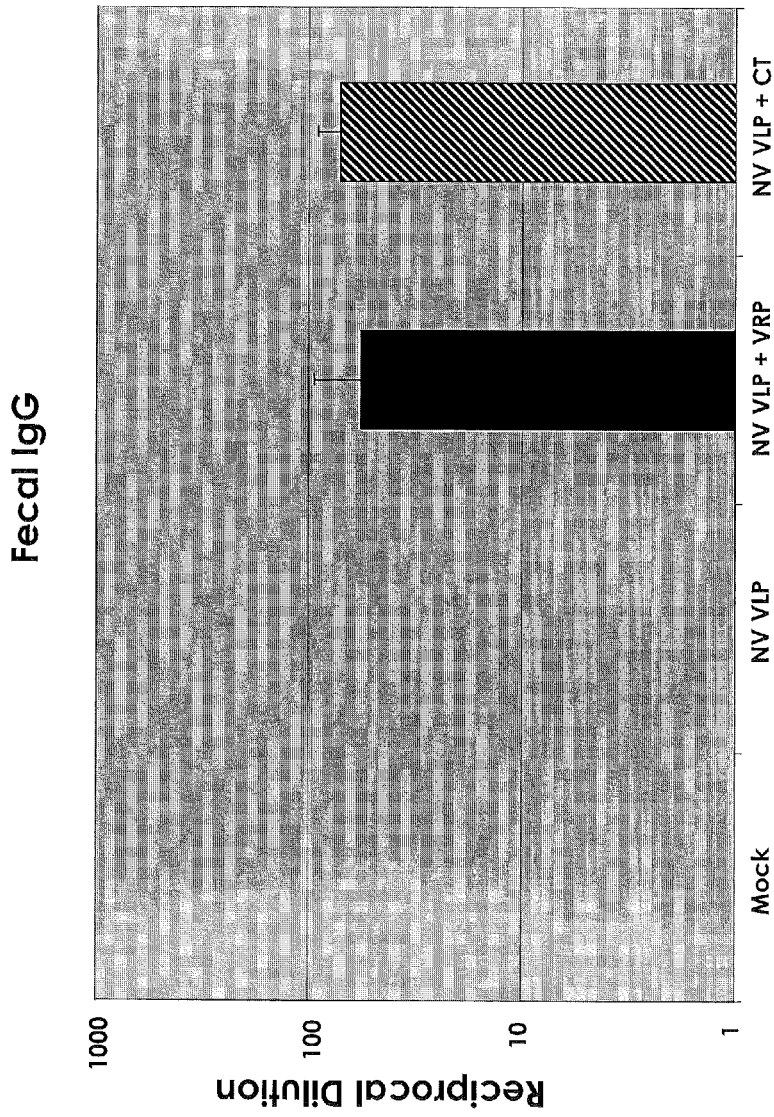
Figure 19B. NV VLP-specific Mucosal Ab production following VRP inoculation

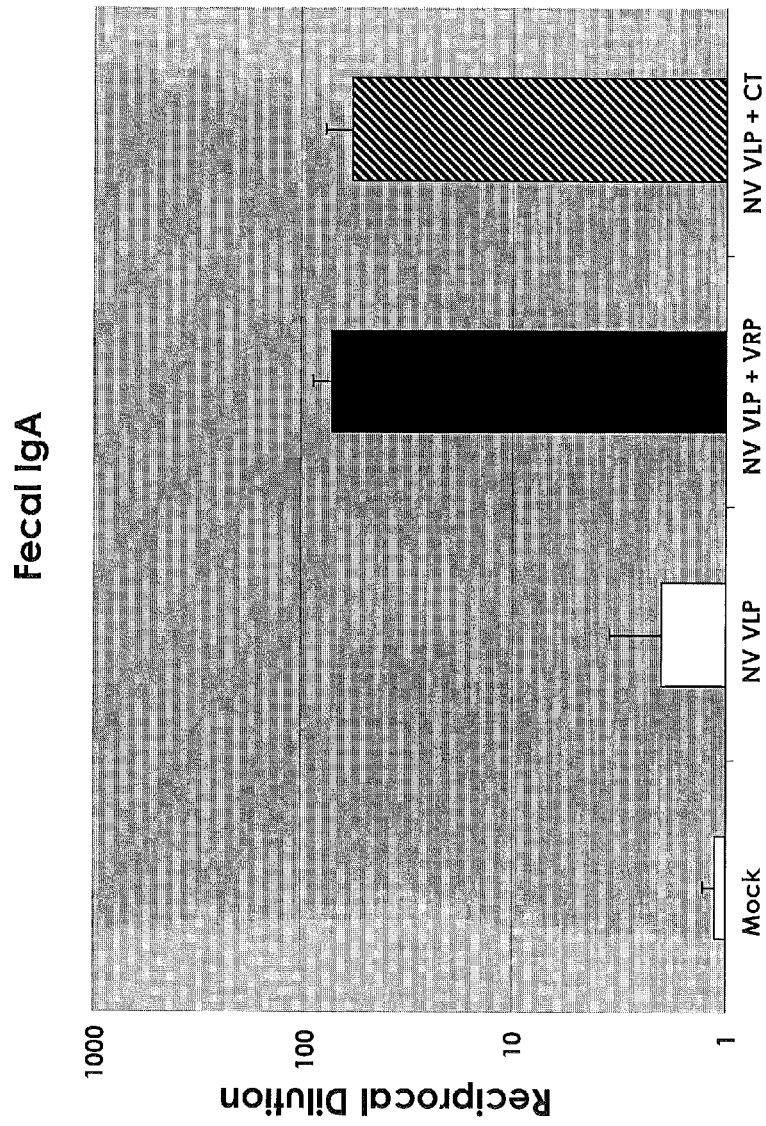
Figure 19C. NV VLP-specific Mucosal Ab production following VRP inoculation

SEQUENCE LISTING

```
<160> NUMBER OF SEQ ID NOS: 1

<210> SEQ ID NO 1
<211> LENGTH: 18
<212> TYPE: PRT
<213> ORGANISM: S.A.AR86 virus

<400> SEQUENCE: 1

Ile Thr Ser Met Asp Ser Trp Ser Ser Gly Pro Ser Ser Leu Glu Ile
1               5                   10                  15

Val Asp
```

VIRAL ADJUVANTS

RELATED APPLICATION INFORMATION

This application is a divisional of U.S. application Ser. No. 11/628,512 and filed Aug. 29, 2007 now U.S. Pat. No. 7,862,829, which claims the benefit under 35 U.S.C. §371 of PCT Application Serial No. PCT/US2005/024424, filed Jul. 8, 2005, which claims the benefit of U.S. provisional application Ser. No. 60/586,881, filed Jul. 9, 2004, the disclosures of which are incorporated herein by reference in their entireties.

STATEMENT OF FEDERAL SUPPORT

This invention was made with government support under grant number 5R01AI51990 from the National Institutes of Health. The United States government has certain rights to this invention.

FIELD OF THE INVENTION

The present invention relates to adjuvants for enhancing immune responses; in particular, the present invention concerns viral adjuvants for achieving enhanced immune responses.

BACKGROUND OF THE INVENTION

Vaccination has long provided the most effective tool in the fight against infectious diseases. Many vaccination regimens exist which allow the manipulation of the type of immune response required for protection from a given pathogen. The use of adjuvants, or compounds co-administered with antigen which augment antigen-specific immune responses, have proven to be extremely beneficial for the induction of protective immunity. Many infectious agents rely on mucosal surfaces for entry into the body. Therefore, adjuvants capable of inducing immune responses and which interfere with the early stages of pathogen entry at mucosal surfaces represent powerful tools in the fight against mucosal infections.

SUMMARY OF THE INVENTION

The present invention is based, in part, on the discovery that virus particles can act as adjuvants or immunostimulatory agents to enhance host immune responses (cellular and/or humoral). It has previously been known that recombinant viruses expressing an immunogen can serve as vaccine vectors to deliver the immunogen to a subject to induce an immune response thereto. In contrast, the inventors have surprisingly found that virus particles (e.g., replicating virus particles) can act as an adjuvant to enhance an immune response against an immunogen that is not presented on or expressed by the virus. The adjuvant can enhance mucosal and/or systemic immune responses.

Accordingly, as a first aspect, the invention provides a method of producing an immune response against an immunogen in a subject, comprising:

(a) administering the immunogen to the subject in an immunogenically effective amount; and (b) administering an alphavirus adjuvant to the subject in an adjuvant effective amount, wherein the alphavirus adjuvant does not express the immunogen.

The invention further provides a method of producing an immune response against an immunogen in a subject, the method comprising:

(a) administering the immunogen to the subject in an immunogenically effective amount; and (b) administering a propagation-defective Venezuelan Equine Encephalitis (VEE) viral adjuvant to the subject in an adjuvant effective amount, wherein the VEE viral adjuvant does not express the immunogen.

As a further aspect, the invention provides an alphavirus adjuvant comprising:

a modified alphavirus genomic nucleic acid that lacks sequences encoding the alphavirus structural proteins required for production of new alphavirus particles; wherein the modified alphavirus genome does not comprise a heterologous nucleic acid sequence that encodes a polypeptide of interest or a functional untranslated RNA.

In particular embodiments, the alphavirus adjuvant is self-replicating. (i.e., the modified alphavirus genomic nucleic acid comprises sufficient coding nsP1 to nsP4 gene sequences for the genomic nucleic acid to replicate).

In other embodiments, the alphavirus adjuvant comprises a propagation-defective alphavirus particle that further comprises an alphavirus virion coat that packages the modified alphavirus genomic nucleic acid.

In particular embodiments, the viral adjuvant is a VEE virus adjuvant in which the viral adjuvant comprises a virion coat comprising VEE structural proteins and/or the viral adjuvant comprises a modified VEE genomic nucleic acid. Optionally, the VEE virus adjuvant is self-replicating.

According to other embodiments, the modified alphavirus genomic nucleic acid is a modified VEE viral genomic nucleic acid.

In still other embodiments, the alphavirus adjuvant comprises a propagation-defective VEE particle that further comprises a VEE virion coat that packages the modified alphavirus genomic nucleic acid (e.g., a modified VEE genomic nucleic acid).

As a further aspect, the invention also provides compositions comprising the inventive viral adjuvants, and optionally an immunogen, and pharmaceutical formulations comprising the viral adjuvants or compositions of the invention.

As yet another aspect, the present invention provides a helper cell for producing an alphavirus adjuvant comprising an infectious propagation-defective alphavirus particle, comprising in an alphavirus-permissive cell:

(a) a modified alphavirus genomic RNA that comprises (i) sequences encoding the alphavirus nonstructural proteins, and (ii) a competent alphavirus packaging sequence, and (iii) wherein the modified alphavirus genomic nucleic acid lacks sequences encoding the alphavirus structural proteins required for production of new alphavirus particles; and further wherein the modified alphavirus genomic nucleic acid does not comprise a heterologous nucleic acid sequence that encodes a polypeptide of interest or a functional untranslated RNA;

(b) sequences encoding the alphavirus structural proteins sufficient for producing an alphavirus particle;

wherein the combined expression of the modified alphavirus genomic RNA and the sequences encoding the alphavirus structural proteins produces an assembled alphavirus particle comprising the modified alphavirus genomic RNA. In particular embodiments, the helper nucleic acid(s) are RNA molecules, which are optionally transfected into the helper cell.

As still a further aspect, the invention provides a method of making an alphavirus adjuvant comprising infectious propagation-defective alphavirus particles, comprising:

(a) providing a helper cell according to the invention;
(b) producing the alphavirus particles in the helper cell; and
(c) collecting the alphavirus particles from the helper cell.

In particular embodiments, the viral adjuvant is a virus particle (including a live virus, an attenuated live virus, an inactivated virus), a virus-like particle (i.e., a virion coat without genomic nucleic acid), a modified viral genomic nucleic acid (e.g., a replicating genomic nucleic acid), or an unassembled viral structural protein(s) (e.g., alphavirus E1, E2 and/or capsid proteins, optionally in a liposomal delivery vehicle), or a nucleic acid encoding any of the foregoing. In some embodiments, the invention is practiced to enhance the immune response to an attenuated live virus, a killed vaccine, a DNA vaccine, or a subunit protein or peptide vaccine, all of which can have the disadvantage of reduced immunogenicity. Optionally, the viral adjuvant is a replicating entity.

As another aspect, the invention provides for the use of a viral adjuvant for increasing the immune response against an immunogen. Also encompassed by the invention is the use of a virus for the preparation of an adjuvant formulation. The invention further provides the use of a viral adjuvant for the preparation of a medicament.

In addition, the invention provides methods of administering viral particle adjuvants to induce a mucosal response against the virus particles, against an immunogen expressed by the virus particle, and/or against an immunogen that is administered to the subject but is not expressed by the virus particle. The virus particle adjuvant can be administered mucosally or non-mucosally.

These and other aspects of the invention are discussed in more detail in the detailed description of the invention set forth below.

BRIEF DESCRIPTION OF THE DRAWINGS

FIG. 14A. Ovalbumin (OVA)-specific antibody (Ab) production following VRP inoculation. Groups of eight Balb/c animals were vaccinated and boosted four weeks later with 10 μg of Ovalbumin (OVA), or 10 μg OVA co-inoculated with $1 \times 10^6$ infectious units (I.U.) of empty (not expressing any antigen) VRP, either in the footpad (FP) or intranasal (IN). Three weeks post boost, animals were bled and sera analyzed for the presence of OVA-specific IgG antibodies via ELISA. Antibody titers are presented as the reciprocal dilution which results in an optical density (OD)>0.2.

FIG. 14B. Ovalbumin (OVA)-specific antibody (Ab) production following VRP inoculation. Groups of eight Balb/c animals were vaccinated and boosted four weeks later with 10 μ of Ovalbumin (OVA), or 10 μg OVA co-inoculated with $1 \times 10^6$ infectious units (I.U.) of empty (not expressing any antigen) VRP, either in the footpad (FP) or intranasal (IN). Three weeks post boost, fecal extracts were prepared from immunized animals and analyzed for the presence of OVA-specific IgG antibodies via ELISA. Antibody titers are presented as the reciprocal dilution which results in an optical density (OD)>0.2.

FIG. 14C. Ovalbumin (OVA)-specific antibody (Ab) production following VRP inoculation. Groups of eight Balb/c animals were vaccinated and boosted four weeks later with 10

Figure 1:
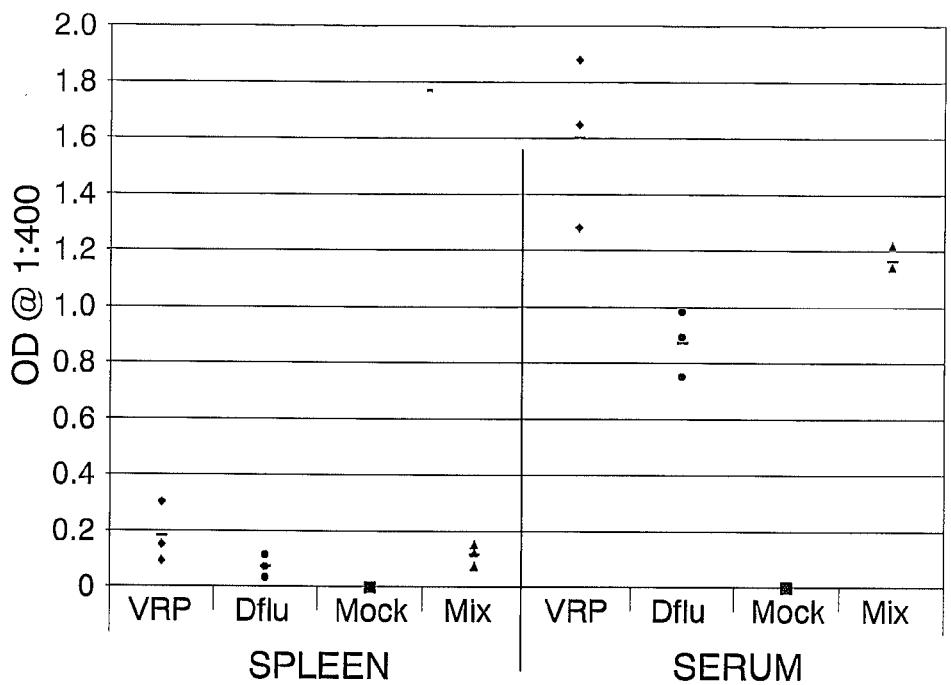
FIG. 1 shows optical density (OD) measurements of an ELISA (1:400 dilution) for IgG production by lymphoid cultures of non-mucosal tissue (spleen and serum) from mice mock-inoculated or inoculated with virus replicon particles expressing hemagglutinin (VRP), formalin-inactivated influenza virus (dflu), or a co-inoculation thereof (mix).

μg of Ovalbumin (OVA), or 10 μg OVA co-inoculated with 1×10⁶ infectious units (I.U.) of empty (not expressing any antigen) VRP, either in the footpad (FP) or intranasal (IN). Three weeks post boost, fecal extracts were prepared from immunized animals and analyzed for the presence of OVA-specific IgA antibodies via ELISA. Antibody titers are presented as the reciprocal dilution which results in an optical density (OD)>0.2.

FIG. 15A. Ovalbumin (OVA)-specific antibody (Ab) production following VRP inoculation. Groups of eight Balb/c animals were vaccinated and boosted four weeks later in the footpad with PBS, 10 μg of Ovalbumin (OVA), 10 μg OVA co-inoculated with 1×10⁶ infectious units (I.U.) of empty (not expressing any antigen) VRP, 10 μg OVA co-inoculated with an equivalent dilution of the supernatant from a mock electroporation (mE), 10 μg OVA co-inoculated with 1 μg of cholera toxin (CT), or 10 μg of OVA co-inoculated with 1×10⁶ I.U. UV-treated empty VRP. Three weeks post boost, fecal extracts were prepared from immunized animals and analyzed for the presence of OVA-specific IgG antibodies via ELISA. Antibody titers are presented as the reciprocal dilution which results in an optical density (OD)>0.2.

FIG. 15B. OVA-specific antibody (Ab) production following VRP inoculation. Groups of eight Balb/c animals were vaccinated and boosted four weeks later in the footpad with PBS, 10 μg of Ovalbumin (OVA), 10 μg OVA co-inoculated with 1×10⁶ infectious units (I.U.) of empty (not expressing any antigen) VRP, 10 μg OVA co-inoculated with an equivalent dilution of the supernatant from a mock electroporation (mE), 10 μg OVA co-inoculated with 1 μg of cholera toxin (CT), or 10 μg of OVA co-inoculated with 1×10⁶ I.U. UV-treated empty VRP. Three weeks post boost, fecal extracts were prepared from immunized animals and analyzed for the presence of OVA-specific IgG antibodies via ELISA. Antibody titers are presented as the reciprocal dilution which results in an optical density (OD)>0.2.

FIG. 16. Ovalbumin (OVA)-specific antibody (Ab) production following VRP inoculation. Groups of eight Balb/c animals were vaccinated and boosted four weeks later in the footpad with PBS, 10 μg of Ovalbumin (OVA), 10 μg OVA co-inoculated with 1×10² infectious units (I.U.) of empty (not expressing any antigen) VRP, 1×10³ I.U. VRP, 1×10⁴ I.U. VRP, 1×10⁵ I.U. VRP, 1×10⁶ I.U. VRP. Three weeks post boost, animals were bleed and sera analyzed for the presence of OVA-specific IgG antibodies via ELISA. Antibody titers are presented as the reciprocal dilution which results in an optical density (OD)>0.2.

FIG. 17A. Ovalbumin (OVA)-specific antibody (Ab) production following VRP inoculation. Groups of six Balb/c animals were vaccinated and boosted four weeks later in the footpad with 10 μg of Ovalbumin (OVA), 10μ OVA co-inoculated with 1 μg of cholera toxin (CT), 10 μg OVA co-inoculated with 1×10⁴ infectious units (I.U.) of empty (not expressing any antigen) VRP, 10 μg OVA co-inoculated with 1×10⁴ I.U. empty VRP treated with ultraviolet (UV) light, or 10 μg of OVA co-inoculated with 1×10⁶ I.U. empty VRP. One week post boost, serum was harvested from immunized animals and analyzed for the presence of OVA-specific IgG antibodies via ELISA.

FIG. 17B. Ovalbumin (OVA)-specific antibody (Ab) production following VRP inoculation. Groups of six Balb/c animals were vaccinated and boosted four weeks later in the footpad with 10 μg of Ovalbumin (OVA), 10 μg OVA co-inoculated with 1 μg of cholera toxin (CT), 10 μg OVA co-inoculated with 1×10⁴ infectious units (I.U.) of empty (not expressing any antigen) VRP, 10 μg OVA co-inoculated with 1×10⁴ I.U. empty VRP treated with ultraviolet (UV) light, or 10 μg of OVA co-inoculated with 1×10⁶ I.U. empty VRP. One week post boost, single cell suspensions were harvested from spleen and nasal epithelium and assayed for the presence of OVA-specific IgG.

FIG. 17C. Ovalbumin (OVA)-specific antibody (Ab) production following VRP inoculation. Groups of six Balb/c animals were vaccinated and boosted four weeks later in the footpad with 10 μg of Ovalbumin (OVA), 10 μg OVA co-inoculated with 1 μg of cholera toxin (CT), 10 μg OVA co-inoculated with 1×10⁴ infectious units (I.U.) of empty (not expressing any antigen) VRP, 10 μg OVA co-inoculated with 1×10⁴ I.U. empty VRP treated with ultraviolet (UV) light, or 10 μg of OVA co-inoculated with 1×10⁶ I.U. empty VRP. One week post boost, single cell suspensions were harvested from spleen and nasal epithelium and assayed for the presence of OVA-specific ASCs via ELISPOT.

FIG. 18. VRP induction of gp120-specific IFN-g-secreting cells. Groups of eight Balb/c animals were vaccinated and boosted four weeks later with PBS, 10 μg of SIV gp120 protein, 10 μg of gp120 co-inoculated with 1×10⁶ infectious units (I.U.) of empty (not expressing any antigen) VRP, or 1×10⁶ I.U. of VRP expressing full length SIV gp160. One week post boost, animals were sacrificed and spleens were isolated from immunized animals. Single cell suspensions were prepared from isolated spleens and analyzed for the presence of IFN-γ-secreting cells via IFN-γ ELISPOT following in vitro stimulation with either gp120 peptides or an irrelevant HA peptide. Numbers of IFN-γ-secreting cells are displayed per 5×10⁵ cells.

FIG. 19A. Norwalk Virus (NV) VLP-specific antibody (Ab) production following VRP inoculation. Groups of six Balb/c animals were vaccinated and boosted four weeks later with PBS, 10 μg of Norwalk virus (NV) virus-like particles (VLP), 10 μg NV VLP co-inoculated with 1×10⁶ infectious units (I.U.) of empty (not expressing any antigen) VRP, or 10 μg NV VLP co-inoculated with 1 μg of cholera toxin (CT). Three weeks post boost, fecal extracts were prepared from immunized animals and analyzed for the presence of OVA-specific IgG antibodies via ELISA. Antibody titers are presented as the reciprocal dilution which results in an optical density (OD)>0.2.

FIG. 19B. Norwalk Virus (NV) VLP-specific antibody (Ab) production following VRP inoculation. Groups of six Balb/c animals were vaccinated and boosted four weeks later with PBS, 10 μg of Norwalk virus (NV) virus-like particles (VLP), 10 μg NV VLP co-inoculated with 1×10⁶ infectious units (I.U.) of empty (not expressing any antigen) VRP, or 10 μg NV VLP co-inoculated with 1 μg of cholera toxin (CT). Three weeks post boost, fecal extracts were prepared from immunized animals and analyzed for the presence of OVA-specific IgG antibodies via ELISA. Antibody titers are presented as the reciprocal dilution which results in an optical density (OD)>0.2.

FIG. 19C. Norwalk Virus (NV) VLP-specific antibody (Ab) production following VRP inoculation. Groups of six Balb/c animals were vaccinated and boosted four weeks later with PBS, 10 μg of Norwalk virus (NV) virus-like particles (VLP), 10 μg NV VLP co-inoculated with 1×10⁶ infectious units (I.U.) of empty (not expressing any antigen) VRP, or 10 μg NV VLP co-inoculated with 1 μg of cholera toxin (CT). Three weeks post boost, fecal extracts were prepared from immunized animals and analyzed for the presence of OVA-specific IgA antibodies via ELISA. Antibody titers are presented as the reciprocal dilution which results in an optical density (OD)>0.2.

DETAILED DESCRIPTION OF THE INVENTION

The present inventors have made the surprising discovery that virus particles can act as potent adjuvants to enhance an immune response, which effect is unrelated to their ability to act as vaccine vectors. The viral adjuvants of the invention can stimulate and enhance an immune response against an immunogen that is independent of the viral adjuvant, i.e., is not presented by the viral adjuvant or expressed by the viral adjuvant. The inventors have further made the unexpected discovery that administration of the viral adjuvants of the invention by a non-mucosal route can produce a mucosal immune response against an immunogen that is not presented by or expressed by the viral adjuvant.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein or in attachments hereto are incorporated by reference in their entirety.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, the term "adjuvant" has its ordinary meaning as understood by those in the art. For example, an adjuvant can be defined as a substance that increases the ability of an immunogen (i.e., antigen) to stimulate an immune response against the immunogen in the subject. In particular embodiments, the adjuvant increases the immune response against the immunogen by at least about 2, 3, 4, 5, 10, 15, 20, 30, 40, 50, 60, 75, 100, 150, 500, 1000-fold or more. In other embodiments, the adjuvant reduces the amount of immunogen required to achieve a particular level of immune response (cellular and/or humoral and/or mucosal), e.g., a reduction of at least about 15%, 25%, 35%, 50%, 65%, 75%, 80%, 85%, 90%, 95%, 98% or more. An adjuvant can further be a substance that prolongs the time over which an immune response, optionally protective immune response, is sustained (e.g., by at least about a 2-fold, 3-fold, 5-fold, 10-fold, 20-fold longer time period or more).

By "mucosal immune response" it is meant an immune response (cellular and/or humoral) that is detectable and resident at a mucosal surface(s) of the host (e.g., the respiratory tract, the reproductive tract, the urinary tract, the gastrointestinal tract). Typically, but not necessarily, a mucosal immune response is accompanied by production of antigen-specific IgA molecules.

By "systemic immune response" it is meant an immune response (cellular and/or humoral) that is detectable in blood and/or lymphoid tissue (e.g., spleen and lymph nodes).

As used herein, the term "polypeptide" encompasses both peptides and proteins.

A "polypeptide of interest" as used herein is a polypeptide that is desirably introduced and/or expressed in a subject, e.g., because of its biological and/or antigenic properties and includes reporter polypeptides, therapeutic polypeptides, enzymes, growth factors, immunomodulatory polypeptides, and immunogenic polypeptides.

As used herein, an "isolated" nucleic acid means a nucleic acid separated or substantially free from at least some of the other components of the naturally occurring organism or virus, for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

The term "nucleic acid" as used herein encompasses both RNA and DNA, including cDNA, genomic DNA, synthetic (e.g., chemically synthesized) DNA and chimeras of RNA and DNA. The nucleic acid may be double-stranded or single-stranded. Where single-stranded, the nucleic acid may be a sense strand or an antisense strand. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "heterologous nucleic acid" is a well-known term of art and would be readily understood by one of skill in the art to be a nucleic acid that is foreign to the nucleic acid carrier (e.g., viral or plasmid delivery vector).

A "functional untranslated RNA" includes, for example, interfering RNA (e.g., siRNA) or antisense RNA.

The heterologous nucleic acid can be associated with appropriate expression control sequences, e.g., transcription/translation control signals and polyadenylation signals.

It will be appreciated that a variety of promoter/enhancer elements can be used depending on the level and tissue-specific expression desired. The promoter can be constitutive or inducible (e.g., the metallothionein promoter or a hormone inducible promoter), depending on the pattern of expression desired. The promoter can be native or foreign and can be a natural or a synthetic sequence. By foreign, it is intended that the promoter is not found in the virus into which the promoter is introduced. The promoter is generally chosen so that it will function in the target cell(s) of interest. In particular embodiments, the heterologous nucleotide sequence is operably associated with a promoter that provides high level expression of the heterologous nucleotide sequence, e.g., an alphavirus subgenomic 26S promoter (preferably, a VEE, Sindbis, Girdwood or TR339 26S subgenomic promoter).

Inducible expression control elements can be used in those applications in which it is desirable to provide regulation over expression of the heterologous nucleic acid sequence. Inducible promoters/enhancer elements include tissue-specific promoter/enhancer elements, which further includes, but is not limited to, muscle specific (including cardiac, skeletal and/or smooth muscle), neural tissue specific (including brain-specific), eye (including retina-specific and cornea-specific), liver specific, bone marrow specific, pancreatic specific, spleen specific, and lung specific promoter/enhancer elements. Other inducible promoter/enhancer elements include hormone-inducible and metal-inducible elements, examples of which include but are not limited to a Tet on/off element, a RU486-inducible promoter, an ecdysone-inducible promoter, a rapamycin-inducible promoter, and a metallothionein promoter.

Moreover, specific initiation signals are generally required for efficient translation of inserted polypeptide coding sequences. These translational control sequences, which can include the ATG initiation codon and adjacent sequences, can be of a variety of origins, both natural and synthetic. In embodiments of the invention wherein there are two or more heterologous nucleic acids to be transcribed, the transcriptional units can be operatively associated with separate promoters or with a single upstream promoter and one or more downstream internal ribosome entry site (IRES) sequences (e.g., the picornavirus EMC IRES sequence).

In embodiments of the invention in which the heterologous nucleic acid sequence is transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

As used herein, the terms "express," "expresses," "expressed" or "expression," and the like, with respect to a nucleic acid sequence (e.g., RNA or DNA) indicates that the nucleic acid sequence is transcribed and, optionally, translated. Thus, a nucleic acid sequence may express a polypeptide of interest or a functional untranslated RNA.

By the terms "treat," "treats," "treating" or "treatment of," and the like, it is intended that the severity of the patient's condition is reduced or at least partially improved or modified and that some alleviation, mitigation or decrease in at least one clinical symptom is achieved. The terms "treat," "treats," "treating," or "treatment" of also include prophylactic treatment of the subject to prevent the onset of infection, cancer, transplant rejection, or other symptoms. As used herein, the terms "prevent," "prevents," and "prevention" (and grammatical equivalents thereof) are not meant to imply complete abolition of infection, cancer, transplant rejection or other symptoms and encompasses any type of prophylactic treatment that reduces the incidence of the condition, delays the onset and/or progression of the condition, and/or reduces the symptoms associated with the condition.

Alphavirus particles comprise the alphavirus structural proteins assembled to form an enveloped nucleocapsid structure. As known in the art, alphavirus structural subunits consisting of a single viral protein, capsid, associate with themselves and with the RNA genome to form the icosahedral nucleocapsid, which is then surrounded by a lipid envelope covered with a regular array of transmembranal protein spikes, each of which consists of a heterodimeric complex of two glycoproteins, E1 and E2 (See Paredes et al., (1993) *Proc. Natl. Acad. Sci. USA* 90, 9095-99; Paredes et al., (1993) *Virology* 187, 324-32; Pedersen et al., (1974) *J. Virol.* 14:40). The wild-type alphavirus genome is a single-stranded, messenger-sense RNA, modified at the 5'-end with a methylated cap, and at the 3'-end with a variable-length poly (A) tract. The viral genome is divided into two regions: the first encodes the nonstructural or replicase proteins (nsP1-nsP4) and the second encodes the viral structural proteins (Strauss and Strauss, *Microbiological Rev.* (1994) 58:491-562).

The term "alphavirus" has its conventional meaning in the art, and includes Eastern Equine Encephalitis virus (EEE), Venezuelan Equine Encephalitis virus (VEE), Everglades virus, Mucambo virus, Pixuna virus, Western Encephalitis virus (WEE), Sindbis virus, South African Arbovirus No. 86 (S.A.AR86), Girdwood S.A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzlagach virus, Highlands J virus, Fort Morgan virus, Ndumu virus, Buggy Creek virus, and any other virus classified by the International Committee on Taxonomy of Viruses (ICTV) as an alphavirus.

Preferred alphaviruses for use in the present invention are Sindbis virus strains (e.g., TR339), VEE, S.A.AR86 virus, Girdwood S.A. virus, and Ockelbo virus, and chimeric viruses thereof. The complete genomic sequences, as well as the sequences of the various structural and non-structural proteins are known in the art for numerous alphaviruses and include without limitation: Sindbis virus genomic sequence (GenBank Accession Nos. J02363, NCBI Accession No. NC_001547), S.A.AR86 genomic sequence (GenBank Accession No. U38305), VEE genomic sequence (GenBank Accession No. L04653, NCBI Accession No. NC_001449), Girdwood S.A genomic sequence (GenBank Accession No. U38304), Semliki Forest virus genomic sequence (GenBank Accession No. X04129, NCBI Accession No. NC_003215), and the TR339 genomic sequence (Klimstra et al., (1988) *J. Virol.* 72:7357; McKnight et al., (1996) *J. Virol.* 70:1981).

The term "flavivirus" has its conventional meaning in the art, and includes tick-borne encephalitis virus, Central European Encephalitis virus, Far Eastern Encephalitis virus, Kunjin virus, Murray Valley Encephalitis virus, St. Louis Encephalitis virus, Rio Bravo virus, Japanese Encephalitis virus, Tyuleniy virus, Ntaya virus, Uganda virus, Dengue virus, Modoc virus, yellow fever virus, West Nile virus, pestiviruses, bovine viral diarrhea virus (including BVDV-1 and BVDV-2), Border disease virus, hepaciviruses, hepatitis C virus, GB virus-A, GB virus-β and GB virus-C and any other virus classified by the International Committee on Taxonomy of Viruses (ICTV) as a flavivirus.

The term "Bunyaviridae" has its conventional meaning in the art, and includes viruses within the genera Bunyavirus, Hantavirus, Nairovirus and Phlebovirus including but not limited to Bunyamwera virus, Rift Valley Fever virus, La Crosse virus and any other virus classified by the International Committee on Taxonomy of Viruses (ICTV) as a bunyavirus. If the adjuvant virus is a bunyavirus, in particular embodiments, the viral adjuvant comprises only one or two of the three viral RNA segments.

The term "rotavirus" has its conventional meaning in the art, and includes Group A, Group B, Group C, Group D, Group E, Group F and Group G rotaviruses and any other virus classified by the International Committee on Taxonomy of Viruses (ICTV) as a rotavirus.

The term "retrovirus" has its conventional meaning in the art, and includes the Alpharetrovirus genus (e.g., Avian leucosis virus and Rous sarcoma virus), Betaretrovirus genus (e.g., Mouse mammary tumor virus, Mason-Pfizer monkey virus, Jaagsiekte sheep retrovirus), Gammaretrovirus genus (e.g., Murine leukemia viruses, Feline leukemia virus, Gibbon ape leukemia virus, reticuloendotheliosis virus), Deltaretrovirus genus (e.g., Human T-lymphotrophic virus, Bovine leukemia virus, Simian T-lymphotrophic virus), Epsilonretrovirus genus (e.g., Walleye dermal sarcoma virus, walleye epidermal hyperplasia virus 1), lentivirus genus (e.g., Human immunodeficiency virus [HIV], including HIV-1 and HIV-2, Simian immunodeficiency virus, Equine infectious anemia virus, Feline immunodeficiency virus, Caprine arthritis encephalitis virus, Visna/maedi virus) and the Spumavirus genus (e.g., Human foamy virus) and any other virus classified by the International Committee on Taxonomy of Viruses (ICTV) as a retrovirus.

The term "orthomyxovirus" has its conventional meaning in the art, and includes influenza A virus, influenza B virus, influenza C virus, thogotovirus and any other virus classified by the International Committee on Taxonomy of Viruses (ICTV) as an orthomyxovirus.

The term "herpesvirus" has its conventional meaning in the art, and includes herpes simplex virus I and herpes simplex virus II and any other virus classified by the International Committee on Taxonomy of Viruses (ICTV) as a herpesvirus.

The term "norovirus" has its conventional meaning in the art, and includes but is not limited to Norwalk virus (including strains Desert Shield virus, Lordsdale virus, Mexico virus, Hawaii virus, Snow Mountain virus, and South Hampton virus) and any other virus classified by the International Committee on Taxonomy of Viruses (ICTV) as a norovirus.

The term "nidovirus" has its conventional meaning in the art and refers to viruses in the Nidovirales order, and includes the family Coronaviridae, which encompasses genera Coronavirus (e.g., avian infectious bronchitis virus, bovine coronavirus, canine coronavirus, feline infectious peritonitis virus, human coronavirus [including strains 229E and OC43], murine hepatitis virus, porcine epidemic diarrhea virus, porcine hemagglutinating encephalomyelitis virus, porcine transmissible gastroenteritis virus, rat coronavirus, turkey coronavirus and rabbit coronavirus) and Torovirus (e.g., equine torovirus [Berne virus], bovine torovirus [Breda virus], human torovirus and porcine torovirus), the family Arteriviridae (e.g., genus Arterivirus including equine arteritis virus, lactate dehydrogenase-elevating virus, porcine respiratory and reproductive syndrome virus, and simian hemorrhagic fever virus) and the family Roniviridae (e.g., genus Okavirus including gill-associated virus and yellow head virus) as well as any other virus classified by the International Committee on Taxonomy of Viruses (ICTV) as a nidovirus.

The term "picornavirus" has its conventional meaning in the art and refers to viruses in the family Picornaviridae and includes viruses in the genera Enterovirus (e.g., bovine enterovirus 1, bovine enterovirus 2, human enterovirus A [human coxsackievirus A 2, 3, 5, 7, 8, 10, 12, 14 and 16 and human enterovirus 71 strains], human enterovirus B [human coxsackievirus A 9 and B 1, 2, 3, 4, 5, 6 strains and human echovirus strains], human enterovirus C virus [human coxsachievirus A 1, 11, 13, 15, 17, 18, 19, 20, 21, 22, 24 strains], human enterovirus D [human enterovirus 68 and 70 strains], human enterovirus E, polioviruses [human poliovirus strains], porcine enterovirus A [porcine enterovirus 8], porcine enterovirus B [porcine enterovirus 9 and 10 strains], and simian enterovirus), Rhinovirus (e.g., human rhinovirus A, human rhinovirus B, and bovine rhinovirus), Cardiovirus (e.g., encephalomyocarditis virus [Mengovirus, Columbia SK virus and Maus Elberfield virus strains], and theilovirus [Theiler's murine encephalomyelitis virus, Vilyuisk human encephalomyelitis virus and rat encephalomyelitis virus]), Aphthovirus (e.g., equine rhinitis A virus and foot-and-mouth disease virus), Hepatovirus (e.g., hepatitis A virus, simian hepatitis A virus, and avian encephalomyelitis-like virus), Parechovirus (e.g., human parechovirus [human parechovirus type 1 strain], human parechovirus type 2, and Ljungan virus), Erbovirus (e.g., equine rhinitis V virus), Kouvirus (e.g., aichi virus) and Teschovirus (e.g., porcine teschovirus 1, porcine teschovirus 2, porcine teschovirus 3, porcine teschovirus 4, porcine teschovirus 5, porcine teschovirus 6, porcine teschovirus 7, porcine teschovirus 8, porcine teschovirus 9, porcine teschovirus 10, porcine teschovirus 1, porcine teschovirus 12, porcine teschovirus 13), acid-stable equine picornaviruses, avian entero-like virus 2, avian entero-like virus 3, avian entero-like virus 4, avian nephritis virus 1, avian nephritis virus 2, avian nephritis virus 3, Barramundi virus-1+, Cockatoo entero-like virus, duck hepatitis virus 1, duck hepatitis virus 3, equine rhinovirus 3, guineafowl transmissible enteritis virus, Harbour seal picorna-like virus, seabass virus-1+, Sikhote-Alyn virus, smelt virus-1+, smelt virus-2+, Syr-Daria valley fever virus, taura syndrome virus of marine penaeid shrimp, turbot virus-1, turkey entero-like virus, turkey pseudo enterovirus 1, and turkey pseudo enterovirus 2, as well as any other virus classified by the International Committee on Taxonomy of Viruses (ICTV) as a picornavirus.

The term "viral structural protein(s)" as used herein refers to one or more of the proteins that are constituents of a functional virus particle. The alphavirus structural proteins include the capsid protein, E1 glycoprotein, E2 glycoprotein, E3 protein and 6K protein. The alphavirus particle comprises the alphavirus structural proteins assembled to form an enveloped nucleocapsid structure. As known in the art, alphavirus structural subunits consisting of a single viral protein, capsid, associate with themselves and with the RNA genome to form the icosahedral nucleocapsid, which is then surrounded by a lipid envelope covered with a regular array of transmembranal protein spikes, each of which consists of a heterodimeric complex of two glycoproteins, E1 and E2 (See Paredes et al., (1993) *Proc. Natl. Acad. Sci. USA* 90, 9095-99; Paredes et al., (1993) *Virology* 187, 324-32; Pedersen et al., (1974) *J. Virol.* 14:40).

A "viral genomic nucleic acid" and similar terms include recombinant and other modified forms (e.g., one or more attenuating mutations, deletions, insertions or otherwise modified viral genomes). The viral genomic nucleic acid can be a propagation-incompetent, but replication-competent, replicon as described herein. An "alphavirus genomic RNA" indicates the alphavirus RNA transcript, including recombinant and other modified forms. The wild-type alphavirus genome is a single-stranded, messenger-sense RNA, modified at the 5'-end with a methylated cap, and at the 3'-end with a variable-length poly (A) tract. The viral genome is divided into two regions: the first encodes the nonstructural or replicase proteins (nsP1-nsP4) and the second encodes the viral structural proteins (Strauss and Strauss, *Microbiological Rev.* (1994) 58:491-562). As used herein, the term "alphavirus genomic RNA" encompasses recombinant alphavirus genomes (e.g., containing a heterologous nucleic acid sequence), viral genomes containing one or more attenuating mutations, deletions, insertions, and/or otherwise modified viral genomes. For example, the "alphavirus genomic RNA" may be modified to form a double-promoter molecule or a replicon (each as described herein). The viral or alphavirus genomic nucleic acid can optionally comprise a packaging signal (e.g., an alphavirus or VEE packaging signal).

A "chimeric" virus as used herein comprises structural proteins from one (or more) viruses and a genomic nucleic acid from another virus. In embodiments of the invention, the chimeric virus is a chimeric alphavirus, e.g., comprising a Sindbis genomic RNA and structural proteins from another alphavirus (e.g., VEE, Girdwood S.A., Ockelbo, and the like). In other embodiments of the invention, the chimeric alphavirus comprises Sindbis alphavirus structural proteins and a genomic RNA from another alphavirus (e.g., VEE, Girdwood S.A., Ockelbo, and the like). Alternatively, a "chimeric virus" comprises structural proteins and/or nucleic acid from two or more viruses, and a "chimeric alphavirus" comprises structural proteins and/or nucleic acid from two or more alphaviruses (e.g., VEE and Sindbis).

An "infectious" virus particle is one that can introduce the virus genomic nucleic acid into a permissive cell, typically by viral transduction. Upon introduction into the target cell, the genomic nucleic acid serves as a template for RNA transcription (i.e., gene expression). The "infectious" alphavirus particle may be "replication-competent" (i.e., can transcribe and replicate the genomic nucleic acid) and "propagation-competent" (i.e., results in a productive infection in which new virus particles are produced). In embodiments of the invention, the "infectious" virus particle is a replicon particle that can introduce the genomic nucleic acid (i.e., replicon) into a host cell, is "replication-competent" to replicate the genomic nucleic acid, but is "propagation-defective" or "propagation-incompetent" in that it is unable to produce new virus particles in the absence of helper sequences that complement the deletions or other mutations in the replicon (i.e., provide the structural proteins that are not provided by the replicon).

A "replicating" or "replication-competent" alphavirus genomic nucleic acid or alphavirus particle refers to the ability to replicate the viral genomic nucleic acid. Generally, a "replication-competent" alphavirus genomic nucleic acid or alphavirus particle will comprise sufficient alphavirus non-structural protein coding sequences (i.e., nsP1 through nsP4 coding sequences) to produce functional alphavirus non-structural proteins.

As used herein, the terms "deleted" or "deletion" mean either total deletion of the specified segment or the deletion of a sufficient portion of the specified segment to render the segment inoperative or nonfunctional, in accordance with standard usage.

I. Viral Adjuvants.

The inventors have made the surprising discovery that viruses (e.g., replicating viruses) can act as potent adjuvants to enhance immune responses independent of their activity as vaccine agents. Thus, the inventive viral adjuvants enhance the immune response of a host (e.g., cellular and/or humoral response) against an immunogen that is independent of (e.g., is not presented by or encoded by) the viral adjuvant. In particular embodiments, the viral adjuvant of the invention enhances mucosal immunity against the immunogen.

The viral adjuvants of the invention can be derived from any suitable virus. In particular embodiments of the invention, the viral adjuvant is an RNA viral adjuvant, i.e., comprises a viral genomic RNA (typically a modified form of a viral genomic RNA) or a DNA molecule that encodes a viral genomic RNA.

The viral adjuvant can be a viral particle adjuvant, which comprises a live, live attenuated, killed and/or chimeric virus particle. Optionally, the viral adjuvant comprises a replicating (i.e., replication-competent) virus particle. In particular embodiments, the viral particle adjuvant is an arbovirus (e.g., a flavivirus, alphavirus or virus in the family Bunyaviridae), a retrovirus, a rotavirus, an orthomyxovirus, a reovirus, a herpesvirus, a nidovirus, a norovirus, and/or a picornavirus. In other embodiments, the viral adjuvant comprises a virus particle (including replicating virus particles) that uses a mucosal surface for viral entry into the host.

Alternatively, the viral adjuvant comprises components derived from any of the foregoing viruses (e.g., structural proteins and/or nucleic acids, including replicating nucleic acids), optionally in a modified form.

In particular embodiments, the viral adjuvant is an alphavirus adjuvant, more particularly a VEE viral adjuvant. By "alphavirus adjuvant" or "VEE viral adjuvant" it is meant that the viral adjuvant comprises (1) a viral coat comprising one, two or more alphavirus or VEE structural proteins, respectively (e.g., E1, E2 and/or capsid), for example, all of the viral structural proteins in the viral coat can be alphavirus or VEE structural proteins (e.g., E1, E2 and capsid), respectively; and/or (2) an alphavirus or VEE genomic RNA (e.g., a replicating alphavirus or VEE genomic RNA), respectively; and/or (3) a DNA that encodes an alphavirus or VEE genomic RNA, respectively. As described above, the alphavirus or VEE genomic RNA encompasses modified genomes. In particular embodiments, the alphavirus adjuvant comprises a replicating alphavirus or VEE virus particle, a replicating viral particle comprising an alphavirus or VEE virion coat, or a replicating viral particle comprising an alphavirus or VEE genomic RNA.

Those skilled in the art will appreciate that an alphavirus adjuvant or VEE adjuvant comprising an alphavirus or VEE virion coat, respectively, can further comprise a viral nucleic acid from another virus, either alphavirus or non-alphavirus. Likewise, an alphavirus adjuvant or VEE adjuvant comprising an alphavirus or VEE genomic RNA, respectively, can further comprise a virion coat from another virus, either alphavirus or non-alphavirus.

The viral adjuvant can comprise a wild-type virus, an attenuated live virus and/or an inactivated (i.e., killed) virus.

As another alternative, the viral adjuvant can comprise a viral genomic nucleic acid or can be a nucleic acid that encodes a nucleic acid derived from viral genomic nucleic acid, for example, as a liposomal formulation. Optionally, the viral nucleic acid is replication-competent.

In some embodiments of the invention, the viral adjuvant comprises structural proteins assembled into a virus-like particle that does not package a genomic nucleic acid or the unassembled viral structural protein(s) (e.g., delivered as a liposomal formulation). To illustrate, the alphavirus E1, E2 glycoproteins and/or the capsid protein, unassembled or assembled as an virus-like particle can be administered, for example, as a liposomal formulation.

In other embodiments, the viral adjuvant can further comprise one or more of the structural proteins (e.g., the alphavirus or VEE E1 and/or E2 glycoproteins) from one of the viruses described above so that the viral adjuvant targets to the same cell(s) as the virus from which the structural protein(s) is derived. In other embodiments, the viral adjuvant comprises a viral nucleic acid (for example, a replicating viral nucleic acid) that is derived from one of the viruses described above. In still other embodiments, the viral adjuvant is a chimeric virus in which the structural proteins and genomic nucleic acid are derived from different viruses (e.g., two different alphaviruses such as Sindbis and VEE).

In some embodiments of the invention, the viral adjuvant is replication-competent (e.g., a replication-competent virus particle or viral nucleic acid).

In particular embodiments, the viral adjuvant is a propagation-defective virus particle that cannot produce new virus particles upon infection of host cells. According to this embodiment, the viral adjuvant can be replication-competent in that it can infect a host cell and replicate and transcribe the viral genome, but cannot produce new virions (e.g., the virus is a replicon particle). Thus, the adjuvant virus comprises nonstructural protein sequences sufficient to provide replicase and transcriptase functions.

In other embodiments, the viral adjuvant is both propagation and replication-incompetent (e.g., an ultraviolet light or chemically inactivated virus).

The viral adjuvant can be propagation-defective because it is defective for expression of (i.e., is unable to produce a functional form of) at least one or all of the viral structural proteins required to assemble new virus particles (e.g., alphavirus E1, E2 and/or capsid proteins). In other words, the viral adjuvant comprises a modified viral genome or a nucleic acid that encodes a modified viral genome that is defective for expression of at least one viral structural protein required for production of new virus particles. For example, one or more of the viral structural protein genes can be inactivated by a mutation and/or by deletion. In representative embodiments, the viral adjuvant cannot produce any of the viral structural proteins. In other particular embodiments, the modified viral genome lacks all or essentially all of the sequences encoding the viral structural proteins.

Additionally or alternatively, in other embodiments, the genomic promoter that drives expression of the viral structural protein genes (e.g., the alphavirus 26S promoter) is inactivated or deleted. To illustrate, the promoter can be inactivated by mutation of cis-acting sequences, for example, by mutagenesis of sequence elements within the promoter region that are required for binding to the RNA polymerase complex. Alternatively or additionally, the viral polymerase can be mutated, e.g., mutation of the viral polymerase encoded by the alphavirus nsP4 gene. Further, specific mutations in the alphavirus nsP1-nsP3 proteins are associated with loss of subgenomic RNA synthesis (while retaining genomic RNA synthesis). Such mutations can be incorporated into the viral adjuvants of the invention to render the viral adjuvant defective for subgenomic RNA synthesis as well as production of new virus particles.

As described above, the viral adjuvant does not necessarily present or express the immunogen, i.e., the immunogen is not presented as part of the virion structure and the genome of the adjuvant virus does not comprise a heterologous nucleic acid sequence that encodes the immunogen.

In particular embodiments, the adjuvant virus expresses a polypeptide of interest including but not limited to another immunogen, a reporter protein (e.g., an enzyme) and/or an immunomodulatory polypeptide such as a cytokine or chemokine (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, lymphotoxin, CCL25 [MECK], and CCL28 [TECH]). Alternatively, the viral adjuvant expresses a functional untranslated RNA.

Reporter proteins are known in the art and include, but are not limited to, Green Fluorescent Protein, β-galactosidase, alkaline phosphatase, chloramphenicol acetyltransferase, and the like.

In some embodiments of the invention, the viral adjuvant comprises a "stuffer" nucleic acid, typically a "spacer" inserted in place of deleted structural protein coding sequences. The stuffer nucleic acid does not encode a polypeptide of interest or functional untranslated RNA, and is inserted into the genome to maintain the size of the genome in the range preferred by the virus (e.g., because of deletion of one or more of the viral structural protein genes). In other embodiments, the viral adjuvant comprises any other nucleic acid that is transcribed and optionally translated, but does not encode the immunogen.

In particular embodiments, the viral adjuvant does not comprise a heterologous nucleic acid that encodes a polypeptide of interest or functional untranslated RNA (i.e., the virus does not express a heterologous or foreign polypeptide of interest or functional untranslated RNA). In other words, the viral adjuvant does not comprise a foreign sequence that encodes a polypeptide of interest or functional untranslated RNA.

In other representative embodiments, the viral adjuvant is an "empty" virus particle or genomic nucleic acid that does not comprise a heterologous nucleic acid sequence (e.g., in place of deleted structural protein coding sequences). Those skilled in the art will appreciate that by "heterologous nucleic acid" it is intended a nucleic acid that is foreign or exogenous to the virus and which is transcribed, and optionally translated, to produce a polypeptide of interest or functional untranslated RNA of interest or a "stuffer" nucleic acid as described above. Thus, it will further be recognized by those skilled in the art that the phrase "does not comprise a heterologous nucleic acid sequence" does not exclude the presence of all other foreign sequences in the virus, for example, foreign promoter sequences, attenuating mutations, mutations or foreign sequences that affect virus tropism, immunogenicity or virus clearance and/or other modifications that are introduced to alter pathogenesis, replication, transcription and/or translation. Further, there may be residual sequences, both native and foreign, (e.g., as a result of the experimental procedures used to produce the construct, for example, restriction sites) in the construct that may be transcribed or even translated (e.g., if operably associated with the alphavirus 26S promoter). Such sequences, however, do not encode a polypeptide of interest or functional untranslated RNA, as those terms are used herein.

In representative embodiments, the viral adjuvant comprises a viral genomic nucleic acid that lacks sequences encoding the viral structural proteins and further in which the viral promoter that is operably associated therewith is inactivated or deleted therefrom. Optionally, the adjuvant virus does not comprise a heterologous nucleic acid sequence (as described above). Thus, according to this embodiment, the viral adjuvant can be a "minimal" replication-competent nucleic acid or viral particle that lacks sequences encoding the structural proteins (i.e., is propagation incompetent) and the genomic promoter associated therewith, but does not comprises a heterologous nucleic acid in the form of a sequence that encodes a polypeptide of interest or functional untranslated RNA or a stuffer RNA. In some embodiments, the "minimal" nucleic acid or virus particle comprises sequences necessary for the nucleic acid or virus particle to self-replicate.

In illustrative embodiments of the invention, the viral adjuvant comprises: (a) a viral coat comprising virus structural proteins; and (b) a modified viral genome that lacks sequences encoding the viral structural proteins required for production of new virus particles; wherein the modified viral genome does not comprise a heterologous nucleic acid sequence that encodes a polypeptide of interest or a functional untranslated RNA. In particular embodiments, the viral adjuvant comprises one, two or more alphavirus structural proteins (e.g., all of the structural proteins in the virion coat are alphavirus structural proteins). In other embodiments, the modified viral genome is a modified alphavirus genome. Optionally, the 26S promoter is inactivated or deleted. Alternatively, the viral adjuvant comprises a nucleic acid (e.g., DNA) that encodes the modified alphavirus genome. In some embodiments, the viral adjuvant is a self-replicating viral adjuvant.

Further, the viral adjuvant can be a VEE viral adjuvant comprising a virion coat comprising one, two or more VEE structural proteins (e.g., all of the structural proteins in the virion coat are VEE structural proteins). In other particular embodiments, the viral adjuvant is a VEE viral adjuvant comprising a modified VEE genome that lacks the sequences encoding the VEE structural proteins required for production of new virus particles. Optionally, the VEE viral adjuvant comprises a modified viral genome that lacks sequences encoding the viral structural proteins. In particular embodiments, the modified viral genome does not comprise a heterologous nucleic acid sequence that encodes a polypeptide of interest or functional untranslated RNA. Alternatively, the VEE viral adjuvant comprises a nucleic acid (e.g., DNA) that encodes the modified VEE genome. In particular embodiments, the VEE 26S promoter is inactivated or deleted from the modified VEE genome. In some embodiments, the VEE viral adjuvant is a self-replicating VEE viral adjuvant.

In other embodiments, the viral adjuvant is a VEE viral adjuvant comprising: VEE structural proteins; and a modified VEE genome that lacks the genes encoding the VEE structural proteins required for production of new virus particles.

A. Alphavirus Adjuvants.

The present invention may be practiced using alphavirus adjuvants, for example, a propagation-incompetent, replicating, alphavirus vector such as an alphavirus replicon vector (as described below), an alphavirus-like particle of assembled structural proteins, or an alphavirus nucleic acid. Alphavirus vectors, including replicon vectors, are described in U.S. Pat. No. 5,505,947 to Johnston et al.; U.S. Pat. No. 5,792,462 to Johnston et al.; U.S. Pat. No. 6,156,558; U.S. Pat. No. 6,521,325; U.S. Pat. No. 6,531,135; U.S. Pat. No. 6,541,010; and Pushko et al. (1997) Virol. 239:389-401; U.S. Pat. No. 5,814,482 to Dubensky et al.; U.S. Pat. No. 5,843,723 to Dubensky et al.; U.S. Pat. No. 5,789,245 to Dubensky et al.; U.S. Pat. No. 5,739,026 to Garoff et al.; the disclosures of which are incorporated herein by reference in their entireties. In embodiments of the invention, the alphavirus vector is a Sindbis (e.g., TR339) or VEE vector, a Sindbis or VEE replicon vector, a Sindbis chimeric vector comprising a Sindbis genomic RNA or Sindbis glycoproteins (i.e., E1 and E2), or a VEE chimeric vector comprising a VEE genomic RNA or VEE glycoproteins.

The alphavirus adjuvants employed in the present invention may be a chimeric alphavirus particle, as that term is understood in the art and defined herein. For example, the alphavirus structural proteins may be from one alphavirus (e.g., VEE or a Sindbis virus such as TR339) and a genomic RNA packaged within the virion may be from another alphavirus. Alternatively, the alphavirus coat can be assembled from structural proteins derived from more than one alphavirus.

i. Double Promoter Vectors.

In embodiments of the invention, the viral adjuvant comprises an alphavirus double promoter vector (e.g., a viral particle or a naked genomic RNA or a nucleic acid encoding the genomic RNA). A double promoter vector is typically a replication and propagation competent virus that retains the sequences encoding the alphavirus structural proteins sufficient to produce an alphavirus particle. Double promoter vectors are described in U.S. Pat. Nos. 5,185,440, 5,505,947 and 5,639,650, the disclosures of which are incorporated in their entireties by reference. Illustrative alphaviruses for constructing the double promoter vectors are Sindbis (e.g., TR339), Girdwood and VEE viruses. In addition, the double promoter vector may contain one or more attenuating mutations. Attenuating mutations are described in more detail hereinbelow.

In representative embodiments, the double promoter vector is constructed so as to contain a second subgenomic promoter (i.e., 26S promoter) inserted 3' to the viral RNA encoding the structural proteins or between nsP4 and the native 26S promoter. The heterologous RNA may be inserted between the second subgenomic promoter, so as to be operatively associated therewith, and the 3' UTR of the virus genome. Heterologous RNA sequences of less than 3 kilobases, more preferably those less than 2 kilobases, and more preferably still those less than 1 kilobase, can be inserted into the double promoter vector. In a preferred embodiment of the invention, the double promoter vector is derived from a Sindbis (e.g., TR339) genomic RNA, and the second subgenomic promoter is a duplicate of the Sindbis (e.g., TR339) subgenomic promoter. In an alternate preferred embodiment, the double promoter vector is derived from a VEE genomic RNA (e.g., having a mutation at nt3 of the genomic RNA), and the second subgenomic promoter is a duplicate of the VEE subgenomic promoter.

ii. Replicon Vectors.

The viral adjuvant can comprise an alphavirus replicon vector (e.g., a viral particle or naked genomic RNA or a nucleic acid encoding a genomic RNA), which are infectious, propagation-defective, replicating virus vectors. Replicon vectors are described in more detail in WO 96/37616 to Johnston et al.; U.S. Pat. No. 5,505,947 to Johnston et al.; U.S. Pat. No. 5,792,462 to Johnston et al.; U.S. Pat. No. 6,156,558; U.S. Pat. No. 6,521,325; U.S. Pat. No. 6,531,135; U.S. Pat. No. 6,541,010; and Pushko et al. (1997) Virol. 239:389-401. Illustrative alphaviruses for constructing the replicon vectors according to the present invention are Sindbis (e.g., TR339), Girdwood, VEE, and chimeras thereof.

In general, in the replicon system, the viral genome contains the viral sequences necessary for viral replication (e.g., the nsp1-4 genes), but is modified so that it is defective for expression of at least one viral structural protein required for production of new viral particles. RNA transcribed from this vector contains sufficient viral sequences (e.g., the viral nonstructural genes) responsible for RNA replication and transcription. Thus, if the transcribed RNA is introduced into susceptible cells, it will be replicated and translated to give the replication proteins. These proteins will transcribe the recombinant genomic RNA, and optionally a transgene (if present). The autonomously replicating RNA (i.e., replicon) can only be packaged into virus particles if the defective or alphavirus structural protein genes that are deleted from or defective in the replicon are provided on one or more helper molecules, which are provided to the helper cell, or by a stably transformed packaging cell.

Preferably, the helper molecules do not contain the viral nonstructural genes for replication, but these functions are provided in trans by the replicon molecule. The transcriptase functions translated from the replicon molecule transcribe the structural protein genes on the helper molecule, resulting in the synthesis of viral structural proteins and packaging of the replicon into virus-like particles. Preferably, the helper molecules do not contain a functional alphavirus packaging signal. As the alphavirus packaging or encapsidation signal is located within the nonstructural genes, the absence of these sequences in the helper molecules precludes their incorporation into virus particles.

Accordingly, the replicon molecule is "propagation defective" or "propagation incompetent," as described hereinabove. Typically, the resulting alphavirus particles are propagation defective inasmuch as the replicon RNA in these particles does not encode all of the alphavirus structural proteins required for encapsidation, at least a portion of at least one of the required structural proteins being deleted therefrom, such that the replicon RNA initiates only an abortive infection; no new viral particles are produced, and there is no spread of the infection to other cells. Alternatively, the replicon RNA may comprise one or more mutations within the structural protein coding sequences or promoter driving expression of the structural protein coding sequences, which interfere(s) with the production of a functional structural protein(s).

Typically, the replicon molecule comprises an alphavirus packaging signal.

The replicon molecule is self-replicating. Accordingly, the replicon molecule comprises sufficient coding sequences for the alphavirus nonstructural polyprotein so as to support self-replication. In embodiments of the invention, the replicon encodes the alphavirus nsP1, nsP2, nsP3 and nsP4 proteins.

The replicon molecules of the invention do not encode one or more of the capsid, E1 or E2 alphavirus structural proteins. By "do(es) not encode" one or more structural proteins, it is intended that the replicon molecule does not encode a functional form of the one or more structural proteins and, thus, a complementing sequence must be provided by a helper or packaging cell to produce new virus particles. In embodiments of the invention, the replicon molecule does not encode any of the alphavirus structural proteins.

The replicon may not encode the structural protein(s) because the coding sequence is partially or entirely deleted from the replicon molecule. Alternatively, the coding sequence is otherwise mutated so that the replicon does not express the functional protein. In embodiments of the invention, the replicon lacks all or substantially all of the coding sequence of the structural protein(s) that is not encoded by the replicon, e.g., so as to minimize recombination events with the helper sequences.

In particular embodiments, the replicon molecule may encode at least one, but not all, of the alphavirus structural proteins. For example, the alphavirus capsid protein may be encoded by the replicon molecule. Alternatively, one or both of the alphavirus glycoproteins may be encoded by the replicon molecule. As a further alternative, the replicon may encode the capsid protein and either the E1 or E2 glycoprotein.

In more preferred embodiments, none of the alphavirus structural proteins are encoded by the replicon molecule. For example, all or substantially all of the sequences encoding the structural proteins (e.g., E1, E2 and capsid) may be deleted from the replicon molecule.

In some aspects of the invention, a composition comprising a population of replicon particles of the invention contains no detectable propagation-competent alphavirus particles. Propagation-competent virus may be detected by any method known in the art, e.g., by neurovirulence following intracerebral injection into suckling mice, or by passage twice on alphavirus-permissive cells (e.g., BHK cells) and evaluation for virus induced cytopathic effects.

Replicon vectors that do not encode the alphavirus capsid protein, may nonetheless comprise a capsid translational enhancer region operably associated with a heterologous sequence, or the sequences encoding the non-structural proteins and/or encoding the alphavirus structural proteins (e.g., E1 and/or E2 glycoproteins) so as to enhance expression thereof. See, e.g., PCT Application No. PCT/US01/27644; U.S. Pat. No. 6,224,879 to Sjoberg et al., Smerdou et al., (1999) *J. Virology* 73:1092; Frolov et al., (1996) *J. Virology* 70:1182; and Heise et al. (2000) *J. Virol.* 74:9294-9299 (the disclosures of which are incorporated herein in their entireties).

In particular embodiments, the replicon vector is an "empty" replicon vector that does not comprise a heterologous nucleic acid sequence (as described herein) or a "minimal" replicon vector in which the 26S subgenomic promoter is deleted or inactivated (also as described herein).

iii. Attenuating Mutations.

The methods of the present invention may also be carried out with alphavirus genomic RNA, structural proteins, and particles including attenuating mutations. The phrases "attenuating mutation" and "attenuating amino acid," as used herein, mean a nucleotide sequence containing a mutation, or an amino acid encoded by a nucleotide sequence containing a mutation, which mutation results in a decreased probability of causing disease in its host (i.e., reduction in virulence), in accordance with standard terminology in the art. See, e.g., B. Davis et al., MICROBIOLOGY 132 (3d ed. 1980). The phrase "attenuating mutation" excludes mutations or combinations of mutations that would be lethal to the virus.

Appropriate attenuating mutations will be dependent upon the alphavirus used, and will be known to those skilled in the art. Exemplary attenuating mutations include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. No. 5,792,462 to Johnston et al., and U.S. Pat. No. 5,639,650 to Johnston et al., the disclosures of which are incorporated herein in their entirety by reference.

When the alphavirus structural proteins are from VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine or histidine as E2 amino acid 209; codons at E1 amino acid 272 which specify an attenuating amino acid, preferably threonine or serine as E1 amino acid 272; codons at E1 amino acid 81 which specify an attenuating amino acid, preferably isoleucine or leucine as E1 amino acid 81; codons at E1 amino acid 253 which specify an attenuating amino acid, preferably serine or threonine as E1 amino acid 253; or the deletion of E3 amino acids 56-59, or a combination of the deletion of E3 amino acids 56-59 together with codons at E1 amino acid 253 which specify an attenuating mutation, as provided above.

Another suitable attenuating mutation is an attenuating mutation at nucleotide 3 of the VEE genomic RNA, i.e., the third nucleotide following the 5' methylated cap (see, e.g., U.S. Pat. No. 5,643,576 describing a G→C mutation at nt 3). The mutation may be a G→A, U or C, but is preferably a G→A mutation.

When the alphavirus structural and/or non-structural proteins are from S.A.AR86, exemplary attenuating mutations in the structural and non-structural proteins include, but are not limited to, codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid position 372 which specify an attenuating amino acid, preferably leucine, at E2 amino acid residue 372; codons at E2 amino acid position 376 which specify an attenuating amino acid, preferably alanine as E2 amino acid 376; in combination, codons at E2 amino acid residues 304, 314, 372 and 376 which specify attenuating amino acids, as described above; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372; in combination, codons at nsP2 amino acid residues 96 and 372 which encode attenuating amino acids at nsP2 amino acid residues 96 and 372, as described above; codons at nsP2 amino acid residue 529 which specify an attenuating amino acid, preferably leucine, at nsP2 amino acid residue 529; codons at nsP2 amino acid residue 571 which specify an attenuating amino acid, preferably asparagine, at nsP2 amino acid residue 571; codons at nsP2 amino acid residue 682 which specify an attenuating amino acid, preferably arginine, at nsP2 amino acid residue 682; codons at nsP2 amino acid residue 804 which specify an attenuating amino acid, preferably arginine, at nsP2 amino acid residue 804; codons at nsp3 amino acid residue 22 which specify an attenuating amino acid, preferably arginine, at nsP3 amino acid residue 22; and in combination, codons at nsP2 amino acid residues 529, 571, 682 and 804 and at nsP3 amino acid residue 22 which specify attenuating amino acids, as described above.

Other illustrative attenuating mutations include those described in PCT Application No. PCT/US01/27644 (the disclosure of which is incorporated herein in its entirety). For example, the attenuating mutation may be an attenuating mutation at amino acid position 537 of the S.A.AR86 nsP3 protein, more preferably a substitution mutation at this position (see, e.g., Table 1 below), still more preferably a nonsense mutation that results in substitution of a termination codon. Translational termination (i.e., stop) codons are known in the art, and include the "opal" (UGA), "amber" (UAG) and "ochre" (UAA) termination codons. In embodiments of the invention, the attenuating mutation results in a Cys→opal substitution at S.A.AR85 nsP3 amino acid position 537.

Further exemplary attenuating mutations include an attenuating insertion mutation following amino acid 385 of the S.A.AR86 nsP3 protein. Preferably, the insertion comprises an insertion of at least 2, 4, 6, 8, 10, 12, 14, 16 or 20 amino acids. In embodiments of the invention, the inserted amino acid sequence is rich in serine and threonine residues (e.g., comprises at least 2, 4, 6, or 8 such sites) that serve as a substrate for phosphorylation by serine/threonine kinases.

In some embodiments, the attenuating mutation comprises an insertion of the amino acid sequence Ile-Thr-Ser-Met-Asp-Ser-Trp-Ser-Ser-Gly-Pro-Ser-Ser-Leu-Glu-Ile-Val-Asp (SEQ ID NO:1) following amino acid 385 of nsP3 (i.e., the first amino acid is designated as amino acid 386 in nsP3). In other embodiments of the invention, the insertion mutation comprises insertion of a fragment of SEQ ID NO:1 that results in an attenuated phenotype. Preferably, the fragment comprises at least 4, 6, 8, 10, 12, 14 or 16 contiguous amino acids from SEQ ID NO:1.

Those skilled in the art will appreciate that other attenuating insertion sequences comprising a fragment of the sequence set forth above, or which incorporate conservative amino acid substitutions into the sequence set forth above, may be routinely identified by those of ordinary skill in the art (as described above). While not wishing to be bound by any theory, it appears that the insertion sequence of SEQ ID NO:1 is highly phosphorylated at serine residues, which confers an attenuated phenotype. Thus, other attenuating insertion sequences which serve as substrates for serine (or threonine) phosphorylation may be identified by conventional techniques known to those skilled in the art.

Alternatively, or additionally, the attenuating mutation comprises a Tyr→Ser substitution at amino acid 385 of the S.A.AR86 nsP3 (i.e., just prior to the insertion sequence above). This sequence is conserved in the non-virulent Sindbis-group viruses, but is deleted from S.A.AR86.

Other attenuating mutations for S.A.AR86 include attenuating mutations at those positions that diverge between S.A.AR86 and non-neurovirulent Sindbis group viruses, including attenuating mutations at nsP2 amino acid position 256 (preferably Arg->Ala), 648 (preferably Ile->Val) or 651 (preferably Lys->Glu), attenuating mutations at nsP3 amino acid position 344 (preferably Gly->Glu), 441 (preferably Asp->Gly) or 445 (preferably Ile->Met), attenuating mutations at E2 amino acid position 243 (preferably Ser->Leu), attenuating mutations at 6K amino acid position 30 (preferably Val->Ile), and attenuating mutations at E1 amino acid positions 112 (preferably Val->Ala) or 169 (preferably Leu->Ser).

As a further option are alphavirus adjuvants comprising an alphavirus capsid protein (or a nucleic acid encoding an alphavirus capsid protein) in which there is an attenuating mutation in the capsid protease that reduces, preferably ablates, the autoprotease activity of the capsid and results, therefore, in non-viable virus. Capsid mutations that reduce or ablate the autoprotease activity of the alphavirus capsid are known in the art, see e.g., WO 96/37616 to Johnston et al., the disclosure of which is incorporated herein in its entirety. In particular embodiments, the alphavirus adjuvant comprises a VEE capsid protein in which the capsid protease is reduced or ablated, e.g., by introducing an amino acid substitution at VEE capsid position 152, 174, or 226. Alternatively, one or more of the homologous positions in other alphaviruses may be altered to reduce capsid protease activity.

If the alphavirus adjuvant comprises a Sindbis-group virus (e.g., Sindbis, TR339, S.A.AR86, Girdwood SA, Ockelbo) capsid protein, the attenuating mutation may be a mutation at capsid amino acid position 215 (e.g., a Ser→Ala) that reduces capsid autoprotease activity (see, Hahn et al., (1990) *J. Virology* 64:3069).

It is not necessary that the attenuating mutations eliminate all pathology or adverse effects associated with administration of the viral adjuvant, as long as there is some improvement or benefit (e.g., increased safety and/or reduced morbidity and/or reduced mortality) as a result of the attenuating mutation.

In particular embodiments, the attenuating mutation is an attenuating mutation in one or more of the cleavage domains between the alphavirus nonstructural (nsp) genes, e.g., the nsP1/nsP2 cleavage region, the nsP2/nsP3 cleavage region, and/or the nsP3/nsP4 cleavage region as described in PCT Application No. PCT/US01/27644 (the disclosure of which is incorporated herein in its entirety). An exemplary attenuating mutation is a mutation at S.A.AR86 nsP1 amino acid 538 (position P3), more preferably a substitution mutation at S.A.AR86 nsP1 amino acid 538, still more preferably a Thr→Ile substitution at S.A.AR86 nsP1 amino acid 538.

In particular preferred embodiments, the attenuating mutation reduces (e.g., by at least 25%, 40%, 50%, 60%, 70%, 80%, 90%, 95% or more) the neurovirulence of the alphavirus adjuvant (e.g., as determined by intracerebral injection in weanling or adult mice).

Those skilled in the art may identify attenuating mutations other than those specifically disclosed herein using other methods known in the art, e.g., looking at neurovirulence in weanling or adult mice following intracerebral injection. Methods of identifying attenuating mutations in alphaviruses are described by Olmsted et al., (1984) *Science* 225:424 and Johnston and Smith, (1988) *Virology* 162:437; the disclosures of which are incorporated herein in their entireties.

To identify other attenuating mutations other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the genomic RNA sequence (or a DNA sequence), according to the following codon table:

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC ACU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In identifying other attenuating mutations, the hydropathic index of amino acids may be considered. The importance of the hydropathic amino acid index in conferring interactive biologic function on a protein is generally understood in the art (see, Kyte and Doolittle, (1982) *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, Id.), these are:
isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when identifying additional attenuating mutations according to the present invention.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); threonine (+0.3); asparagine (+0.2); glutamine (+0.2); glycine (0); threonine (−0.4); proline (−0.5±I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional attenuating mutations according to the present invention.

Mutations may be introduced into the alphavirus genome by any method known in the art. For example, mutations may be introduced into the alphavirus RNA by performing site-directed mutagenesis on the cDNA which encodes the RNA, in accordance with known procedures (see, Kunkel, *Proc. Natl. Acad. Sci. USA* 82, 488 (1985), the disclosure of which is incorporated herein by reference in its entirety). Alternatively, mutations may be introduced into the RNA by replacement of homologous restriction fragments in the cDNA which encodes for the RNA in accordance with known procedures.

iv Helper Cells, Helper Constructs and Methods of Producing Viral Particles.

Further aspects of the present invention are methods and helper cells for producing the alphavirus adjuvants. Methods and helper cells for producing alphavirus particles, including double-promoter alphaviruses and alphavirus replicon particles are known in the art. See, e.g., U.S. Pat. No. 5,185,440 to Davis et al., U.S. Pat. No. 5,505,947 to Johnston et al.; U.S. Pat. No. 5,792,462 to Johnston et al.; U.S. Pat. No. 6,156,558; U.S. Pat. No. 6,521,325; U.S. Pat. No. 6,531,135; U.S. Pat. No. 6,541,010; and Pushko et al. (1997) *Virol.* 239:389-401; the disclosures of which are incorporated herein by reference in their entireties.

In representative embodiments, the methods and helper cells are used to produce propagation-incompetent alphavirus particles, more preferably, propagation-incompetent alphavirus replicon particles. According to this embodiment, the helper cells contain one or more helper nucleic acid sequences (e.g., as DNA and/or RNA molecules) encoding the alphavirus structural proteins (e.g., VEE structural proteins). The combined expression of the replicon molecule and the one or more helper molecules in the helper cell results in the production of an assembled alphavirus particle comprising a replicon RNA packaged within a virion comprising alphavirus structural proteins, which is able to infect a cell, but is unable to produce a productive infection (i.e., produce new virus particles).

Preferably, the population of alphavirus particles contains no detectable propagation-competent alphavirus particles. Propagation-competent virus may be detected by any method known in the art, e.g., by neurovirulence following intracerebral injection into suckling mice, or by passage twice on alphavirus-permissive cells (e.g., BHK cells) and evaluation for virus induced cytopathic effects.

Thus, according to one embodiment of the invention, the present invention provides a method of producing a recombinant alphavirus particle in vitro, comprising: providing to a cell in culture: (a) a modified alphavirus genomic RNA, comprising (i) sequences encoding the alphavirus nonstructural proteins, and (ii) a competent alphavirus packaging sequence, and further (iii) wherein the genomic RNA is defective for the expression of at least one viral structural protein required for production of new virus particles; (b) sequences encoding the alphavirus structural proteins sufficient for producing an alphavirus particle; wherein the combined expression of the alphavirus replicon RNA and the sequences encoding the alphavirus structural proteins produces an assembled alphavirus particle comprising the modified alphavirus genomic RNA; and producing an alphavirus particle in the cell.

As described more generally above, the replicon RNA can comprise a heterologous RNA that encodes a polypeptide of interest or functional untranslated RNA. Alternatively, the replicon does not comprise a heterologous RNA that encodes a polypeptide of interest or functional untranslated RNA. The replicon can optionally be an "empty" replicon that does not comprise a heterologous nucleic acid (e.g., in place of the deleted structural protein genes) or, further, a "minimal" replicon in which the 26S promoter is deleted or inactivated.

Where the invention is carried out to make a stock of alphavirus replicon particles, the helper cell comprises helper sequences which may be provided as an RNA or DNA molecule(s), or may be stably expressed by the cell by integration into the cellular DNA or from an episome. In other embodiments of the invention, the helper cell further comprises one or more replicon molecules, as described herein.

Typically, the helper sequences will not include an alphavirus packaging sequence, whereas the replicon will contain an alphavirus packaging sequence (e.g., a VEE packaging sequence).

The helper cells are typically alphavirus-permissive cells. Alphavirus-permissive cells employed in the methods of the present invention are cells that, upon transfection with an alphavirus genomic RNA (or a nucleic acid encoding the same), are capable of producing viral particles. Preferred alphavirus-permissive cells are Sindbis permissive cells (e.g., TR339-permissive cells), VEE permissive cells, S.A.AR86-permissive cells, Girdwood-permissive cells, and Semliki Forest virus-permissive cells. Alphaviruses have a broad host range. Examples of suitable host cells include, but are not limited to fibroblasts, Vero cells, baby hamster kidney (BHK) cells, 293 cells, 293T cells, and chicken embryo fibroblast cells (e.g., DF-1 cells).

In particular embodiments, the helper cells of the invention may further comprise sequences encoding the alphavirus structural proteins sufficient to produce an alphavirus particle, as described herein. Alternatively, or additionally, the helper cell may comprise a replicon RNA, also as described herein.

As described hereinabove, in the production of a replicon particle, sequences encoding the alphavirus structural proteins are distributed among one or more helper molecules (optionally, two or three helper RNAs). In addition, one or more structural proteins may be encoded by the replicon RNA, provided that the replicon RNA does not encode at least one structural protein such that the resulting alphavirus particle is propagation-incompetent in the absence of the helper sequence(s).

At least one of the alphavirus structural and/or non-structural proteins encoded by the replicon and helper molecules can contain one or more attenuating mutations, as described herein.

The helper sequences and/or replicon may further comprise an alphavirus capsid enhancer sequence (e.g., a S.A.AR86 capsid enhancer sequence), as described above. See, e.g., PCT Application No. PCT/US01/27644; U.S. Pat. No. 6,224,879 to Sjoberg et al., Smerdou et al., (1999) *J. Virology* 73:1092; Frolov et al., (1996) *J. Virology* 70:1182; and Heise et al. (2000) *J. Virol.* 74:9294-9299 (the disclosures of which are incorporated herein in their entireties).

In one particular embodiment, the replicon molecule encodes at least one, but not all, of the alphavirus structural proteins (e.g., the E1 and/or E2 glycoproteins and/or the capsid protein). According to this embodiment, the replicon can encode the capsid protein, and the E1 and E2 glycoproteins are encoded by one or more separate helper molecules. Optionally, the glycoproteins are encoded by two separate helper molecules, so as to minimize the possibility of recombination to produce replication-competent virus.

In another embodiment, the replicon does not encode any of the E1 glycoprotein, the E2 glycoprotein, or the capsid protein. According to this embodiment, the capsid protein and alphavirus glycoproteins are encoded by one or more helper molecules, optionally two or more helper molecules. By distributing the coding sequences for the structural proteins among two, three or even more helper molecules, the likelihood that recombination will result in replication-competent virus is reduced.

In a further embodiment, the replicon does not encode any of the alphavirus structural proteins, and may lack the sequences encoding the alphavirus structural proteins.

As described above, the replicon may not encode the structural protein(s) because of a partial or complete deletion of the coding sequence(s) or otherwise contains a mutation that prevents the expression of a functional protein(s). In embodiments of the invention, all or substantially all of the coding sequences for the structural protein(s) that is not encoded by the replicon are deleted from the replicon molecule.

In one illustrative embodiment, the E1 and E2 glycoproteins are encoded by one helper molecule, and the capsid protein is encoded by another helper molecule. In another particular embodiment, the E1 glycoprotein, E2 glycoprotein, and capsid protein are each encoded by separate helper molecules. In other embodiments, the capsid protein and one of the glycoproteins are encoded by one helper molecule, and the other glycoprotein is encoded by a second helper molecule.

In some embodiments, duplicate copies of the structural proteins are not present among the replicon and helper molecules. If duplicate copies of the structural proteins are present, generally other approaches are used to avoid recombination events and/or generation of replication-competent virus.

The helper and replicon sequences can be RNA molecules that are introduced into the cell, e.g., by lipofection or electroporation. Uptake of helper RNA and replicon RNA molecules into packaging cells in vitro can be carried out according to any suitable means known to those skilled in the art. Uptake of RNA into the cells can be achieved, for example, by treating the cells with DEAE-dextran, treating the RNA with LIPOFECTIN™ before addition to the cells, or by electroporation, with electroporation being the currently preferred means. These techniques are well known in the art. See e.g., U.S. Pat. No. 5,185,440 to Davis et al., and PCT Publication No. WO 92/10578 to Bioption AB, the disclosures of which are incorporated herein by reference in their entirety.

Alternatively, one or all of the helper and/or replicon molecules are DNA molecules, which are optionally stably integrated into the genome of the helper cell or expressed from an episome (e.g., an EBV derived episome). The DNA molecule may be any vector known in the art, including but not limited to a non-integrating DNA vector, such as a plasmid, or a viral vector.

B. DNA Sequences, Vectors and Transformed Cells.

As a further aspect, the invention provides nucleic acids encoding the viral adjuvants of the invention. For example, the present invention provides DNA sequences (e.g., cDNA sequences) and vectors encoding infectious modified alphavirus genomic RNA transcripts (e.g., VEE genomic transcripts) as described herein. Also provided are alphavirus particles containing the genomic RNA transcribed from the DNA molecules.

The present invention further provides vectors and constructs comprising a DNA sequence encoding the alphavirus genomic RNA transcript described above operably associated with a promoter that drives transcription of the DNA sequence. Examples of promoters which are suitable for use with the DNA sequences of the present invention include, but are not limited to T3 promoters, T7 promoters, cytomegalovirus (CMV) promoters, and SP6 promoters.

The DNA sequence may be embedded within any suitable vector known in the art, including but not limited to, plasmids, naked DNA vectors, yeast artificial chromosomes (yacs), bacterial artificial chromosomes (bacs), phage, viral vectors, and the like. Preferably, the vector is a plasmid.

Genomic RNA transcripts may be synthesized from the DNA template by any method known in the art. Preferably, the RNA is synthesized from the DNA sequence in vitro using purified RNA polymerase in the presence of ribonucleotide triphosphates and cap analogs in accordance with conventional techniques. Alternatively, the RNA may be synthesized intracellularly after introduction of the DNA.

Further provided are cells containing the DNA sequences, genomic RNA transcripts, and alphavirus vectors of the invention. Exemplary cells include, but are not limited to, fibroblast cells, Vero cells, Baby Hamster Kidney (BHK) cells, Chinese Hamster Ovary (CHO) cells, macrophages, dendritic cells, and the like.

C. Compositions Comprising the Viral Adjuvant and an Immunogen.

The invention further encompasses compositions, including pharmaceutical compositions, comprising the viral adjuvant and an immunogen.

The immunogen can be any immunogen known in the art and can be administered in any suitable form. For example, the immunogen can be in the form of a live, attenuated live, or killed (i.e., inactivated) organism (e.g., a bacterium or protozoan) or virus, or an extract or toxoid thereof. In other embodiments, the immunogen can be provided as an isolated component (e.g., a polypeptide or a peptide [e.g., from about 6 to 20 or 8 to 12 amino acids in length]). Further, the immunogen can be administered per se or can be expressed from a nucleic acid that is administered to the host and the immunogen expressed therefrom. To illustrate, according to this embodiment, a delivery vector, such as a recombinant viral vector or a plasmid that expresses the immunogen, is administered to the host with the viral adjuvant and the immunogen produced in the host. The immunogen can comprise B cell and/or T cell epitopes as are known in the art. The immunogen can further be soluble or particulate (e.g., microspheres).

The immunogen can be present in the organism. For example, in the case of a chronic or latent infection in the subject, the subject fails to mount a sufficient immune response against the antigen. The viral adjuvants of the invention can be administered to the subject to induce an immune response against the antigen already present in the subject as a result of the infection.

The immunogen can be an immunogen from an infectious agent, a cancer immunogen, an allergic reaction immunogen (i.e., an allergen), a transplantation immunogen, an autoantigen, and the like as are known in the art.

To illustrate, a cancer immunogen (i.e., an immunogen associated with cancer cells, optionally specifically associated with cancer cells) can include, without limitation, HER2/neu and BRCA1 antigens for breast cancer, MART-1/MelanA, gp100, tyrosinase, TRP-1, TRP-2, NY-ESO-1, CDK-4, β-catenin, MUM-1, Caspase-8, KIAA0205, HPVE7, SART-1, PRAME, and p15 antigens, members of the MAGE family, the BAGE family (such as BAGE-1), the DAGE/PRAME family (such as DAGE-1), the GAGE family, the RAGE family (such as RAGE-1), the SMAGE family, NAG, TAG-72, CA125, mutated proto-oncogenes such as p21 ras, mutated tumor suppressor genes such as p53, tumor associated viral antigens (e.g., HPV16 E7), the SSX family, HOM-MEL-55, NY-COL-2, HOM-HD-397, HOM-RCC-1.14, HOM-HD-21, HOM-NSCLC-11, HOM-MEL-2.4, HOM-TES-11, RCC-3.1.3, NY-ESO-1, and the SCP family. Members of the MAGE family include, but are not limited to, MAGE-1, MAGE-2, MAGE-3, MAGE-4 and MAGE-11. Members of the GAGE family include, but are not limited to, GAGE-1, GAGE-6. See, e.g., review by Van den Eynde and van der Bruggen (1997) in Curr. Opin. Immunol. 9: 684-693, Sahin et al. (1997) in Curr. Opin. Immunol. 9: 709-716, and Shawler et al. (1997), the entire contents of which are incorporated by reference herein for their teachings of cancer antigens.

The cancer immunogen can also be, but is not limited to, human epithelial cell mucin (Muc-1; a 20 amino acid core repeat for Muc-1 glycoprotein, present on breast cancer cells and pancreatic cancer cells), MUC-2, MUC-3, MUC-18, the Ha-ras oncogene product, carcino-embryonic antigen (CEA), the raf oncogene product, CA-125, GD2, GD3, GM2, TF, sTn, gp75, EBV-LMP 1 & 2, HPV-F4, 6, 7, prostatic serum antigen (PSA), prostate-specific membrane antigen (PSMA), alpha-fetoprotein (AFP), 0017-1A, GA733, gp72, p53, the ras oncogene product, β-HCG, gp43, HSP-70, p17 mel, HSP-70, gp43, HMW, HOJ-1, melanoma gangliosides, TAG-72, mutated proto-oncogenes such as p21 ras, mutated tumor suppressor genes such as p53, estrogen receptor, milk fat globulin, telomerases, nuclear matrix proteins, prostatic acid phosphatase, protein MZ2-E, polymorphic epithelial mucin (PEM), folate-binding-protein LK26, truncated epidermal growth factor receptor (EGFR), Thomsen-Friedenreich (T) antigen, GM-2 and GD-2 gangliosides, polymorphic epithelial mucin, folate-binding protein LK26, human chorionic gonadotropin (HCG), pancreatic oncofetal antigen, cancer antigens 15-3, 19-9, 549, 195, squamous cell carcinoma antigen (SCCA), ovarian cancer antigen (OCA), pancreas cancer associated antigen (PaA), mutant K-ras proteins, mutant p53, and chimeric protein $p210_{BCR-ABL}$ and tumor associated viral antigens (e.g., HPV16 E7).

The cancer immunogen can also be an antibody produced by a B cell tumor (e.g., B cell lymphoma; B cell leukemia; myeloma; hairy cell leukemia), a fragment of such an antibody, which contains an epitope of the idiotype of the antibody, a malignant B cell antigen receptor, a malignant B cell immunoglobulin idiotype, a variable region of an immunoglobulin, a hypervariable region or complementarity determining region (CDR) of a variable region of an immunoglobulin, a malignant T cell receptor (TCR), a variable region of a TCR and/or a hypervariable region of a TCR. In one embodiment, the cancer antigen of this invention can be a single chain antibody (scFv), comprising linked $V_H$ and $V_L$ domains, which retains the conformation and specific binding activity of the native idiotype of the antibody.

The immunogens that can be used in accordance with the present invention are in no way limited to the cancer immunogens listed herein. Other cancer immunogens can be identified, isolated and cloned by methods known in the art such as those disclosed in U.S. Pat. No. 4,514,506, the entire contents of which are incorporated by reference herein.

The cancer to be treated or immunized against (i.e., prophylactic treatment) by administration to a subject of a viral adjuvant of this invention can be, but is not limited to, B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, uterine cancer, adenocarcinoma, breast cancer, pancreatic cancer, colon cancer, lung cancer, renal cancer, bladder cancer, liver cancer, prostate cancer, ovarian cancer, primary or metastatic melanoma, squamous cell carcinoma, basal cell carcimona, brain cancer, angiosarcoma, hemangiosarcoma, head and neck carcinoma, thyroid carcinoma, soft tissue sarcoma, bone sarcoma, testicular cancer, uterine cancer, cervical cancer, gastrointestinal cancer, and any other cancer now known or later identified (see, e.g., Rosenberg (1996) *Ann. Rev. Med.* 47:481-491, the entire contents of which are incorporated by reference herein).

Infectious agent immunogens can include any immunogen suitable for protecting a subject against an infectious disease, including but not limited to microbial, bacterial, protozoal, parasitic and viral diseases. Such infectious agent immunogens can include, but are not limited to, immunogens from Hepadnaviridae including hepatitis A, B, C, D, E, F, G, etc.; Flaviviridae including human hepatitis C virus (HCV), yellow fever virus and dengue viruses; Retroviridae including human immunodeficiency viruses (HIV), simian immunodeficiency virus (SIV), and human T lymphotrophic viruses (HTLV1 and HTLV2); Herpesviridae including herpes simplex viruses (HSV-1 and HSV-2), Epstein Barr virus (EBV), cytomegalovirus, varicella-zoster virus (VZV), human herpes virus 6 (HHV-6) human herpes virus 8 (HHV-8), and herpes B virus; Papovaviridae including human papilloma viruses; Rhabdoviridae including rabies virus; Paramyxoviridae including respiratory syncytial virus; Reoviridae including rotaviruses; Bunyaviridae including hantaviruses; Filoviridae including Ebola virus; Adenoviridae; Parvoviridae including parvovirus B19; Arenaviridae including Lassa virus; Orthomyxoviridae including influenza viruses; Poxviridae including Orf virus, molluscum contageosum virus, smallpox virus and Monkey pox virus; Togaviridae including Venezuelan equine encephalitis virus; Coronaviridae including corona viruses such as the severe acute respiratory syndrome (SARS) virus; and Picornaviridae including polioviruses; rhinoviruses; orbiviruses; picodnaviruses; encephalomyocarditis virus (EMV); Parainfluenza viruses, adenoviruses, Coxsackieviruses, Echoviruses, Rubeola virus, Rubella virus, human papillomaviruses, Canine distemper virus, Canine contagious hepatitis virus, Feline calicivirus, Feline rhinotracheitis virus, TGE virus (swine), Foot and mouth disease virus, simian virus 5, human parainfluenza virus type 2, human metapneuomovirus, enteroviruses, and any other pathogenic virus now known or later identified (see, e.g., *Fundamental Virology*, Fields et al., Eds., 3$^{rd}$ ed., Lippincott-Raven, New York, 1996, the entire contents of which are incorporated by reference herein for the teachings of pathogenic viruses).

As further examples, the immunogen may be an orthomyxovirus immunogen (e.g., an influenza virus immunogen, such as the influenza virus hemagglutinin (HA) surface protein, influenza neuraminidase protein, the influenza virus nucleoprotein (NP) antigen or inactivated influenza virions, or an equine influenza virus immunogen), or a lentivirus immunogen (e.g., an equine infectious anemia virus immunogen, a SIV immunogen, or a HIV immunogen, such as, e.g., HIV or SIV gp120, gp160, gp41, or matrix/capsid protein, or the gag, pol or env gene products). The immunogen may also be an arenavirus immunogen (e.g., Lassa fever virus immunogen, such as the Lassa fever virus nucleocapsid protein gene and the Lassa fever envelope glycoprotein gene), a Picornavirus immunogen (e.g., a Foot and Mouth Disease virus immunogen), a poxvirus immunogen (e.g., a vaccinia immunogen, such as the vaccinia L1 or L8 genes), an Orbivirus immunogen (e.g., an African horse sickness virus immunogen), a flavivirus immunogen (e.g., a yellow fever virus immunogen, a West Nile virus immunogen, or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS immunogens), a norovirus immunogen (e.g., a Norwalk virus immunogen), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio antigen, herpes antigen (e.g., CMV, EBV, HSV antigens) mumps antigen, measles antigen, rubella antigen, diptheria toxin or other diptheria antigen, pertussis antigen, hepatitis (e.g., hepatitis A or hepatitis B) antigen (e.g., HBsAg, HBcAg, HBeAg), or any other vaccine immunogen known in the art.

The immunogen can be an immunogen from a pathogenic microorganism, which can include but is not limited to, *Rickettsia, Chlamydia, Mycobacteria, Clostridia, Corynebacteria, Mycoplasma, Ureaplasma, Legionella, Shigella, Salmonella*, pathogenic *Escherichia coli* species, *Bordatella, Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., 4$^{th}$ ed., Lippincott, New York, 1990, the entire contents of which are incorporated herein by reference for the teachings of pathogenic microorganisms).

Specific examples of microorganisms from which the immunogen of this invention can be obtained include, but are not limited to, *Helicobacter pylori, Chlamydia pneumoniae, Chlamydia trachomatis, Ureaplasma urealyticum, Mycoplasma pneumoniae, Staphylococcus aureus, Streptococcus pyogenes, Streptococcus pneumoniae, Streptococcus viridans, Enterococcus faecalis, Neisseria meningitidis, Neisseria gonorrhoeae, Treponema pallidum, Bacillus anthracis, Salmonella typhi, Vibrio cholera, Pasteurella pestis, Pseudomonas aeruginosa, Campylobacter jejuni, Clostridium difficile, Clostridium botulinum, Mycobacterium tuberculosis, Borrelia burgdorferi, Haemophilus ducreyi, Corynebacterium diphtheria, Bordetella pertussis, Bordetella parapertussis, Bordetella bronchiseptica, Haemophilus influenza*, and enterotoxic *Escherichia coli*.

The immunogen can further be an immunogen from a pathogenic protozoa, including, but not limited to, *Plasmodium* species (e.g., malaria antigens), *Babeosis* species, *Schistosoma* species, *Trypanosoma* species, *Pneumocystis carnii, Toxoplasma* species, *Leishmania* species, and any other protozoan pathogen now known or later identified.

The immunogen can also be an immunogen from pathogenic yeast and fungi, including, but not limited to, *Aspergillus* species, *Candida* species, *Cryptococcus* species, *Histoplasma* species, *Coccidioides* species, and any other pathogenic fungus now known or later identified.

Other specific examples of various immunogens include, but are not limited to, the influenza virus nucleoprotein (residues 218-226; Fu et al. (1997) *J. Virol.* 71: 2715-2721), antigens from Sendai virus and lymphocytic choriomeningitis virus (An et al. (1997) *J. Virol.* 71: 2292-2302), the B1 protein of hepatitis C virus (Bruna-Romero et al. (1997) *Hepatology* 25: 470-477), gp 160 of HIV (Achour et al. (1996) *J. Virol.* 70: 6741-6750), amino acids 252-260 of the circumsporozoite protein of *Plasmodium berghei* (Allsopp et al. (1996) *Eur. J. Immunol.* 26: 1951-1958), the influenza A virus nucleoprotein (residues 366-374; Nomura et al. (1996) *J. Immunol. Methods* 193: 4149), the listeriolysin O protein of *Listeria monocytogenes* (residues 91-99; An et al. (1996) *Infect. Immun.* 64: 1685-1693), the E6 protein (residues 131-140; Gao et al. (1995) *J. Immunol.* 155: 5519-5526) and E7 protein (residues 21-28 and 48-55; Bauer et al. (1995) *Scand. J. Immunol.* 42: 317-323) of human papillomavirus type 16, the M2 protein of respiratory syncytial virus (residues 82-90 and 81-95; Hsu et al. (1995) *Immunology* 85: 347-350), the herpes simplex virus type 1 ribonucleotide reductase (Salvucci et al. (1995) *J. Gen. Virol.* 69: 1122-1131), the rotavirus VP7 protein (Franco et al. (1993) *J. Gen. Virol.* 74: 2579-2586), *P. falciparum* antigens (causing malaria) and hepatitis B surface antigen (Gilbert et al. (1997) *Nature Biotech.* 15: 1280-1283).

The immunogen can also be an immunogen from chronic or latent infective agents, which typically persist because they fail to elicit a strong immune response in the subject. Illustrative latent or chronic infective agents include, but are not limited to, hepatitis B, hepatitis C, Epstein-Barr Virus, herpes viruses, human immunodeficiency virus, and human papilloma viruses. The adjuvant is beneficial because (1) it may induce proinflammatory cytokines and interferon, and/or (2) it acts as an adjuvant to enhance the immune response against the antigen that is already present from the infection.

The viral adjuvants of the invention can be used to produce an immune response to, and optionally to treat or to prevent infection (i.e., prophylactic treatment) from any infectious agent, including but not limited to those identified above.

Suitable transplantation immunogens include, but are not limited to, different antigenic specificities of HLA-A, B and C Class I proteins. Different antigenic specificities of HLA-DR, HLA-DQ, HLA-DP and HLA-DW Class II proteins can also be used (WHO Nomenclature Committee, *Immunogenetics* 16:135 (1992); Hensen et al., in *Fundamental Immunology*, Paul, Ed., pp. 577-628, Raven Press, New York, 1993; NIH Genbank and EMBL data bases).

Immunogens that are allergens are also contemplated by the present invention, which can include but are not limited to, environmental allergens such as dust mite allergens; plant allergens such as pollen, including ragweed pollen; insect allergens such as bee and ant venom; and animal allergens such as cat dander, dog dander and animal saliva allergens.

In particular embodiments of the invention, the immunogen is a ragweed allergen or a grass allergen.

Ragweed, and in particular Short Ragweed (*Ambrosia artemisiifolia*), is clinically the most important source of seasonal aeroallergens, as it is responsible for both the majority of cases and the most severe cases of allergic rhinitis (Pollart, et al. (1989) *J. Allergy Clin. Immunol.* 83(5):875-82; Rosenberg, et al. (1983) *J. Allergy Clin. Immunol.* 71(3):302-10; Bruce, et al. (1977) *J. Allergy Clin. Immunol.* 59(6): 449-59). Ragweed pollen also contributes significantly to exacerbation of asthma and allergic conjunctivitis.

Grass pollen is the most frequent cause of hay fever. Although more than 1,000 species of grass grow in North America, only a few produce highly allergenic pollen. These include Timothy grass, Kentucky bluegrass, Johnson grass, Bermuda grass, redtop grass, orchard grass, velvet grass, rye grass and sweet vernal grass.

Accordingly, in particular embodiments, the immunogen is an allergen from ragweed or a grass species including, but not limited to, those listed Table II.

TABLE II

| Protein | Accession No. | Source | Reference |
|---|---|---|---|
| Amb a 1 | P27759 | Common ragweed (*A. artemisiifolia*) | Rafnar, et al. (1991) J. Biol. Chem. 266: 1229-1236 |
| Amb a 2 | P27762 | Common ragweed (*A. artemisiifolia*) | Rogers, et al. (1991) J. Immunol. 147: 2547-2552 |
| Amb a 3 | P00304 | Common ragweed (*A. artemisiifolia*) | Klapper, et al. (1980) Biochemistry 19: 5729-5734 |
| Amb a 5 | P02878 | Common ragweed (*A. artemisiifolia*) | Mole, et al. (1975) Biochemistry 14: 1216-1220 |
| Amb a 6 | O04004 | Common ragweed (*A. artemisiifolia*) | Hiller, et al. (1980) Scand. J. Immunol. 48: 26-36 |
| Amb t 5 | P10414 | Giant ragweed (*A. trifida*) | Goodfriend, et al. (1985) Mol. Immunol. 22: 899-906 |
| Art v 1 | AAO24900 | Mugwort (*A. vulgaris*) | Himly, et al. (2003) FASEB J. 17 (1): 106-108 |
| Art v 2 | A38624 | Mugwort (*A. vulgaris*) | Nilson, et al. (1991) J. Biol. Chem. 266 (4): 2660-2668 |
| Hel a 2 | O81982 | Sunflower (*Helianthus annuus*) | Asturias, et al. (1998) Mol. Immunol. 35 (8): 469-478 |
| Mer a 1 | O49894 | *Mercurialis annua* | Vallverdu, et al. (1998) J. Allergy Clin. Immunol. 101: 363-370 |
| Che a 1 | AAL07319 | lamb's-quarters, pigweed ((*Chenopodium album*) | N/A |
| Che a 2 | AAL92870 | white goosefoot (*C. album*) | N/A |
| Che a 3 | AAL92871 | white goosefoot (*C. album*) | N/A |
| Sal k 1 | P83181 | Russian-thistle (*Salsola kali*) | N/A |
| Par j 1 | P43217 | *Parietaria judaica* | Costa, et al. (1994) FEBS Lett. 341: 182-186 |
| Par j 2 | P55958 | *P. judaica* | Duro, et al. (1996) FEBS Lett. 399: 295-298 |
| Par j 3 | Q9XG85 | *P. judaica* | N/A |
| Par o 1 | A53252 | *P. officinalis* | Oreste, et al. (1991) Int. Arch. Allergy Appl. Immunol. 96 (1): 19-27 |
| Cyn d 1 | O04701 | Bermuda grass (*Cynodon dactylon*) | Smith, et al. (1996) J. Allergy Clin. Immunol. 98: 331-343 |
| Cyn d 7 | P94092 | Bermuda grass (*C. dactylon*) | Suphioglu, et al. (1997) FEBS Lett. 402: 167-172 |
| Cyn d 12 | O04725 | Bermuda grass (*C. dactylon*) | Asturias, et al. (1997) Clin. Exp. Allergy 27: 1307-1313 |
| Cyn d 15 | AAP80171 | Bermuda grass (*C. dactylon*) | N/A |
| Cyn d 23 | AAP80170 | Bermuda grass (*C. dactylon*) | N/A |
| Dac g 1 | AAP96759 | Orchard grass (*Dactylis glomerata*) | N/A |
| Dac g 2 | Q41183 | Orchard grass (*D. glomerata*) | Roberts, et al. (1992) Immunology 76: 389-396 |
| Dac g 3 | P93124 | Orchard grass (*D. glomerata*) | Guerin-Marchand, et al. (1996) Mol. Immunol. 33: 797-806 |

TABLE II-continued

| Protein | Accession No. | Source | Reference |
|---|---|---|---|
| Dac g 4 | P82946 | Orchard grass (*D. glomerata*) | Leduc-Brodard, et al. (1996) J. Allergy Clin. Immunol. 98: 1065-1072 |
| Hol l 1 | P43216 | Velvet grass (*Holcus lanatus*) | Schramm, et al. (1997) J. Allergy Clin. Immunol. 99: 781-787 |
| Lol p 1 | P14946 | Rye grass (*Lolium perenne*) | Griffith, et al. (1991) FEBS Lett. 279: 210-215 |
| Lol p 2 | P14947 | Rye grass (*L. perenne*) | Ansari, et al. (1989) J. Biol. Chem. 264: 11181-11185 |
| Lol p 3 | P14948 | Rye grass (*L. perenne*) | Ansari, et al. (1989) Biochemistry 28: 8665-8670 |
| Lol p 5 | Q40240 | Rye grass (*L. perenne*) | Singh, et al. (1991) Proc. Natl. Acad. Sci. USA 88: 1384-1388 |
| Pha a 1 | Q41260 | Canary grass (*Phalaris aquatica*) | Suphioglu, et al. (1995) Clin. Exp. Allergy 25: 853-865 |
| Phl p 1 | P43213 | Timothy grass (*Phleum pratense*) | Laffer, et al. (1994) J. Allergy Clin. Immunol. 94: 689-698 |
| Phl p 2 | P43214 | Timothy grass (*P. pratense*) | Dolecek, et al. (1993) FEBS Lett. 335: 299-304 |
| Phl p 5a | Q40962 | Timothy grass (*P. pratense*) | Bufe, et al. (1994) J. Allergy Clin. Immunol. 94: 173-181 |
| Phl p 5b | Q40963 | Timothy grass (*P. pratense*) | Bufe, et al. (1995) FEBS Lett. 363: 6-12 |
| Phl p 6 | P43215 | Timothy grass (*P. pratense*) | Petersen, et al. (1995) Int. Arch. Allergy Immunol. 108: 55-59 |
| Phl p 11 | P35079 | Timothy grass (*P. pratense*) | Valenta, et al. (1994) Biochem. Biophys. Res. Commun. 199: 106-118 |

N/A, not available

In general, the weed and grass allergens provided in Table II are members of the polysaccharide lyase family 1 of proteins (e.g., Amb a 1 and Amb a 2); lipid transfer proteins (e.g., Par j 1, Par j 2, Par o 1); profilins (e.g., Hel a 2, Mer a 1, Che a 2, Par j 3, Cyn d 12); polcalcins (e.g., Che a 3), or proteins with homology to trypsin inhibitors (e.g., Phl p 11).

In other embodiments, the immunogen is an allergen isolated from trees such as oak (e.g., Que a 1), mountain cedar (e.g, Jun a 1-Jun a 3), birch (e.g., Bet v 1-Bet v 7), ash (e.g, Fra e 1), alder (e.g., Aln g 1), hazel (e.g., Cor a 1, Cor a 2, or Cor a 8-Cor a 11), juniper (e.g., Jun o 4), and cypress (e.g., Cup a 1); molds such as *Alternaria alternata* (e.g., Alt a 1-Alt a 4, Alt a 6, Alt a 7, or Alt a 10-Alt a 12), *Cladosporium herbarum* (e.g., Cla h 1-Cla h 6, or Cla h 12), *Aspergillus flavus* (e.g., Asp fl 13), *A. fumigatus* (e.g., Asp f 1-Asp f 13, Asp f 15-Asp f 18, Asp f 22w or Asp f 23), *A. niger* (e.g., Asp n 14 or Asp n 18), *A. oryzae* (e.g., Asp o 13 or Asp o 21), *Penicillium brevicompactum* (e.g., Pen ch 13, Pen ch 18, or Pen ch 20), *P. citrinum* (e.g., Pen c 3, Pen c 13, Pen c 19, Pen c 22w, or Pen c 24), *P. oxalicum* (e.g., Pen o 18), *Epicoccum purpurascens* (e.g., Epi p 1), or *Fusarium culmorum* (e.g., Fus c 1 or Fus c 2); egg whites (e.g., Gal d 1-Gal d 5); milk (e.g., Bos d 4-Bos d 8); wheat (e.g., Tri a 18 and Tri a 19); cat (Fel d 1-Fel d 7w); dust mites (e.g., Aca s 13, Blo t 1, Blo t 3-Blo t 6, Blo t 10-Blo t 13, Blo t 19, Der f 1-Der f 3, Der f 7, Der f 10, Der f 11, Der f 14-Der f 18w, Der m 1, Der p 1-Der p 10, Der p 14, Eur m 2, Eur m 14, Gly d 2, Lep d 2, Lep d 5, Lep d 7, Lep d 10, Lep d 13, or Tyr p 2); or bees (e.g., Api m 1, Api m 2, Api m 4, Api m 6, Api m 7, Born p 1, or Bom p 4).

Other exemplary food, animal, tree, insect and mold allergens are found at http://www.allergen.org/List.htm Marsh and Freidhoff. 1992. ALBE, an allergen database. IUIS, Baltimore, Md., Edition 1.0).

The immunogen can further be an autoantigen (for example, to enhance self-tolerance to an autoantigen in a subject, e.g., a subject in whom self-tolerance is impaired). Exemplary autoantigens include, but are not limited to, myelin basic protein, islet cell antigens, insulin, collagen and human collagen glycoprotein 39, muscle acetylcholine receptor and its separate polypeptide chains and peptide epitopes, glutamic acid decarboxylase and muscle-specific receptor tyrosine kinase.

II. Methods of Administering the Viral Adjuvants of the Invention.

The viral adjuvants of the invention can be used for a variety of purposes. For example, the present invention finds use in methods of producing antibodies in vivo for passive immunization techniques. According to this embodiment a viral adjuvant and immunogen of interest are administered to a subject, either by direct administration or ex vivo cell manipulation techniques as known in the art. The antibody can then be collected from the subject using routine methods known in the art. The invention further finds use in methods of producing antibodies against an immunogen for any other purpose, e.g., for diagnostics or for use in histological techniques.

The viral adjuvants can further be used in therapeutic and/or prophylactic methods, for veterinary and/or medical purposes. Viral adjuvants for use in the methods of the invention are as described above. Additionally, the adjuvant virus of the invention can be administered to the subject as a general immune enhancer to increase both innate and adaptive immune function in the subject, for example, immunocompromised subjects such as subjects undergoing chemotherapy, radiation therapy, subjects with chronic infections (e.g., HCV and HBV) and/or subjects with HIV/AIDs. The invention can further be practiced to enhance the immune response to an attenuated live virus, a killed vaccine, or a DNA vaccine, all of which can have the disadvantage of reduced immunogenicity. In particular embodiments, the adjuvant virus of the invention can be administered to treat a chronic or latent infection to induce or enhance the immune response against the antigen(s) produced by the infection.

Suitable subjects according to the present invention can be any animal subject (e.g., avians and mammalian subjects). Mammalian subjects include but are not limited to humans, non-human primates, dogs, cats, pigs, goats, sheep, cattle, horses, mice, rats and rabbits. Avian subjects include but are not limited to chickens, turkeys, ducks, geese, quail, and birds kept as pets (e.g., parakeets, parrots, macaws, cockatoos, and the like).

In an exemplary embodiment, the invention provides a method of producing an immune response against an immunogen in a subject, the method comprising: (a) administering the immunogen to the subject in an immunogenically effective amount; and (b) administering the viral adjuvant to the subject in an adjuvant effective amount, wherein the viral adjuvant does not express the immunogen. In other words, according to the invention, the viral adjuvant is administered as an adjuvant to enhance the immune response to the immunogen, not as a vaccine vector to deliver the immunogen to the subject. Viral adjuvants are as described hereinabove.

The invention also provides a method of producing an immune response against an immunogen in a subject, the method comprising: (a) administering the immunogen to the subject in an immunogenically effective amount; and (b)

administering an alphavirus (e.g., a propagation-defective alphavirus) adjuvant to the subject in an adjuvant effective amount, wherein the alphavirus adjuvant does not express the immunogen.

In another exemplary embodiment, the invention provides a method of producing an immune response against an immunogen in a subject, the method comprising: (a) administering the immunogen to the subject in an immunogenically effective amount; and (b) administering a VEE viral adjuvant (e.g., a propagation-defective VEE viral adjuvant) to the subject in an adjuvant effective amount, wherein the VEE viral adjuvant does not express the immunogen.

As another aspect, the invention provides for the use of a viral adjuvant for increasing the immune response against an immunogen. Also encompassed by the invention is the use of a virus for the preparation of an adjuvant formulation. Further provided is the use of a viral adjuvant for the preparation of a medicament.

Further provided by the invention is a method of administering an immunogen to a subject, the improvement comprising administering an adjuvant virus of the invention to the subject in an immunogenically effective amount.

An "immunogenically effective amount" is an amount of the immunogen that is sufficient to evoke an active immune response (cellular and/or humoral) in a subject that is co-administered the adjuvant. Optionally, an immunogenically effective amount is sufficient to produce a protective immune response. The degree of protection conferred need not be complete or permanent.

An "adjuvant effective amount" is an amount of the adjuvant virus that is sufficient to enhance or stimulate the active immune response (cellular and/or humoral) mounted by the host against the immunogen, optionally an active mucosal immune response. In particular embodiments, the active immune response (e.g., a mucosal immune response) by the host is enhanced by at least about 2, 3, 4, 5, 10, 15, 20, 30, 40, 50, 60, 75, 100, 150, 500, 1000-fold or more. In other embodiments, an "adjuvant effective amount" is an amount of viral adjuvant that reduces the amount of immunogen required to achieve a specified level of immunity (cellular and/or humoral), optionally mucosal immunity, for example, a reduction of at least about 15%, 25%, 35%, 50%, 65%, 75%, 80%, 85%, 90%, 95%, 98% or more in the amount of immunogen. As a further option, an "adjuvant effective amount" can refer to an amount of the viral adjuvant that accelerates the induction of the immune response in the host and/or reduces the need for booster immunizations to achieve protection. As yet another alternative, an "adjuvant effective amount" can be an amount that prolongs the time period over which an immune response, optionally protective immune response, is sustained (e.g., by at least about a 2-fold, 3-fold, 5-fold, 10-fold, 20-fold longer time period or more).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence and/or severity of disease. Alternatively, a protective immune response or protective immunity may be useful in the therapeutic treatment of disease.

Suitable dosages of the immunogen and viral adjuvant will vary depending upon the condition, age and species of the subject, the nature of the immunogen, the nature of the viral adjuvant, the level of immunogenicity and enhancement desired, and like factors, and can be readily determined by those skilled in the art.

In particular embodiments, the dosage of the viral adjuvant is greater than about $10^{-2}$, $10^{-1}$, 10, $10^2$, $10^3$, $10^4$, $10^5$ or $10^6$ virus particles, virus-like particles, or infectious units and/or less than about $10^2$, $10^3$, $10^4$, $10^5$, $10^6$, $10^7$, $10^8$, $10^9$, $10^{10}$, $10^{11}$, $10^{12}$, $10^{13}$, or even $10^{14}$ or more virus particles, virus-like particles, or infectious units. Those skilled in the art will appreciate that some methods of titering viruses have relatively low sensitivity giving rise to apparent titers of less than one virus particle. Viral titers can be assessed by any method known in the art, including cytotoxicity in cultured cells (e.g., alphavirus titers can be assessed by cytotoxicity in BHK cells). In other representative embodiments, a dosage of about $10^{-1}$ to $10^7$, 10 to $10^6$ or about $10^2$ to $10^4$ virus particles, virus-like particles, or infectious units are administered.

In representative embodiments, the optimal dosage of the viral adjuvant is less than the optimal dosage that would be administered to achieve an immune response against the immunogen if presented by or expressed by the virus or virus component in the viral adjuvant (i.e., if the virus or virus component were being used as a vaccine vector rather than as an adjuvant). In particular embodiments, the optimal vaccine vector dosage is about 5-fold, 10-fold, 100-fold, 1000-fold, 5,000-fold, 10,000-fold, 50,000-fold, 100,000-fold or more greater than the optimal adjuvant dosage.

Further, in particular embodiments, the viral adjuvants of the invention produce an enhanced cellular immune response against an independent immunogen as compared with an immunogen presented by (e.g., on the virion surface) or expressed from the viral genomic nucleic acid that is acting as a vaccine vector. The cellular response can be enhanced by 1.5-fold, 2-fold, 3-fold, 4-fold, 5-fold, 10-fold, 20-fold or more.

The dosage of immunogen can vary greatly depending on the nature and form (e.g., isolated antigen versus whole organism) of the immunogen. In particular embodiments, the dosage of immunogen is from about 1 ng to 500 µg, from about 0.1 µg to 100 µg, or from about 1 µg to about 50 µg. In other representative embodiments, the dosage of immunogen is from about 0.1 ng, 1 ng, 2 ng, 5 ng, 10 ng, 25 ng, 50 ng, 100 ng, 500 ng, 1 µg, 5 µg, 10 µg, 50 µg or 100 µg and up to about 10 ng, 25 ng, 50 ng, 100 ng, 500 ng, 1 µg, 5 µg, 10 µg, 50 µg or 100 µg or more.

In particular embodiments, the amount of immunogen administered to achieve a specified level of immune response (humoral and/or cellular and/or mucosal) in the presence (i.e., co-administration) of the viral adjuvant is reduced as compared with the amount of immunogen in the absence of the viral adjuvant, e.g., a reduction of at least about 15%, 25%, 35%, 50%, 65%, 75%, 80%, 85%, 90%, 95%, 98% or more.

Single or multiple (i.e., booster) dosages of viral adjuvant and/or immunogen can be administered.

The immunogen and viral adjuvant can be co-administered concurrently (e.g., within hours of each other) in the same or different composition and, in the latter case, by the same or different route. Alternatively, the viral adjuvant can be administered prior to or after administration of the immunogen (e.g., about 6, 12, 24, 36, 48, 72, 96 or 120 hours or more before or after administration of the immunogen). According to one embodiment, the viral adjuvant is administered before the immunogen, such that the viral adjuvant virus is present in the draining lymph node when the immunogen is subsequently administered to the subject. In other embodiments, the immunogen is administered before the viral adjuvant, such that the immunogen is still present in the subject (e.g., in the draining lymph node or in the systemic circulation) when the viral adjuvant is subsequently administered to the subject.

The viral adjuvant and immunogen can each independently be administered by any route known in the art, including administration by non-mucosal routes and mucosal routes (each as described herein).

Further, the immunogen and viral adjuvant can be administered to induce a mucosal immune response and/or a systemic immune response. In particular embodiments, the viral adjuvant (and optionally, the immunogen) is administered non-mucosally and a mucosal immune response is induced.

Methods of non-mucosal administration are known in the art and encompass methods of delivery other than to a mucosal surface. Exemplary methods of non-mucosal administration include but are not limited to intraperitoneal, intravenous, intraarterial, intramuscular, intraventricular, intrathecal, transdermal, intradermal, subcutaneous, topical administration, and foot pad administration.

Methods of mucosal administration include any method known in the art for delivering compounds to a mucosal surface such as the respiratory tract, the gastrointestinal tract, the urinary tract, the reproductive tract.

Methods of administration to the respiratory tract include but are not limited to transmucosal, intranasal, inhalation or intratracheal administration or administration to the lungs. The adjuvant virus can be administered to the lungs of a subject by any suitable means, for example, administering an aerosol suspension of respirable particles, which the subject inhales. The respirable particles may be liquid or solid. Aerosols of liquid particles may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the adjuvant virus can likewise be produced with any solid particulate medicament aerosol generator, by techniques known in the pharmaceutical art.

Other methods of mucosal administration include oral, buccal (e.g., sub-lingual), intra-tracheal, rectal, vaginal and intra-ocular administration.

III. Pharmaceutical Formulations.

The invention further provides the viral adjuvant of the invention, compositions comprising a viral adjuvant and an immunogen (or a nucleic acid encoding an immunogen, for example, a delivery vector or a liposomal formulation), and pharmaceutical compositions comprising a viral adjuvant or a pharmaceutical composition comprising a viral adjuvant and an immunogen in a pharmaceutically acceptable excipient. Formulation of pharmaceutical compositions is well known in the pharmaceutical arts (see, e.g., Remington's Pharmaceutical Sciences, (15th Edition, Mack Publishing Company, Easton, Pa. (1975)).

By "pharmaceutically acceptable" it is meant a material that is not biologically or otherwise undesirable, i.e., the material can be administered to a subject without causing any undesirable biological effects such as toxicity.

The formulations of the invention can optionally comprise additional medicinal agents, pharmaceutical agents, carriers, buffers, adjuvants, dispersing agents, diluents, and the like.

The viral adjuvants, and optionally an immunogen, of the invention can be formulated for administration in a pharmaceutical carrier in accordance with known techniques. See, e.g., Remington, The Science And Practice of Pharmacy ($9^{th}$ Ed. 1995). In the manufacture of a pharmaceutical formulation according to the invention, the viral adjuvant is typically admixed with, inter alia, an acceptable carrier. The carrier can be a solid or a liquid, or both, and is preferably formulated as a unit-dose formulation. One or more viral adjuvants (and, optionally, immunogens) can be incorporated in the formulations of the invention, which can be prepared by any of the well-known techniques of pharmacy.

The formulations of the invention include those suitable for oral, rectal, topical, buccal (e.g., sub-lingual), vaginal, intraocular, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transmucosal, intratracheal, transdermal, intraventricular, intraarticular, intrathecal and inhalation administration, administration to the liver by intraportal delivery, as well as direct organ injection (e.g., into the liver, into the brain for delivery to the central nervous system, into the pancreas). The most suitable route in any given case will depend on the nature and severity of the condition being treated and on the nature of the particular viral adjuvant which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the viral adjuvant can be administered in solid dosage forms, such as capsules, tablets, and powders, or in liquid dosage forms, such as elixirs, syrups, and suspensions. The viral adjuvant can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the viral adjuvant in a flavored base, usually sucrose and acacia or tragacanth; and pastilles comprising the viral adjuvant in an inert base such as gelatin and glycerin or sucrose and acacia.

Formulations of the present invention suitable for parenteral administration can comprise sterile aqueous and non-aqueous injection solutions of the viral adjuvant, which preparations are generally isotonic with the blood of the intended recipient. These preparations can contain anti-oxidants, buffers, bacteriostats and solutes, which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets. For example, in one aspect of the present invention, there is provided an injectable, stable, sterile composition comprising a viral adjuvant of the invention, in a unit dosage form in a sealed container. The viral adjuvant is provided in the form of a lyophilizate which is capable of being reconstituted with a suitable pharmaceutically acceptable carrier to form a liquid composition suitable for injection thereof into a subject.

Formulations suitable for rectal or vaginal administration can be presented as suppositories. These can be prepared by admixing the viral adjuvant with one or more conventional excipients or carriers, for example, cocoa butter, polyethylene glycol or a suppository wax, which are solid at room temperature, but liquid at body temperature and therefore melt in the rectum or vaginal cavity and release the viral adjuvant.

Formulations suitable for topical application to the skin can take the form of an ointment, cream, lotion, paste, gel, spray, aerosol, or oil. Carriers that can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3 (6):318 (1986)) and typically take the form of an optionally buffered aqueous solution of the viral adjuvant. Suitable formulations comprise citrate or bis\tris buffer (pH 6) or ethanol/water.

The viral adjuvant can be formulated for nasal administration or otherwise administered to the lungs of a subject by any suitable means, for example, by an aerosol suspension of respirable particles comprising the viral adjuvant, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, Drug Delivery to the Respiratory Tract, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159. Aerosols of liquid particles comprising the viral adjuvant can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the viral adjuvant can likewise be produced with any solid particulate medicament aerosol generator, by techniques known in the pharmaceutical art.

Alternatively, one can administer the viral adjuvant in a local rather than systemic manner, for example, in a depot or sustained-release formulation.

Further, the present invention provides liposomal formulations of the viral adjuvants disclosed herein. The technology for forming liposomal suspensions is well known in the art. When the viral adjuvant is an aqueous-soluble salt, using conventional liposome technology, the same can be incorporated into lipid vesicles. The lipid layer employed can be of any conventional composition and can either contain cholesterol or can be cholesterol-free. The liposomes can be reduced in size, as through the use of standard sonication and homogenization techniques.

Liposomal formulations containing the viral adjuvant can be lyophilized, alone or with immunogen, to produce a lyophilizate which can be reconstituted with a pharmaceutically acceptable carrier, such as water, to regenerate a liposomal suspension.

Particular embodiments of the present invention are described in greater detail in the following non-limiting examples.

Example 1

VEE Adjuvant Particles

In experiments in which formalin-inactivated Influenza virus was utilized as antigen, the adjuvant particles were Venezuelan Equine Encephalitis (VEE) replicon particles driving the expression of green fluorescent protein behind the 26S promoter (VRP-GFP). However, in all subsequent experiments the replicon particles used as adjuvants were "empty" VRP. The empty replicon particles contained an RNA genome which codes for all four of the viral non-structural proteins and a 26S promoter with no transgene cloned downstream in place of the structural protein genes which have been deleted from the RNA genome (see, e.g., Pushko et al. (1997) *Virol.* 239:389-401 for a description of alphavirus replicons in which the structural protein genes have been deleted. Note that Pushko replaced the deleted structural protein genes with a transgene that is operably linked to the 26S promoter). Therefore, these particles do not express any coding sequence downstream of the viral subgenomic promoter. However, an approximately 174 nucleotide RNA (which comprises part of the 5' leader sequence of the subgenomic transcript, a multiple cloning site, and the viral 3' UTR; this sequence has two putative open reading frames that may produce peptides of 3 and 5 amino acids in length, but not a "polypeptide of interest" as defined herein) is expressed behind the 26S promoter, which is upstream of the authentic viral 3' end (including the VEE poly A tail). These empty VRP were used as adjuvants in all of the experiments in which the utilized antigen was ovalbumin (OVA), Norwalk virus VLPs, or SIV gp120. These observations suggest that both particles which express a transgene and particles which do not express a transgene behind the 26S promoter are fully capable of serving as adjuvants. In other experiments, the viral specific sequences which code for the 26S promoter are deleted from the viral adjuvant, but the authentic viral 3' end is retained, and tested for adjuvant activity.

Example 2

Inoculation Methodology

To determine whether mucosal immunity induction following peripheral VRP-HA inoculation was a function of VRP (virus replicon particles) or HA (hemagglutinin), systemic and mucosal immune responses were assessed following inoculation of GFP-expressing VRP (VRP-GFP), formalin-inactivated influenza virus (i.e., dead flu, dflu), or a co-inoculation thereof. Accordingly, groups of three Balb/c animals were either mock-vaccinated and boosted in the right rear footpad or vaccinated and boosted with $10^5$ infectious units (IU) of VRP expressing the hemagglutinin gene from influenza virus VRP-HA, 10 micrograms of dflu, or co-inoculated with $10^5$ IU of VRP-GFP and 10 micrograms of dflu. Mucosal and systemic immune responses were assessed as disclosed in Examples 3-5.

Example 3

Immune Responses Following Peripheral VRP-HA Inoculation

Systemic Immune Responses.

Figure 2:
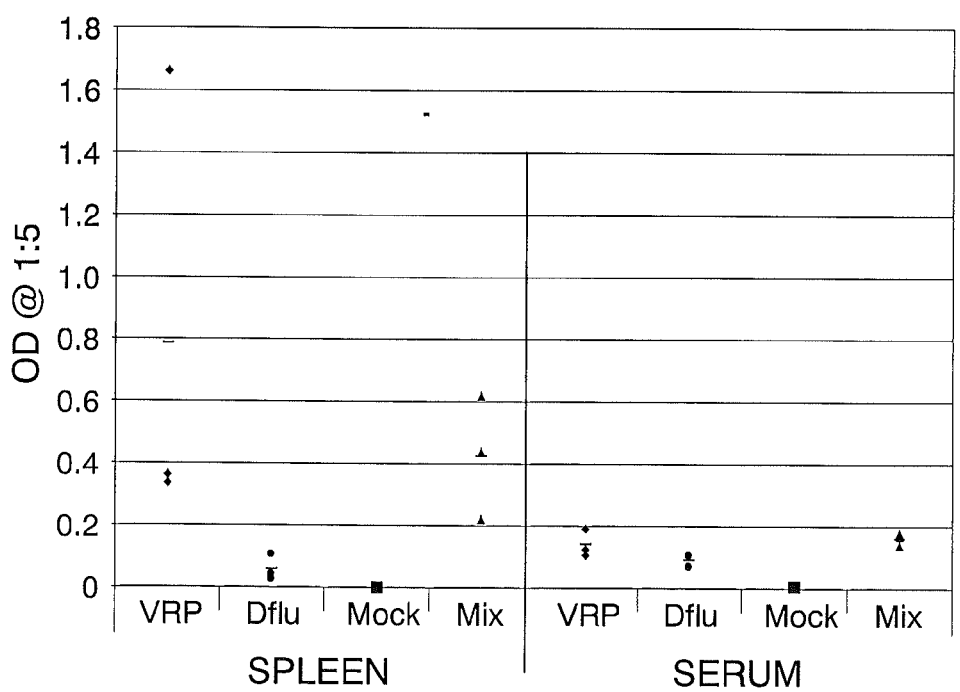
FIG. 2 shows optical density (OD) measurements of an ELISA (1:40 dilution) for IgG production by lymphoid cultures of non-mucosal tissue (spleen and serum) from mice mock-inoculated or inoculated with virus replicon particles expressing hemagglutinin (VRP), formalin-inactivated influenza virus (dflu), or a co-inoculation thereof (mix).

Induction of systemic HA-specific IgG antibody responses in the serum and spleen of Balb/c mice was assessed following co-inoculation of VRP-GFP and dflu. Two weeks post-boost, animals were sacrificed and the spleen and serum were harvested and allowed to incubate at 37° C. for 7 days in tissue culture media. The media was subsequently analyzed for HA-specific IgG antibodies via ELISA. ELISAs were diluted 1:400 and optical density (OD) was measured (FIG. 1). The experiment was repeated and OD measurements were taken for a 1:40 dilution of the ELISA (FIG. 2).

Mucosal Effector Tissue Immune Responses.

Figure 3:
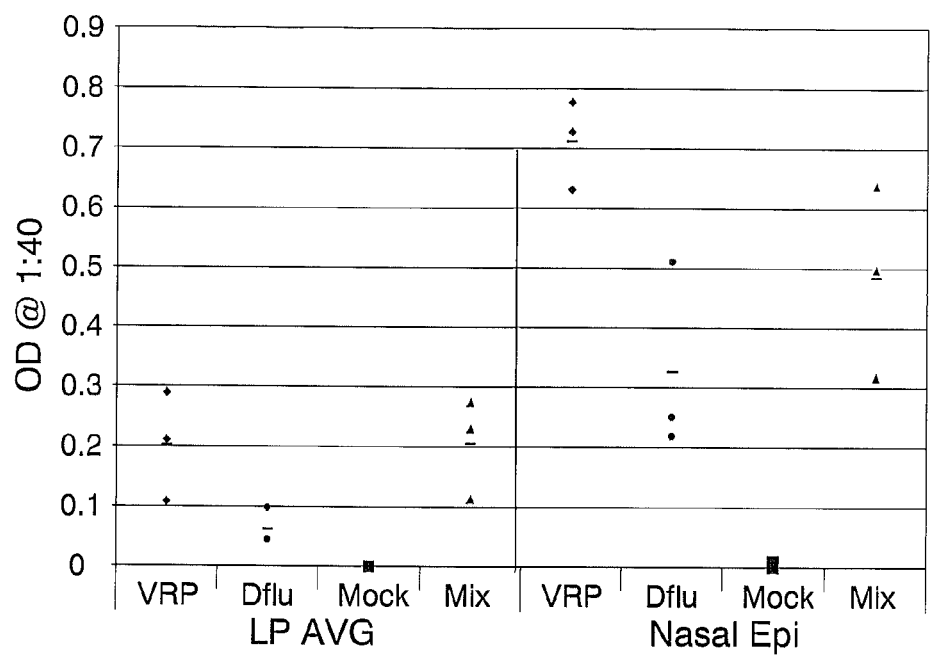
FIG. 3 shows optical density (OD) measurements of an ELISA (1:40 dilution) for IgG production by lymphoid cultures of gut lamina propria (LP AVG) and nasal epithelium (Nasal Epi), representative of mucosal effector tissue, from mice-mock inoculated or inoculated with virus replicon particles expressing hemagglutinin (VRP), formalin-inactivated influenza virus (dflu), or a co-inoculation thereof (mix).
Figure 4:
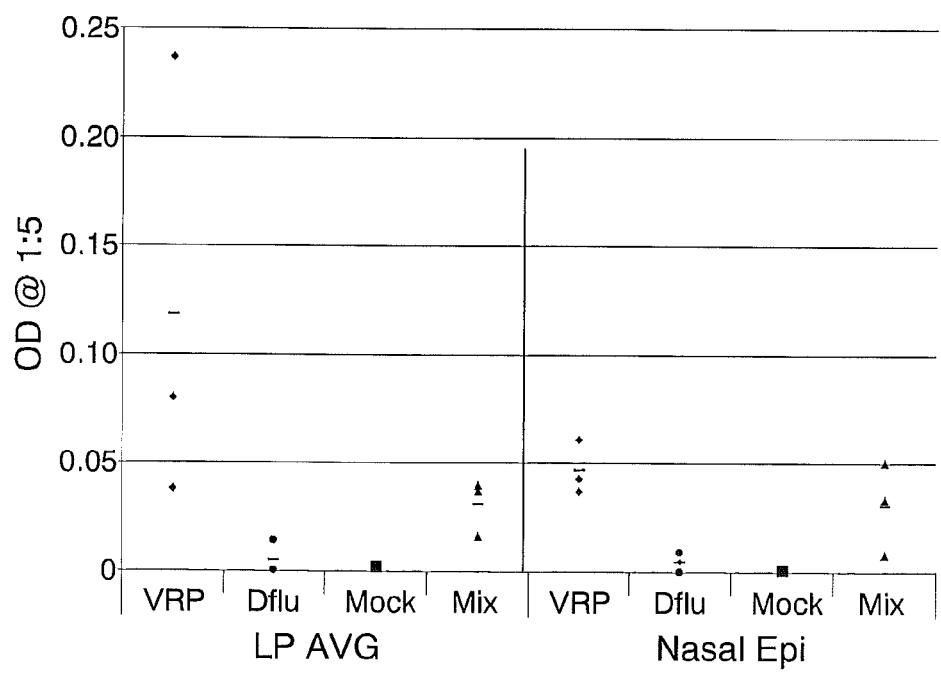
FIG. 4 shows optical density (OD) measurements of an ELISA (1:40 dilution) for IgG production by lymphoid cultures of gut lamina propria (LP AVG) and nasal epithelium (Nasal Epi), representative of mucosal effector tissue, from mice mock-inoculated or inoculated with virus replicon particles expressing hemagglutinin (VRP), formalin-inactivated influenza virus (dflu), or a co-inoculation thereof (mix).

Induction of HA-specific IgG antibody responses in mucosal effector tissues was assessed following co-inoculation of VRP-GFP and dflu. Two weeks post-boost, animals were sacrificed and the gut lamina propria and nasal epithelium were harvested and allowed to incubate at 37° C. for 7 days in tissue culture media. The media was subsequently analyzed for HA-specific IgG antibodies via ELISA. ELISAs were diluted 1:40 and OD was measured (FIG. 3). Experiments were repeated with similar results (FIG. 4).

Mucosal IgA Production.

Figure 5:
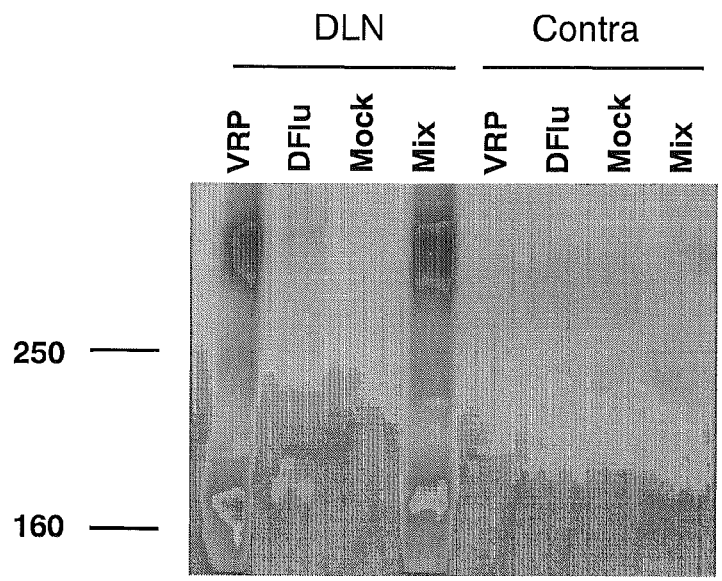
FIG. 5 shows dimeric IgA production in the draining lymph node (DLN) and contralateral lymph node (Contra) from mice mock-inoculated or inoculated with virus replicon particles expressing hemagglutinin (VRP), formalin-inactivated influenza virus (dflu), or a co-inoculation thereof (mix).

Dimeric IgA production was assessed in supernatants from the draining lymph node (DLN) following co-inoculation of VRP-GFP and dflu. Three days post-boost, animals were sacrificed and the DLN, contralateral lymph node, and mesenteric lymph node were harvested and allowed to incubate at 37° C. for 7 days in tissue culture media. Proteins in tissue culture supernatants were separated by SDS polyacrylamide gel electrophoresis (SDS-PAGE) under non-reducing conditions and probed with an anti-IgA antibody. Dimeric IgA, also referred to as mucosal IgA, was visible as a >300 kDa band in mice inoculated with VRP-HA or co-inoculated with VRP-GFP and dflu (FIG. 5). No bands were visible in the dflu or mock-inoculated mice or the control blot.

Example 4

HA-Specific Immune Responses Following Peripheral VRP-HA Inoculation

Systemic HA-Specific IgG Antibody.

Figure 6:
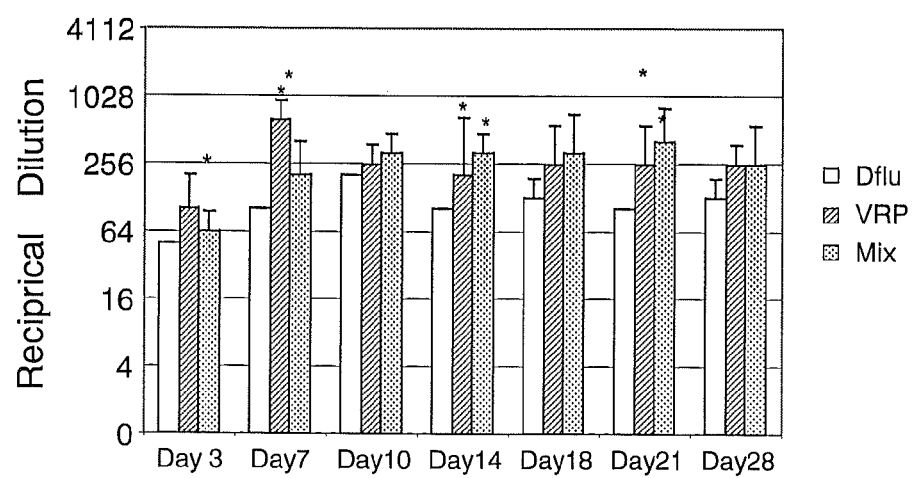
FIG. 6 shows systemic HA-specific IgG antibody production in the spleen mice following inoculation with virus replicon particles expressing hemagglutinin (VRP), formalin-inactivated influenza virus (dflu), or a co-inoculation thereof (mix). Reciprocal dilution at which the OD is >0.2 is shown.

Induction of systemic HA-specific IgG antibody responses in the spleen of mice was assessed following co-inoculation of VRP-GFP and dflu. At various time points post-boost (days 3, 7, 10, 14, 18, 21, and 28), animals were sacrificed and the spleen was harvested and allowed to incubate at 37° C. for 7 days in tissue culture media. The media was subsequently analyzed for HA-specific IgG antibodies via ELISA. FIG. 6 shows the reciprocal dilution at which the OD is >0.2.

Systemic HA-Specific IgA Antibody.

Figure 7:
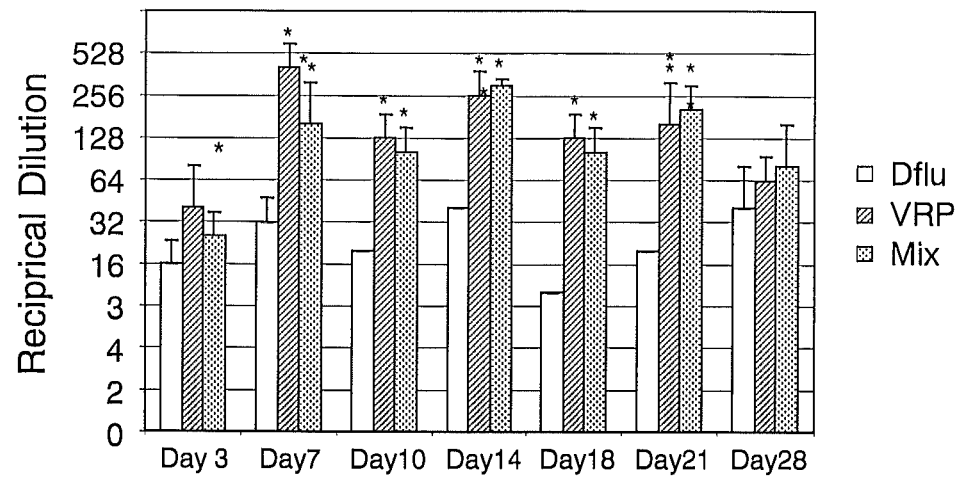
FIG. 7 shows systemic HA-specific IgA antibody production in the spleen of mice following inoculation with virus replicon particles expressing hemagglutinin (VRP), formalin-inactivated influenza virus (dflu), or a co-inoculation thereof (mix). Reciprocal dilution at which the OD is > two standard deviations over mock is shown.

Induction of systemic HA-specific IgA antibody responses in the spleen of mice was assessed following co-inoculation of VRP-GFP and dflu. At various time points post-boost (days 3, 7, 10, 14, 18, 21, and 28), animals were sacrificed and the spleen was harvested and allowed to incubate at 37° C. for 7 days in tissue culture media. The media was subsequently analyzed for HA-specific IgA antibodies via ELISA. FIG. 7 shows the reciprocal dilution at which the OD is > two standard deviations over mock.

Mucosal HA-Specific IgG Antibody.

Figure 8:
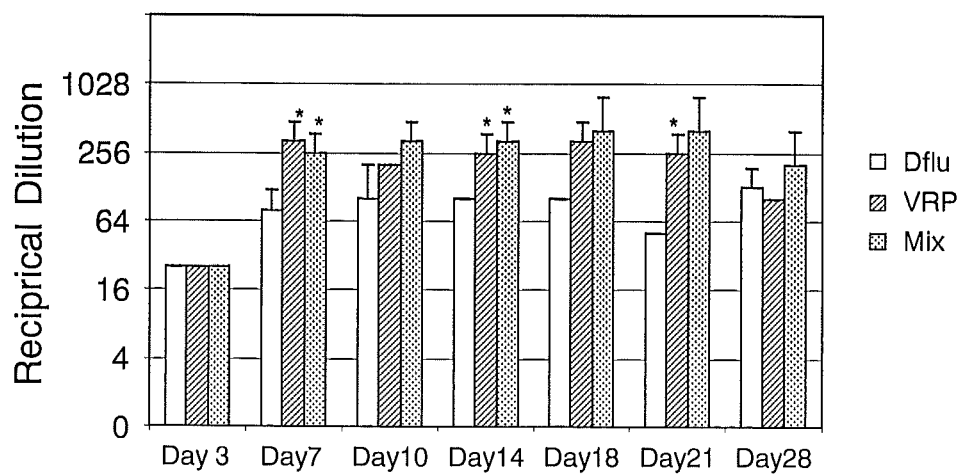
FIG. 8 shows mucosal HA-specific IgG antibody production in nasal epithelium of mice following inoculation with virus replicon particles expressing hemagglutinin (VRP), formalin-inactivated influenza virus (dflu), or a co-inoculation thereof (mix). Reciprocal dilution at which the OD is >0.2 is shown.

Induction of mucosal HA-specific IgG antibody responses in the nasal epithelium of mice was assessed following co-inoculation of VRP-GFP and dflu. At various time points post-boost (days 3, 7, 10, 14, 18, 21, and 28), animals were sacrificed and the nasal epithelium was harvested and allowed to incubate at 37° C. for 7 days in tissue culture media. The media was subsequently analyzed for HA-specific IgG antibodies via ELISA. FIG. 8 shows the reciprocal dilution at which the OD is >0.2.

Mucosal HA-Specific IgA Antibody.

Figure 9:
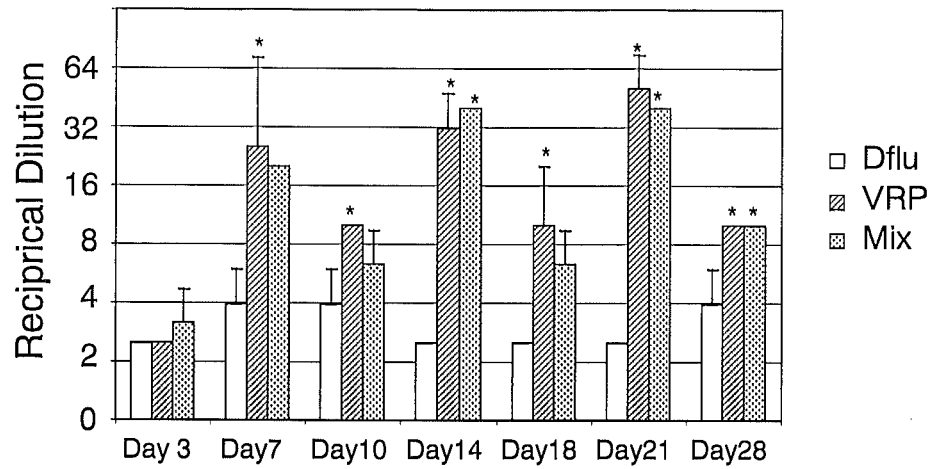
FIG. 9 shows mucosal HA-specific IgA antibody production in nasal epithelium of mice following inoculation with virus replicon particles expressing hemagglutinin (VRP), formalin-inactivated influenza virus (dflu), or a co-inoculation thereof (mix). Reciprocal dilution at which the OD is > two standard deviations over mock is shown.

Induction of mucosal HA-specific IgA antibody responses in the nasal epithelium of mice was assessed following co-inoculation of VRP-GFP and dflu. At various time points post-boost (days 3, 7, 10, 14, 18, 21, and 28), animals were sacrificed and the nasal epithelium was harvested and allowed to incubate at 37° C. for 7 days in tissue culture media. The media was subsequently analyzed for HA-specific IgA antibodies via ELISA. FIG. 9 shows the reciprocal dilution at which the OD is > two standard deviations over mock.

HA-Specific IgG Antibody Production in DLN.

Figure 10:
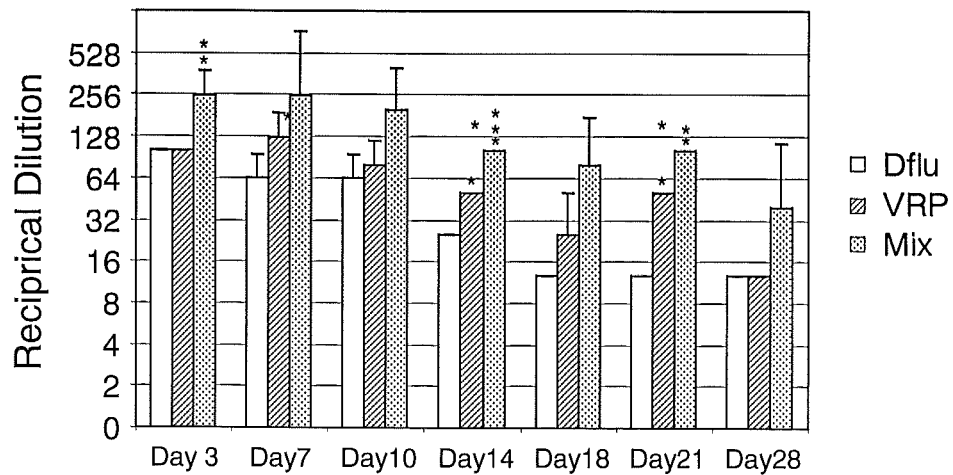
FIG. 10 shows HA-specific IgG antibody production in DLN of mice following inoculation with virus replicon particles expressing hemagglutinin (VRP), formalin-inactivated influenza virus (dflu), or a co-inoculation thereof (mix). Reciprocal dilution at which the OD is >0.2 is shown.

Induction of HA-specific IgG antibody responses in the DLN of mice was assessed following co-inoculation of VRP-GFP and dflu. At various time points post-boost (days 3, 7, 10, 14, 18, 21, and 28), animals were sacrificed and the DLN was harvested and allowed to incubate at 37° C. for 7 days in tissue culture media. The media was subsequently analyzed for HA-specific IgG antibodies via ELISA. FIG. 10 shows the reciprocal dilution at which the OD is >0.2.

HA-Specific IgA Antibody Production in DLN.

Figure 11:
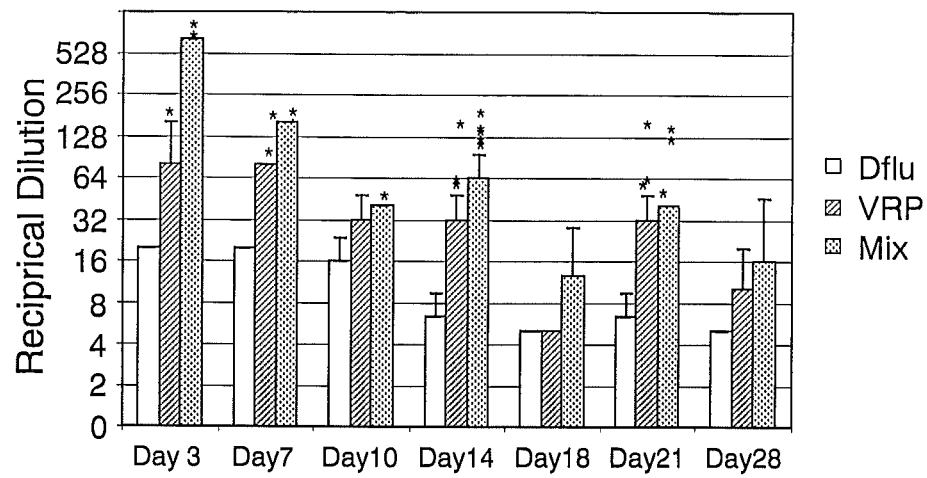
FIG. 11 shows HA-specific IgA antibody production in DLN of mice following inoculation with virus replicon particles expressing hemagglutinin (VRP), formalin-inactivated influenza virus (dflu), or a co-inoculation thereof (mix). Reciprocal dilution at which the OD is > two standard deviations over mock is shown.

Induction of HA-specific IgA antibody responses in the DLN of mice following co-inoculation of VRP-GFP and dflu. At various time points post-boost (days 3, 7, 10, 14, 18, 21, and 28), animals were sacrificed and the DLN was harvested and allowed to incubate at 37° C. for 7 days in tissue culture media. The media was subsequently analyzed for HA-specific IgG antibodies via ELISA. FIG. 11 shows the reciprocal dilution at which the OD is > two standard deviations over mock.

Example 5

HA-Specific Antibody Production in Draining Lymph Nodes

HA-Specific, Dimeric IgA Antibody Production in DLN.

Figure 12:
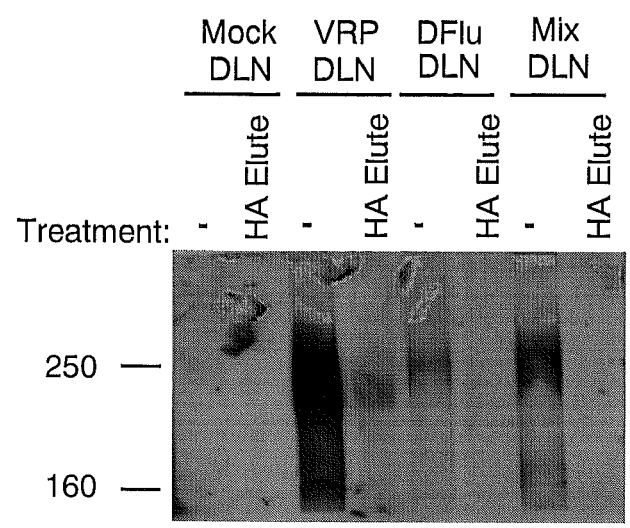
FIG. 12 shows antigen specific, dimeric IgA production in the draining lymph node (DLN) of mice mock inoculated or inoculated with virus replicon particles expressing hemagglutinin (VRP), formalin-inactivated influenza virus (dflu), or a co-inoculation thereof (mix).

Induction of antigen-specific, dimeric IgA in supernatants from the DLN of mice was assessed following co-inoculation of VRP-GFP and dflu. Three days post-boost, animals were sacrificed and the DLN, contralateral lymph node, and mesenteric lymph node were harvested and allowed to incubate at 37° C. for 7 days in tissue culture media. Tissue culture supernatants were then bound to HA-coated ELISA plates and washed with phosphate-buffered saline (PBS). HA-specific antibodies were then eluted from the ELISA plates, separated by SDS-PAGE under non-reducing conditions, and probed with an anti-IgA antibody. Dimeric IgA was visible as a >300 kDa band in mice inoculated with VRP-HA or co-inoculated with VRP-GFP and dflu (FIG. 12).

HA-Specific IgG and IgA Production in DLN.

Figure 13:
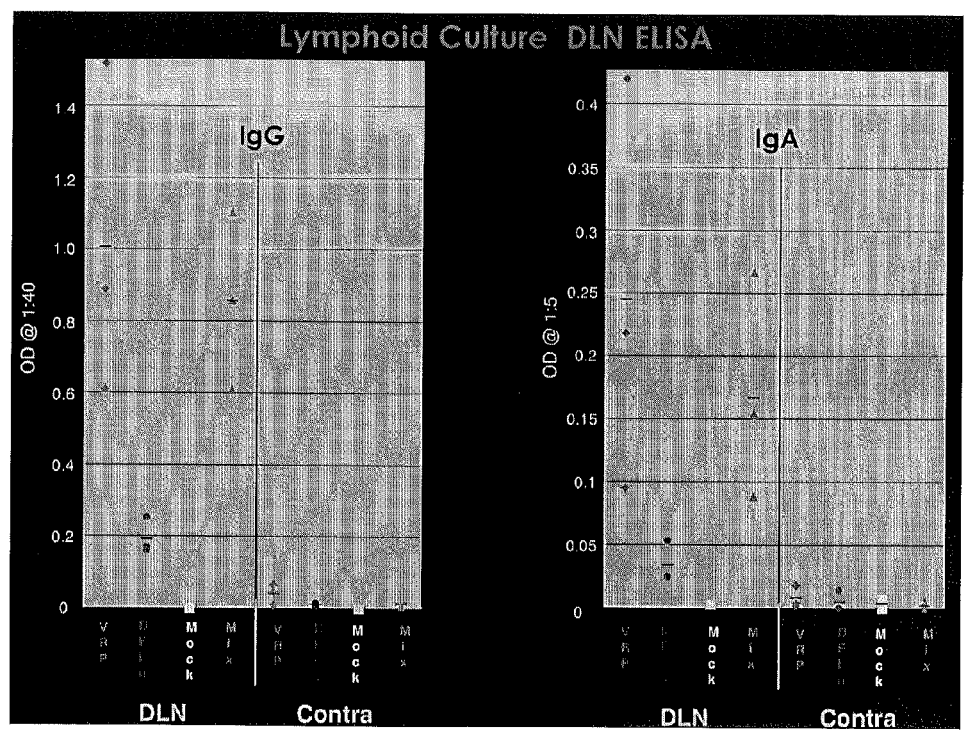
FIG. 13 shows optical density (OD) measurements of an ELISA for HA-specific IgG (1:40 dilution) and IgA (dilution 1:5) in the draining lymph node (DLN) and contralateral lymph node (Contra) from mice mock-inoculated or inoculated with virus replicon particles expressing hemagglutinin (VRP), formalin-inactivated influenza virus (dflu), or a co-inoculation thereof (mix).

Induction of HA-specific IgG and IgA antibodies in the DLN of mice was assessed following co-inoculation of VRP-GFP and dflu. Two weeks post-boost, animals were sacrificed and the DLN and contralateral lymph node were harvested and allowed to incubate at 37° C. for 7 days in tissue culture media. The media was subsequently analyzed for HA-specific IgG and IgA antibodies via ELISA. OD determinations were conducted on 1:40 dilutions for IgG and 1:5 dilutions for IgA (FIG. 13).

In summary, the data presented in Examples 3-5 demonstrate that VRP 1) possess immune-stimulating properties which are distinct from antigen production functions, and 2) VRP are capable of serving as both systemic and mucosal adjuvants to co-inoculated antigens. In these experiments, it has been demonstrated that VRP adjuvant activity is effective at inducing responses to inactivated viral particles as antigens, which present ordered, repeating antigens to the immune system. It is further demonstrated that VRP which express a transgene (in this case, GFP) possess adjuvant activity.

Example 6

Humoral Adjuvant Activity of VRP

In order to determine if Venezuelan Equine Encephalitis (VEE) replicon particles (VRP) are capable of serving as adjuvants for the induction of antigen-specific humoral immune responses, groups of eight Balb/c animals were vaccinated and boosted four weeks later with 10 μg of Ovalbumin (OVA), or 10 μg OVA co-inoculated with $1 \times 10^6$ infectious units (I.U.) of empty VRP (not expressing any antigen), either in the footpad (FP) or intranasal (IN). Three weeks post boost, animals were bleed and sera analyzed for the presence of OVA-specific IgG antibodies via ELISA. Antibody titers are presented as the reciprocal dilution which results in an optical density (OD)>0.2. As shown in FIG. 14A, VRP were capable of enhancing OVA-specific serum IgG titers by approximately 64 fold following footpad delivery, and approximately 1400 fold following nasal delivery. These data demonstrate that VRP possess intrinsic immune stimulating activity and that VRP are systemic adjuvants. In order to evaluate the ability of VRP to enhance mucosal immune responses, fecal extracts were prepared from immunized animals and assayed for the presence of OVA-specific IgG and IgA antibodies. As shown in FIGS. 14B and 14C, co-inoculation of OVA and VRP resulted in a significant increase in OVA-specific mucosal IgG (FIG. 14B) and IgA (FIG. 14C) in fecal extracts. These data demonstrate that VRP are capable of serving as mucosal adjuvant following both mucosal and non-mucosal delivery.

Example 7

VRP Adjuvant Activity is Comparable to Cholera Toxin

In order to determine if the enhancement observed with VRP are comparable to responses induced by the mucosal adjuvant, cholera toxin (CT), groups of eight Balb/c animals were vaccinated and boosted four weeks later in the footpad with PBS, 10 μg of Ovalbumin (OVA), 10 μg OVA co-inoculated with $1 \times 10^6$ I.U. of empty VRP (not expressing any antigen), or 10 μg OVA co-inoculated with 1 μg of CT. Three weeks post boost, fecal extracts were prepared from immunized animals and analyzed for the presence of OVA-specific antibodies via ELISA. Antibody titers are presented as the reciprocal dilution which results in an optical density (OD) >0.2. As shown in FIGS. 15A and 15B, the levels of OVA-specific IgG and IgA antibodies present in fecal extracts following co-delivery of VRP and OVA are indistinguishable from responses induced following co-delivery of OVA and CT. These data demonstrate that VRP-induced responses are comparable to responses induced by known mucosal adjuvants. Also, in order to demonstrate that adjuvant activity is in fact associated with replicon particles and not a contaminant in VRP preparations animals were treated with 10 μg OVA co-inoculated with an equivalent dilution of the supernatant from a mock electroporation (mE). If adjuvant activity is associated with a contaminant, such as LPS from VRP preparations, then responses induced following inoculation of OVA and mE should be indistinguishable from responses induced by OVA and VRP. As shown in FIGS. 15A and 15B, delivery of mE failed to stimulate any enhancement of OVA-specific antibody responses. These data support the conclusion that the replicon particles themselves are responsible for immune stimulation.

Example 8

VRP Possess Adjuvant Activity at Low Doses

In order to assess the ability of VRP to serve as adjuvants across a range of doses, groups of eight C57BL/6 animals were vaccinated and boosted four weeks later in the footpad with PBS, 10 μg of OVA, 10 μg OVA co-inoculated with $1 \times 10^2$ I.U. of empty VRP, $1 \times 10^3$ IU VRP, $1 \times 10^4$ IU VRP, $1 \times 10^5$ IU VRP, $1 \times 10^6$ IU VRP. Three weeks post boost, animals were bleed and sera analyzed for the presence of OVA-specific IgG antibodies via ELISA. Antibody titers are presented as the reciprocal dilution which results in an optical density (OD)>0.2. FIG. 16 demonstrates that VRP are capable of enhancing OVA-specific serum IgG titers at doses as low as $1 \times 10^2$ I.U. These data suggest that the immune induction reaction is quite efficient, as very few particles are required to induce a detectable enhancement.

Example 9

VRP RNA Replication is Required for Adjuvant Activity

Many cellular pathways have evolved to recognize viral products such as double-stranded RNA (ds RNA). It was hypothesized that one or more of these pathways may be involved in recognizing ds RNA produced following VRP infection and may play a critical role in VRP adjuvant activity. In order to test the hypothesis that VRP RNA replication serves as a trigger for adjuvant activity, groups of six Balb/c animals were vaccinated and boosted four weeks later in the footpad with 10 μg of OVA, 10 μg OVA co-inoculated with 1 μg of cholera toxin (CT), 10 μg OVA co-inoculated with $1 \times 10^4$ I.U. of empty VRP, 10 μg OVA co-inoculated with $1 \times 10^4$ I.U. empty VRP treated with ultraviolet (UV) light, or 10 μg of OVA co-inoculated with $1 \times 10^6$ I.U. empty VRP. One week post boost, serum was harvested from immunized animals and analyzed for the presence of OVA-specific IgG antibodies via ELISA. Also, animals were sacrificed and single cell suspensions were prepared from spleen and nasal epithelium, and analyzed for the presence of OVA-specific antibody-secreting-cells (ASCs) via standard ASC ELISPOT assay. UV treatment causes the formation of dimers in the VRP RNA, which blocks both translation of the input RNA as well as RNA replication. This treatment allows for the assessment of the role of RNA replication in the adjuvant activity. As demonstrated in FIG. 17A, it appears that VRP RNA replication is required for the observed adjuvant activity of VRP, as OVA-specific serum IgG titers are dramatically reduced following co-inoculation with UV-VRP. Treatment of VRP with UV light abrogates adjuvant activity to levels which are statistically indistinguishable from the immunity induced by OVA alone. This phenotype is also true in the mucosal compartment, as the numbers of OVA-specific ASCs in the nasal epithelium are dramatically reduced following VRP following co-inoculation with UV-VRP, compared to wt VRP (FIGS. 17B and 17C). Taken together, these data demonstrate the important role for VRP RNA replication in VRP-induced adjuvant activity.

Example 10

VRP Enhancement of T Cell Responses

The experiments presented above have clearly demonstrated that VRP are capable of enhancing both systemic and mucosal humoral immune responses following both mucosal and non-mucosal delivery in mice. The experiment described below was carried out to assess the ability of VRP to enhance T cell-mediated immune responses following non-mucosal delivery. In order to test the ability of VRP to serve as adjuvants for the induction of antigen-specific T cell responses groups of eight Balb/c animals were vaccinated and boosted four weeks later with PBS, 10 μg of SIV gp120 protein, 10 μg of gp120 co-inoculated with 1×10⁶ I.U. of empty VRP, or 1×10⁶ I.U. of VRP expressing full length SIV gp160. One week post boost, animals were sacrificed and spleens were isolated from immunized animals. Single cell suspensions were prepared from isolated spleens and analyzed for the presence of IFN-g-secreting cells via IFN-g ELISPOT following in vitro stimulation with either gp120 peptides or an irrelevant HA peptide. Numbers of IFN-g-secreting cells are displayed per 5×10⁵ cells. As shown in FIG. 18, VRP were capable of enhancing the number of gp120-specific IFN-g-secreting cells following co-delivery with gp120 protein. These results clearly demonstrate that VRP are capable of stimulating antigen-specific T cell responses (IFN-g) following co-delivery with protein antigen.

Example 11

VRP Enhancement of Norovirus-Specific Antibody Responses

The characterization of VRP humoral adjuvant activity in the experiments described above has relied on the use of HA or OVA as a test antigen. In order to verify that VRP are capable of enhancing immune responses to other infectious disease-related antigens, groups of six Balb/c animals were vaccinated and boosted four weeks later with PBS, 10 μg of Norwalk virus (NV) virus-like particles (VLP), 10 μg NV VLP co-inoculated with 1×10⁶ I.U. of empty VRP, or 10 μg NV VLP co-inoculated with 1 μg of CT. Three weeks post boost, animals were bled and fecal extracts were prepared from immunized animals and analyzed for the presence of OVA-specific IgG and IgA antibodies via ELISA. Antibody titers are presented as the reciprocal dilution which results in an optical density (OD)>0.2. Norwalk virus is a member of the Norovirus family and represents a significant human pathogen. Norwalk-like viruses are responsible for numerous outbreaks of infectious gastroenteritis on cruise ships which have resulted in severe diarrhea and significant economic losses. As shown in FIGS. 19A-19C, co-delivery of Norwalk virus VLPs and VRP resulted in a significant enhancement of NV-specific systemic (FIG. 19A) and mucosal (FIGS. 19B and 19C) antibody responses following non-mucosal delivery. These results suggest that VRP adjuvant activity is not restricted to the test antigen OVA and that VRP are capable of enhancing immune responses to medically relevant infectious agents.

The foregoing is illustrative of the present invention, and is not to be construed as limiting thereof. The invention is defined by the following claims, with equivalents of the claims to be included therein.

That which is claimed is:

1. An alphavirus adjuvant comprising:
   a modified alphavirus genomic nucleic acid that lacks sequences encoding the alphavirus structural proteins required for production of new alphavirus particles; wherein the modified alphavirus genome does not comprise a heterologous nucleic acid sequence that encodes a polypeptide of interest or a functional untranslated RNA and the 26S promoter is inactivated or deleted.

2. The alphavirus adjuvant of claim 1, wherein the alphavirus adjuvant is replication-competent.

3. The alphavirus adjuvant of claim 1, wherein the alphavirus adjuvant comprises a propagation-defective alphavirus particle that further comprises an alphavirus virion coat that packages the modified alphavirus genomic nucleic acid.

4. The alphavirus adjuvant of claim 1, wherein the modified alphavirus genomic nucleic acid does not comprise a heterologous nucleic acid sequence.

5. The alphavirus adjuvant of claim 1, wherein the alphavirus adjuvant is attenuated.

6. The alphavirus adjuvant of claim 1, wherein the modified alphavirus genomic nucleic acid is a modified Venezuelan Equine Encephalitis (VEE) viral genomic nucleic acid.

7. The alphavirus adjuvant of claim 6, wherein the alphavirus adjuvant comprises a propagation-defective VEE particle that further comprises a VEE virion coat that packages the VEE viral genomic nucleic acid.

8. The alphavirus adjuvant of claim 6, wherein the modified alphavirus genomic nucleic acid does not comprise a heterologous nucleic acid sequence.

9. A pharmaceutical formulation comprising the alphavirus adjuvant of claim 1 in a pharmaceutically acceptable carrier.

10. A composition comprising the alphavirus adjuvant of claim 1 and an immunogen.

11. A pharmaceutical formulation comprising the composition of claim 10 in a pharmaceutically acceptable carrier.

12. A helper cell for producing an alphavirus adjuvant comprising an infectious propagation-defective alphavirus particle, comprising in an alphavirus-permissive cell:
   (a) a modified alphavirus genomic RNA that comprises (i) sequences encoding the alphavirus nonstructural proteins, and (ii) a competent alphavirus packaging sequence, and (iii) wherein the modified alphavirus genomic nucleic acid lacks sequences encoding the alphavirus structural proteins required for production of new alphavirus particles; and further wherein the modified alphavirus genomic nucleic acid does not comprise a heterologous nucleic acid sequence that encodes a polypeptide of interest or a functional untranslated RNA and the 26S promoter is inactivated or deleted;
   (b) helper nucleic acid(s) encoding the alphavirus structural proteins sufficient for producing an alphavirus particle;
   wherein the combined expression of the modified alphavirus genomic RNA and the helper nucleic acid(s) encoding the alphavirus structural proteins produces an assembled alphavirus particle comprising the modified alphavirus genomic RNA.

13. The helper cell of claim 12, wherein the helper nucleic acid(s) are RNA molecules that are transfected into the helper cell.

14. The helper cell of claim 12, wherein the modified alphavirus genomic nucleic acid is a modified Venezuelan Equine Encephalitis (VEE) genomic nucleic acid.

15. The helper cell of claim 12, wherein the alphavirus adjuvant comprises a VEE virion coat and the helper nucleic acid(s) encodes VEE structural proteins.

16. The helper cell of claim 12, wherein the alphavirus adjuvant comprises infectious propagation-defective VEE particles, the modified alphavirus genomic nucleic acid is a modified VEE genomic nucleic acid, and the helper nucleic acid(s) encodes VEE structural proteins.

17. A method of making an alphavirus adjuvant comprising infectious propagation-defective alphavirus particles, comprising:
   (a) providing a helper cell according to claim 12;
   (b) producing the alphavirus particles in the helper cell; and
   (c) collecting the alphavirus particles from the helper cell.

18. A pharmaceutical formulation comprising the alphavirus adjuvant of claim 6 in a pharmaceutically acceptable carrier.

19. A pharmaceutical formulation comprising the alphavirus adjuvant of claim 7 in a pharmaceutically acceptable carrier.

20. A composition comprising the alphavirus adjuvant of claim 6 and an immunogen.

21. A composition comprising the alphavirus adjuvant of claim 7 and an immunogen.

* * * * *